US010364227B2

(12) United States Patent
Hecht et al.

(10) Patent No.: US 10,364,227 B2
(45) Date of Patent: Jul. 30, 2019

(54) THERAPEUTIC COMPOUNDS

(71) Applicant: ARIZONA BOARD OF REGENTS ON BEHALF OF ARIZONA STATE UNIVERSITY, Scottsdale, MN (US)

(72) Inventors: Sidney Hecht, Phoenix, AZ (US); Omar Khdour, Phoenix, AZ (US); Mohammad Alam, Tempe, AZ (US); Sriloy Dey, Tempe, AZ (US); Yana Chen, Tempe, AZ (US); Arnaud Chevalier, Bruere Allichanps (FR)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/550,273

(22) PCT Filed: Feb. 17, 2016

(86) PCT No.: PCT/US2016/018166
§ 371 (c)(1),
(2) Date: Aug. 10, 2017

(87) PCT Pub. No.: WO2016/133959
PCT Pub. Date: Aug. 25, 2016

(65) Prior Publication Data
US 2018/0319751 A1 Nov. 8, 2018

Related U.S. Application Data

(60) Provisional application No. 62/117,365, filed on Feb. 17, 2015.

(51) Int. Cl.
| | |
|---|---|
| *A61P 3/04* | (2006.01) |
| *A61P 9/00* | (2006.01) |
| *A61P 9/04* | (2006.01) |
| *A61P 9/10* | (2006.01) |
| *A61P 25/00* | (2006.01) |
| *A61P 25/16* | (2006.01) |
| *A61P 25/18* | (2006.01) |
| *A61P 25/28* | (2006.01) |
| *A61P 35/00* | (2006.01) |
| *C07D 239/47* | (2006.01) |
| *C07D 239/52* | (2006.01) |
| *C07D 401/04* | (2006.01) |
| *C07D 403/04* | (2006.01) |

(52) U.S. Cl.
CPC ............ *C07D 239/47* (2013.01); *A61P 3/04* (2018.01); *A61P 9/00* (2018.01); *A61P 9/04* (2018.01); *A61P 9/10* (2018.01); *A61P 25/00* (2018.01); *A61P 25/16* (2018.01); *A61P 25/18* (2018.01); *A61P 25/28* (2018.01); *A61P 35/00* (2018.01); *C07D 239/52* (2013.01); *C07D 401/04* (2013.01); *C07D 403/04* (2013.01)

(58) Field of Classification Search
CPC combination set(s) only.
See application file for complete search history.

(56) References Cited

U.S. PATENT DOCUMENTS

| | | |
|---|---|---|
| 3,476,722 A | 11/1969 | Schlatzer |
| 4,054,580 A | 10/1977 | Ohi |
| 4,338,180 A | 7/1982 | Nakamura |
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,220,042 A | 6/1993 | Iwaki et al. |
| 5,356,898 A | 10/1994 | Belliotti et al. |
| 8,268,849 B2 | 9/2012 | Kador et al. |
| 8,759,336 B2 | 6/2014 | Hurt et al. |
| 8,952,025 B2 | 2/2015 | Hecht et al. |
| 9,102,626 B2 | 8/2015 | Hecht et al. |
| 9,334,250 B2 | 5/2016 | Chowdhury et al. |
| 9,388,163 B2 | 7/2016 | Hecht et al. |
| 9,440,967 B2 | 9/2016 | Hecht et al. |
| 9,957,214 B2 | 5/2018 | Madathil et al. |
| 2001/0027196 A1 | 10/2001 | Borroni et al. |
| 2004/0166553 A1 | 8/2004 | Nguyen et al. |
| 2008/0062838 A1 | 3/2008 | Selinfreund et al. |

(Continued)

FOREIGN PATENT DOCUMENTS

| | | |
|---|---|---|
| DE | 2315349 A1 | 10/1974 |
| JP | 2001209176 A | 8/2001 |

(Continued)

OTHER PUBLICATIONS

Abe, et al., "Marked Reduction in CSF Lactate and Pyruvate Levels After CoQ Therapy in a Patient with Mitochondrial Myopathy, Encephalopathy, Lactic Acidosis and Stroke-like Episodes (MELAS)", Acta Neural Scand 83(6), 356-359 (1991).
Aguer, et al., "Galactose enhances oxidative metabolism and reveals mitochondrial dysfunction in human primary muscle cells", PLoS One 6(12), e28536 (2011).
Alam, et al., "Cytoprotective Pyridinol Antioxidants as Potential Therapeutic Agents for Neurodegenerative and Mitochondrial Diseases", Bioorganic & Medicinal Chemistry 22, 4935-4947 (2014).
Arce, et al., "A Strategy for Suppressing Redox Stress within Mitochondria", ACS Med Chem Lett 2(8), 608-613 (2011).

(Continued)

*Primary Examiner* — Amanda L Aguirre
(74) *Attorney, Agent, or Firm* — Viksnins Harris Padys Malen LLP

(57) ABSTRACT

Compounds of formula (I) and salts are disclosed. Also disclosed are isotopes of compounds of formula I of the salts thereof. Pharmaceutical compositions comprising a compound of formula I, processes for preparing compounds of formula I, intermediates useful for preparing compounds of formula I and therapeutic methods using a compound of formula I are disclosed.

21 Claims, 6 Drawing Sheets

(56) References Cited

U.S. PATENT DOCUMENTS

| | | | |
|---|---|---|---|
| 2010/0016783 A1 | 1/2010 | Bourke, Jr. et al. | |
| 2011/0319380 A1 | 12/2011 | Hardy et al. | |
| 2013/0224634 A1 | 8/2013 | Berneth et al. | |
| 2013/0267546 A1* | 10/2013 | Hecht .................. | C07D 213/74 514/273 |
| 2013/0267548 A1 | 10/2013 | Follmann et al. | |
| 2013/0317012 A1 | 11/2013 | Wischik et al. | |
| 2014/0127737 A1 | 5/2014 | Kim | |
| 2014/0275045 A1 | 9/2014 | Hinman et al. | |
| 2018/0065941 A1 | 3/2018 | Hecht et al. | |

FOREIGN PATENT DOCUMENTS

| | | | | |
|---|---|---|---|---|
| WO | 1996031217 A1 | 10/1996 | | |
| WO | 2002000683 A2 | 1/2002 | | |
| WO | 2003007950 A1 | 1/2003 | | |
| WO | 2006089301 A2 | 8/2006 | | |
| WO | 2006100212 A1 | 9/2006 | | |
| WO | 2009142760 A1 | 11/2009 | | |
| WO | 2011103536 A1 | 8/2011 | | |
| WO | 2012022467 A2 | 2/2012 | | |
| WO | 2012138713 A2 | 10/2012 | | |
| WO | 2013120081 A1 | 8/2013 | | |
| WO | WO-2013120040 A1 * | 8/2013 | ........... | A61K 31/336 |
| WO | 2014055629 A1 | 4/2014 | | |
| WO | 2014059158 A1 | 4/2014 | | |
| WO | 2014145119 A1 | 9/2014 | | |
| WO | 2016133959 A1 | 8/2016 | | |
| WO | 2016133995 A1 | 8/2016 | | |
| WO | 2017218537 A1 | 12/2017 | | |
| WO | 2016133959 A9 | 2/2018 | | |
| WO | 2018039077 A1 | 3/2018 | | |
| WO | 2018039487 A1 | 3/2018 | | |
| WO | 2018039077 A8 | 9/2018 | | |

OTHER PUBLICATIONS

Arce, et al., "Analysis of the structural and mechanistic factors in antioxidants that preserve mitochondrial function and confer cytoprotection", Bioorganic & Medicinal Chemistry 20(17), 5188-5201 (2012).
Armstrong, et al., "Cysteine starvation activates the redox-dependent mitochondrial permeability transition in retinal pigment epithelial cells", Invest Ophthalmol Vis Sci 45(11), 4183-4189 (2004).
Armstrong, et al., "Does Oxidative Stress Contribute to the Pathology of Friedreich's Ataxia? A Radical Question", FASEB J 24(7), 2152-2163 (2010).
Armstrong, et al., "Glutathione depletion enforces the mitochondrial permeability transition and causes cell death in Bcl-2 overexpressing HL60 cells", FASEB J 16(10), 1263-1265 (2002).
Armstrong, et al., "The coenzyme Q10 analog decylubiquinone inhibits the redox-activated mitochondrial permeability transition: role of mitochondrial respiratory chain complex III", J Biol Chem 278(49), 49079-49084 (2003).
Asin-Cayuela, et al., "Fine-tuning the hydrophobicity of a mitochondria-targeted antioxidant", FEBS Lett 571(1-3), 9-16 (2004).
Atamna, et al., "Methylene blue delays cellular senescence and enhances key mitochondrial biochemical pathways", FASEB J 22(3), 703-712 (2008, available online 2007).
Barbiroli, et al., "Coenzyme Q10 improves mitochondrial respiration in patients with mitochondrial cytopathies. An in vivo study on brain and skeletal muscle by phosphorous magnetic resonance spectroscopy", Cell Mol Biol 43(5), 741-749 (1997).
Barnham, et al., "Neurodegenerative diseases and oxidative stress", Nat Rev Drug Discov 3(3), 205-214 (2004).
Benard, et al., "Ultrastructure of the mitochondrion and its bearing on function and bioenergetics", Antioxid Redox Signal 10(8), 1313-1342 (2008).
Bencze, et al., "Human frataxin: iron and ferrochelatase binding surface", J.C.S. Chem. Commun. 14(18), 1798-1800 (2007).
Bendahan, et al., "31P NMR spectroscopy and ergometer exercise test as evidence for muscle oxidative performance improvement with coenzyme Q in mitochondrial myopathies", Neurology 42(6), 1203-1208 (1992).
Boduszek, et al., "A New Method for the Preparation of Pyridine-4-phosphonic Acids", Synthesis 1979(6), 452-453 (1979).
Bradley, et al., "Clinical, biochemical and molecular genetic correlations in Friedreich's ataxia", Hum. Mol. Genet. 9(2), 275-282 (2000).
Bras, et al., "Programmed cell death via mitochondria: different modes of dying", Biochemistry (Mosc) 70(2), 231-239 (2005).
Bresolin, et al., "Clinical and biochemical correlations in mitochondrial myopathies treated with coenzyme Q10", Neurology 38(6), 892-898 (1988).
Bresolin, et al., "Ubidecarenone in the treatment of mitochondrial myopathies: a multi-center double-blind trial", J Neuro Sci 100(1-2), 70-78 (1990).
Brigelius-Flohe, et al., "Vitamin E: function and metabolism", FASEB J 13(10), 1145-1155 (1999).
Brown, et al., "Potential Antimalarials in the 4-Dialkylaminomethyl-2-Methyl-3-Pyridol Series", J Org Chem 11(4), 388-389 (1946).
Bulteau, et al., "Frataxin Acts as an Iron Chaperone Protein to Modulate Mitochondrial Aconitase Activity", Science 305(5681), 242-245 (2004).
Burton, et al., "Vitamin E: application of the principles of physical organic chemistry to the exploration of its structure and function", Acc Chem Res 19(7), 194-201 (1986).
Cadenas, et al., "Mitochondrial free radical generation, oxidative stress, and aging", Free Radic Biol Med 29(3-4), 222-230 (2000).
Cadenas, et al., "Mitochondrial free radical production and cell signaling", Mol Aspects Med 25(1-2), 17-26 (2004).
Cai, et al., "Simplified bicyclic pyridinol analogues protect mitochondrial function", Bioorganic Med Chem 20(11), 3584-3595 (2012).
Calabrese, et al., "Oxidative stress, mitochondrial dysfunction and cellular stress response in Friedreich's ataxia", J Neuro Sci 233(1-2), 145-162 (2005).
Calza, et al., "Light-induced transformations of fungicides on titanium dioxide: pathways and by-products evaluation using the LC-MS technique", Int J Environ Anal Chem 86(3-4), 265-275 (2006).
Campuzano, et al., "Frataxin is Reduced in Friedreich Ataxia Patients and is Associated with Mitochondrial Membranes", Hum. Mol. Genet. 6(11), 1771-1780 (1997).
Campuzano, et al., "Friedreich's ataxia: autosomal recessive disease caused by an intronic GAA triplet repeat expansion", Science 271(5254), 1423-1427 (1996).
Castilho, et al., "Oxidative Damage of Mitochondria Induced by Fe(II)Citrate Is Potentiated by Ca2+ and Includes Lipid Peroxidation and Alterations in Membrane Proteins", Arch Biochem Biophys 308(1), 158-163 (1994).
Chevalier, et al., "Optimization of pyrimidinol antioxidants as mitochondrial protective agents: ATP production and metabolic stability", Bioorganic & Medicinal Chemistry 24, 5206-5220 (2016).
Chua, et al., "Oltipraz-induced phase 2 enzyme response conserved in cells lacking mitochondrial DNA", Biochem Biophys Res Commun 337(1), 375-381 (2005).
Chung, et al., "New 4-hydroxypyridine and 4-hydroxyquinoline derivatives as inhibitors of NADH-ubiquinone reductase in the respiratory chain", Z Naturforsch C 44(7-8), 609-616 (1989).
Corey, et al., "New and highly effective method for the oxidation of primary and secondary alcohols to carbonyl compounds", J Am Chem Soc 94(21), 7586-7587 (1972).
Corey, et al., "Pyridinium chlorochromate. An efficient reagent for oxidation of primary and secondary alcohols to carbonyl compounds", Tetrahedron Lett 16(31), 2647-2650 (1975).
Crompton, "The mitochondrial permeability transition pore and its role in cell death", Biochem J 341(2), 233-249 (1999).
D'Alessio, et al., "Apoptotic GSH extrusion is associated with free radical generation", Ann N Y Acad Sci 1010(1), 449-452 (2003).
De Hingh, et al., "Direct measurement of lipid peroxidation in submitochondrial particles", Biochemistry 34(39), 12755-12760 (1995).
Dimauro, et al., "Mitochondrial disorders in the nervous system", Annu Rev Neurosci 31, 91-123 (2008).

(56) References Cited

OTHER PUBLICATIONS

Dimauro, et al., "Mitochondrial DNA mutations in human disease", Am. J. Med Genet. 106(1), 18-26 (2001).
Droge, "Free Radicals in the Physiological Control of Cell Function", Physiol Rev 82(1), 47-95 (2002).
Drummen, et al., "C11-BODIPY(581/591), an oxidation-sensitive fluorescent lipid peroxidation probe: (micro) spectroscopic characterization and validation of methodology", Free Radic. Biol. Med 33(4), 473-490 (2002).
Durr, et al., "Clinical and genetic abnormalities in patients with Friedreich's ataxia", N Engl J Med 335(16), 1169-1175 (1996).
Ehrenberg, et al., "Membrane potential can be determined in individual cells from the nernstian distribution of cationic dyes", Biophy J 53, 785-794 (1988).
Fash, "Effects of alkyl side chain modification of coenzyme Q10 on mitochondrial respiratory chain function and cytoprotection", Bioorg Med Chem 21(8), 2346-2354 (2013).
Finkel, "Oxidant signals and oxidative stress", Curr Opin Cell Biol 15(2), 247-254 (2003).
Fiore, et al., "The mitochondrial ADP/ATP carrier: Structural, physiological and pathological aspects", Biochimie 80(2), 137-150 (1998).
Fisher, et al., "The Structure of Isomaltol", J Org Chem 29(4), 776-781 (1964).
Fridovich, "Fundamental aspects of reactive oxygen species, or what's the matter with oxygen?", Ann N Y Acad Sci 893(1), 13-18 (1999).
Frigerio, et al., "A User-Friendly Entry to 2-Iodoxybenzoic Acid (IBX)", J Org Chem 64(12), 4537-4538 (1999).
Gaetani, "Catalase and glutathione peroxidase are equally active in detoxification of hydrogen peroxide in human erythrocytes", Blood 73, 334-339 (1989).
Garcia-Rivas, "Ru360, a specific mitochondrial calcium uptake inhibitor, improves cardiac post-ischaemic functional recovery in rats in vivo", Br J Pharmacol 149(7), 829-837 (2006).
Genova, et al., "Mitochondrial production of oxygen radical species and the role of Coenzyme Q as an antioxidant", Exp Biol Med 228(5), 506-513 (2003).
Gille, et al., "Redox-interaction of alpha-tocopheryl quinone with isolated mitochondrial cytochrome bc1 complex", Biochem Pharmacol 68(2), 373-381 (2004).
Gillis, et al., "Idebenone. A review of its pharmacodynamic and pharmacokinetic properties, and therapeutic use in age-related cognitive disorders", Drugs Aging 5(2), 133-152 (1994).
Goda, et al., "Clinical improvement after administration of coenzyme Q10 in a patient with mitochondrial encephalomyopathy", J Neurol 234(2), 62-63 (1987).
Gold, et al., "Phosphorus magnetic resonance spectroscopy in the evaluation of mitochondrial myopathies: results of a 6-month therapy study with coenzyme Q", Eur Neurol 36(4), 191-196 (1996).
Goldschmidt, et al., "Effects of cytoprotective antioxidants on lymphocytes from representative mitochondrial neurodegenerative diseases", Bioorg. Med. Chem. 21, 969-978 (2013).
Gonzalez-Cabo, et al., "Frataxin interacts functionally with mitochondrial electron transport chain proteins", Hum. Mol. Genet. 14(15), 2091-2098 (2005).
Graier, et al., "Mitochondria and Ca(2+) signaling: old guests, new functions", Eur J Physiol 455, 375-396 (2007).
Green, et al., "Mitochondria and Apoptosis", Science 281(5381), 1309-1312 (1998).
Gregor, et al., "Distribution of tocopheryl quinone in mitochondrial membranes and interference with ubiquinone-mediated electron transfer", Biochem Pharmacol 71(11), 1589-1601 (2006).
Griffith, et al., "Potent and specific inhibition of glutathione synthesis by buthionine sulfoximine (S-n-butyl homocysteine sulfoximine)", J. Biol. Chem. 254(16), 7558-7560 (1979).
Harris, et al., "Structure of Vitamin B6. II", J Am Chem Soc 61(5), 1242-1244 (1939).
Hart, et al., "Antioxidant treatment of patients with Friedreich ataxia: four-year follow-up", Arch Neurol 62(4), 621-626 (2005).
Henze, et al., "Evolutionary biology: essence of mitochondria", Nature 426, 127-128 (2003).
Ihara, et al., "Mitochondrial encephalomyopathy (MELAS): pathological study and successful therapy with coenzyme Q10 and idebenone", J Neurol Sci 90(3), 263-271 (1989).
Ikejiri, et al., "Idebenone improves cerebral mitochondrial oxidative metabolism in a patient with MELAS", Neurology 47(2), 583-585 (1996).
Infante, et al., "A function for the vitamin E metabolite alpha-tocopherol quinone as an essential enzyme cofactor for the mitochondrial fatty acid desaturases", FEBS Lett 446(1), 1-4 (1999).
Ingold, et al., "A new vitamin E analogue more active than alpha-tocopherol in the rat curative myopathy bioassay", FEBS Lett 205(1), 117-120 (1986).
Inoue, et al., "Improved general method of ortho alkylation of phenols using alkyl isopropyl sulfide, sulfuryl chloride, and triethylamine. An expedient synthesis of representative oxygen heterocycles and (2R,4'R,8'R)-.alpha.-tocopherol", J Org Chem 52(24), 5495-5497 (1987).
Itoh, et al., "The substitution of 5-halo-1,2,3-triazines with electrolytically generated superoxide", Tetrahedron 47(25), 4317-4324 (1991).
Iuliano, et al., "Protection of low density lipoprotein oxidation by the antioxidant agent IRFI005, a new synthetic hydrophilic vitamin E analogue", Free Radic Biol Med 26(7-8), 858-868 (1999).
James, et al., "Interactions of Mitochondria-targeted and Untargeted Ubiquinones with the Mitochondrial Respiratory Chain and Reactive Oxygen Species: Implications for the use of exogenous ubiquinones as therapies and experimental tools", J. Biol. Chem. 280(22), 21295-21312 (2005).
Jauslin, et al., "A cellular model for Friedreich Ataxia reveals small-molecule glutathione peroxidase mimetics as novel treatment strategy", Hum. Mol. Genet. 11(24), 3055-3063 (2002).
Jefferson, et al., "Biaryl guanidine inhibitors of in vitro HCV-IRES activity", Bioorganic Med Chem Lett 14(20), 5139-5143 (2004).
Jenner, et al., "Oxidative stress in Parkinson's disease", Ann Neurol 53(Suppl. 3), S26-S38 (2003).
Joshi, et al., "Benzoquinoa Derivatives. Part I. Reactions of Primary Aliphatic Amines with Embelin (2,5-Dihydroxy-3-undecyl-1,4-benzoquinone) and Di-O-methylembelin", Journal of the Chemical Society, Perkins Transactions 1: Organic and Bio-Organic Chemistry, vol. 4, p. 327-332 (1975).
Jurma, et al., "Decreased glutathione results in calcium-mediated cell death in PC12", Free Radic Biol Med 23(7), 1055-1066 (1997).
Kamal-Eldin, et al., "The chemistry and antioxidant properties of tocopherols and tocotrienols", Lipids 31(7), 671-710 (1996).
Kao, et al., "Chapter 5—Practical Aspects of Measuring Intracellular Calcium Signals with Fluorescent Indicators", Methods Cell Biol 40, 155-181 (1994).
Katafias, et al., "Oxidation of phenothiazine dyes by manganese(III) in sulfuric acid solution", Transition Met Chem 36(8), 801-809 (2011).
Katsuki, et al., "The first practical method for asymmetric epoxidation", J Am Chem Soc 102(18), 5974-5976 (1980).
Kelso, et al., "Selective targeting of a redox-active ubiquinone to mitochondria within cells: antioxidant and antiapoptotic properties", J Biol Chem 276(7), 4588-4596 (2001, available online 2000).
Khdour, et al., "An acetate prodrug of a pyridinol-based vitamin E analogue", Pharm. Res 28(11), 2896-2909 (2011).
Khdour, et al., "An Optimized Pyrimidinol Multifunctional Radical Quencher", ACS Med Chem Lett 4(8), 724-729 (2013).
Kim, et al., "Efficient Synthesis of 4,5,6-Trisubstituted-2-aminopyrimidines", Bull Korean Chem Soc 30(9), 2107-2110 (2009).
Kim, et al., "Lipid-Soluble 3-Pyridinol Antioxidants Spare α-Tocopherol and Do Not Efficiently Mediate Peroxidation of Cholesterol Esters in Human Low-Density Lipoprotein", J Med Chem 48(22), 6787-6789 (2005).
Kohar, et al., "Is α-tocopherol a reservoir for α-tocopheryl hydroquinone?", Free Radic Biol Med 19(2), 197-207 (1995).
Korytnyk, et al., "On the Inhibitory Activity of 4-Vinyl Analogues of Pyridoxal: Enzyme and Cell Culture Studies", Biochemistry 15(25), 5458-5466 (1976).

(56) References Cited

OTHER PUBLICATIONS

Kowaltowski, et al., "Mitochondrial damage induced by conditions of oxidative stress", Free Radic Biol Med 26(3-4), 463-471 (1999).
Kowaltowski, et al., "Mitochondrial permeability transition and oxidative stress", FEBS Lett 495(1-2), 12-15 (2001).
Kowaltowski, et al., "The Thiol-specific Antioxidant Enzyme Prevents Mitochondrial Permeability Transition", J Biol Chem 273(21), 12766-12769 (1998).
Kuypers, et al., "Parinaric acid as a sensitive fluorescent probe for the determination of lipid peroxidation", Biochim Biophys Acta 921(2), 266-274 (1987).
La Marche, et al., "The Cardiomyopathy of Friedreich's Ataxia Morphological Observations in 3 Cases", Can J Neurosci 7, 389-396 (1980).
Lebel, et al., "Evaluation of the probe 2',7'-dichlorofluorescin as an indicator of reactive oxygen species formation and oxidative stress", Chem Res Toxicol 5(2), 227-231 (1992).
Leonard, et al., "Mitochondrial respiratory chain disorders I: mitochondrial DNA defects", Lancet 355(9200), 299-304 (2000).
Lerman-Sagie, et al., "Dramatic improvement in mitochondrial cardiomyopathy following treatment with idebenone", J Inherit Metab Dis 24(1), 28-34 (2001).
Ley, et al., "Tetrapropylammonium Perruthenate, Pr4N+RuO4−, TPAP: A Catalytic Oxidant for Organic Synthesis", Synthesis 1994(7), 639-666 (1994).
Lin, et al., "A nitrogen-containing 3-alkyl-1,4-benzoquinone and a gomphilactone derivative from Embelia ribes", J. Nat. Prod. 69(11), 1629-1632 (2006).
Lin, et al., "Mitochondrial dysfunction and oxidative stress in neurodegenerative diseases", Nature 443(7113), 787-795 (2006).
Lowes, et al., "The mitochondria-targeted antioxidant MitoQ protects against organ damage in a lipopolysaccharide-peptidoglycan model of sepsis", Free Radic Biol Med 45(11), 1559-1565 (2008).
Lu, et al., "Concise Synthesis of Bicyclic Pyridinol Antioxidants", Org Lett 12(22), 5189-5191 (2010).
Lu, et al., "Design, synthesis, and evaluation of an α-tocopherol analogue as a mitochondrial antioxidant", Bioorg Med Chem 18(21), 7628-7638 (2010).
Lu, et al., "Role of calcium and cyclophilin D in the regulation of mitochondrial permeabilization induced by glutathione depletion", Biochem Biophys Res Commun 363(3), 572-577 (2007).
Luly, et al., "Routes to Mitomycins, New Syntheses of the 2,3,5,8-Tetrahydro-5,8-dioxo-1H-pyrrolo[1,2a] indole Ring System. An Efficient Synthesis of 7-Methoxymitosene", J. Am. Chem. Soc. vol. 105, 2859-2866, (1983).
MacCoubrey, et al., "Quantitative fluorescence measurements of cell viability (cytotoxicity) with a multi-well plate scanner", J Cell Biol 111(5), 58a, (1990).
Mackenzie, et al., "The Biological Activity of Alpha-Tocopherylhydroquinone and Alpha-Tocopherylquinone", J Biol Chem 183(2), 655-662 (1950).
Manfredini, et al., "Novel antioxidant agents deriving from molecular combinations of vitamins C and E analogues: 3,4-dihydroxy-5(R)-[2(R,S)-(6-hydroxy-2,5,7,8-tetramethyl-chroman-2(R,S)-yl-methyl)-[1,3]dioxolan-4(S)-yl]-5H-furan-2-one and 3-O-octadecyl derivatives", Bioorg Med Chem 8(12), 2791-2801 (2000).
Manton, et al., "ROS effects on neurodegeneration in Alzheimer's disease and related disorders: on environmental stresses of ionizing radiation", Curr Alzheimer Res 1(4), 277-293 (2004).
Markesbery, et al., "Oxidative alterations in Alzheimer's disease", Brain Pathology 9(1), 133-146 (1999).
Markovits, et al., "Ethidium dimer: a new reagent for the fluorimetric determination of nucleic acids", Anal Biochem 94(2), 259-264 (1979).
Mates, et al., "Antioxidant enzymes and human diseases", Clin Biochem 32, 595-603 (1999).
Matlib, et al., "Oxygen-bridged dinuclear ruthenium amine complex specifically inhibits Ca2+ uptake into mitochondria in vitro and in situ in single cardiac myocytes", J Biol Chem 273(17), 10223-10231 (1998).

Matsuno-Yagi, et al., "Studies on the mechanism of oxidative phosphorylation: Catalytic site cooperativity in ATP synthesis", J. Biol. Chem. 260(27), 14424-14427 (1985).
Matthews, et al., "Coenzyme Q10 with multiple vitamins is generally ineffective in treatment of mitochondrial disease", Neurology 43(5), 884-890 (1993).
McBride, et al., "Mitochondria: more than just a powerhouse", Curr Biol 16, R551-R560 (2006).
McBride, et al., "Nucleotide chemistry. 16. Amidine protecting groups for oligonucleotide synthesis", J Am Chem Soc 108(8), 2040-2048 (1986).
McErlean, et al., "First Synthesis of N-(3-Carboxylpropyl)-5-amino-2-hydroxy-3-tridecyl-1,4-benzoquinone, an Unusual Quinone Isolated from Embelia ribes", Journal of Organic Chemistry, 72(26), 10298-10301 (2007).
Minta, et al., "Fluorescent indicators for cytosolic calcium based on rhodamine and fluorescein chromophores", J Biol Chem 264(14), 8171-8178 (1989).
Moore, et al., "A rapid pH insensitive, two color fluorescence viability (cytotoxicity) assay", J Cell Bio 111(5), 58a (1990).
Moore, et al., "Alpha-Tocopheryl Quinone is Converted into Vitamin E in Man", Free Radic Biol Med 22(5), 931-934 (1997).
Mossa, et al., "Alkylated benzoquinone derivatives from Maesa lanceolata", Phytochemistry 50(6), 1063-1068 (1999).
Moubarak, et al., "Hepatic metabolism of ergot alkaloids in beef cattle by cytochrome P450", Biochem Biophys Res Commun 274, 746-749 (2000).
Murphy, "Development of lipophilic cations as therapies for disorders due to mitochondrial dysfunction", Expert Opin Biol Ther 1(5), 753-764 (2001).
Murphy, et al., "Drug delivery to mitochondria: the key to mitochondrial medicine", Adv. Drug Delivery Rev. 41(2), 235-250 (2000).
Murphy, "How mitochondria produce reactive oxygen species", Biochem J 417(1), 1-13 (2009).
Nam, et al., "New synthetic route to N-tocopherol derivatives: synthesis of pyrrolopyridinol analogue of α-tocopherol from pyridoxine", Org Biomol Chem 9(6), 1749-1755 (2011).
Nam, et al. "Pyridoxine-derived bicyclic aminopyridinol antioxidants: synthesis and their antioxidant activities", Org Biomol Chem 9(24), 8475-8482 (2011).
Nam, et al., "Tetrahydro-1,8-naphthyridinol analogues of alpha-tocopherol as antioxidants in lipid membranes and low-density lipoproteins", J Am Chem Soc 129(33), 10211-10219 (2007).
Newmeyer, et al., "Erratum for Mitochondria: releasing power for life and unleashing the machineries of death", Cell 112(6), 873 (2003).
Newmeyer, et al., "Mitochondria: releasing power for life and unleashing the machineries of death", Cell 112(4), 481-490 (2003).
Niki, et al., "Dynamics of antioxidant action of vitamin E", Acc Chem Res 37(1), 45-51 (2004, available online 2003).
Ogasahara, et al., "Improvement of abnormal pyruvate metabolism and cardiac conduction defect with coenzyme Q10 in Kearns-Sayre syndrome", Neurology 35(3), 372-377 (1985).
Ogawa, "Hydroxybenzoquinones from myrsinaceae plants-II.: Distribution among myrsinaceae plants in Japan., Phytochemistry", Phytochemistry 7(5), 773-782 (1968).
Omura, et al., "Oxidation of alcohols by "activated" dimethyl sulfoxide. a preparative, steric and mechanistic study", Tetrahedron 34(11), 1651-1660 (1978).
Osakada, et al., "Alpha-tocotrienol provides the most potent neuroprotection among vitamin E analogs on cultured striatal neurons", Neuropharmacology 47(6), 904-915 (2004).
Osakada, et al., "Neuroprotective effects of alpha-tocopherol on oxidative stress in rat striatal cultures", Eur J Pharmacol 465(1-2), 15-22 (2003).
Ouahchi, et al., "Ataxia with isolated vitamin E deficiency is caused by mutations in the alpha-tocopherol transfer protein", Nat Genet 9(2), 141-145 (1995).
Palozza, et al., "Retracted: Design, synthesis, and antioxidant potency of novel α-tocopherol analogues in isolated membranes and intact cells", Free Redic Biol Med 44(7), 1452-1464 (2008).
Palozza, et al., "Retraction notice to: "Design, synthesis, and antioxidant potency of novel α-tocopherol analogues in isolated

(56) References Cited

OTHER PUBLICATIONS membranes and intact cells", [Free Radical Biology & Medicine 44 (2008) 1452-1464]", Free Redic Biol Med 75, 252 (2014).
Pap, et al., "Ratio-£uorescence microscopy of lipid oxidation in living cells usingC11-BODIPY581=591", FEBS Lett 453, 278-282 (1999).
Park, et al., "Yeast frataxin sequentially chaperones and stores iron by coupling protein assembly with iron oxidation", J. Biol. Chem. 278(33), 31340-31351 (2003).
Patent Cooperation Treaty, International Searching Authority, International Preliminary Report on Patentability and Written Opinion for PCT/US2011/025613, 8 pages, report dated Aug. 21, 2012.
Patent Cooperation Treaty, International Searching Authority, International Preliminary Report on Patentability and Written Opinion for PCT/US2012/032108, 9 pages, report dated Oct. 8, 2013.
Patent Cooperation Treaty, International Searching Authority, International Preliminary Report on Patentability and Written Opinion for PCT/US2013/025590, 8 pages, report dated Aug. 12, 2014.
Patent Cooperation Treaty, International Searching Authority, International Preliminary Report on Patentability and Written Opinion for PCT/US2013/063034, 5 pages, report dated Apr. 7, 2015.
Patent Cooperation Treaty, International Searching Authority, International Preliminary Report on Patentability and Written Opinion for PCT/US2013/064359, 6 pages, report dated Apr. 14, 2015, opinion dated Feb. 10, 2014.
Patent Cooperation Treaty, International Searching Authority, International Preliminary Report on Patentability and Written Opinion for PCT/US2016/018233, 12 pages, report dated Aug. 22, 2017, opinion dated Apr. 29, 2016.
Patent Cooperation Treaty, International Searching Authority, International Search Report for PCT/US2011/025613, 5 pages, dated Jul. 25, 2011.
Patent Cooperation Treaty, International Searching Authority, International Search Report for PCT/US2012/032108, 6 pages, dated Jan. 23, 2013.
Patent Cooperation Treaty, International Searching Authority, International Search Report for PCT/US2013/025590, 5 pages, dated May 6, 2013.
Patent Cooperation Treaty, International Searching Authority, International Search Report for PCT/US2013/063034, 3 pages, dated Nov. 15, 2013.
Patent Cooperation Treaty, International Searching Authority, International Search Report for PCT/US2013/064359, 3 pages, dated Feb. 10, 2014.
Patent Cooperation Treaty, International Searching Authority, International Search Report for PCT/US2016/018233, 4 pages, dated Apr. 29, 2016.
Patent Cooperation Treaty, International Searching Authority, International Search Report for PCT/US2017/037253, 2 pages, dated Aug. 16, 2017.
Patent Cooperation Treaty, International Searching Authority, International Search Report for PCT/US2017/047640, 3 pages, dated Oct. 30, 2017.
Patent Cooperation Treaty, International Searching Authority, International Search Report for PCT/US2017/048482, 4 pages, dated Dec. 7, 2017.
Patent Cooperation Treaty, International Searching Authority, Written Opinion for PCT/US2017/037253, 5 pages, dated Aug. 16, 2017.
Patent Cooperation Treaty, International Searching Authority, Written Opinion for PCT/US2017/047640, 4 pages, dated Oct. 30, 2017.
Patent Cooperation Treaty, International Searching Authority, Written Opinion for PCT/US2017/048482, 5 pages, dated Dec. 7, 2017.
Piancatelli, et al., "Pyridinium Chlorochromate: A Versatile Oxidant in Organic Synthesis", Synthesis 1982(4), 245-258 (1982).
Pisano, et al., "Plasma concentrations and pharmacokinetics of idebenone and its metabolites following single and repeated doses in young patients with mitochondrial encephalomyopathy", Eur J Clin 51(2), 167-169 (1996).
Pratt, et al., "5-Pyrimidinols: novel chain-breaking antioxidants more effective than phenols", J Am Chem Soc 123(19), 4625-4626 (2001).
Pubchem, "3H-Phenothiazin-3-one", CID 68485, 17 pages (Create Date Mar. 26, 2005).
Pubchem, "7-((4-nitrobenzyl)oxy)-2H-chromen-2-one", SID 164870287, create date Nov. 14, 2013, Version 1 (modified Nov. 14, 2013), retrieved Dec. 4, 2018, <https://pubchem.ncbi.nlm.nih.gov/substance/164870287/version/1>.
Pubchem, "7-((4-nitrobenzyl)oxy)-2H-chromen-2-one", SID 164870287, create date Nov. 14, 2013, Version 6 (modified Nov. 28, 2015), retrieved Dec. 4, 2018, <https://pubchem.ncbi.nlm.nih.gov/substance/164870287/version/6>.
Pubchem, "7-(dimethylamino)-3H-phenothiazin-3-one", SID 224730291, create date Feb. 2, 2015, Version 1 (modified Feb. 2, 2015), retrieved Dec. 4, 2018, <https://pubchem.ncbi.nlm.nih.gov/substance/224730291/version/1>.
Pubchem, "7-(dimethylamino)-3H-phenothiazin-3-one", SID 224730291, create date Feb. 2, 2015, Version 2 (modified Nov. 15, 2017), retrieved Dec. 4, 2018, <https://pubchem.ncbi.nlm.nih.gov/substance/224730291/version/2>.
Pubchem, "MLS002699551", SID 92763509, create date May 10, 2010, Version 1 (modified May 10, 2010), retrieved Dec. 4, 2018, <https://pubchem.ncbi.nlm.nih.gov/substance/92763509/version/1>.
Pubchem, "MLS002699551", SID 92763509, create date May 10, 2010, Version 3 (modified Mar. 1, 2012), retrieved Dec. 4, 2018, <https://pubchem.ncbi.nlm.nih.gov/substance/92763509/version/3>.
Quinzii, et al., "Respiratory chain dysfunction and oxidative stress correlate with severity of primary CoQ10 deficiency", FASEB J. 22(6), 1874-1885 (2008).
Ramasarma, et al., "Studies on the Electron Transport System", J Biol Chem 235(11), 3309-3314 (1960).
Reddy, "Amyloid precursor protein-mediated free radicals and oxidative damage: implications for the development and progression of Alzheimer's disease", J Neurochem 96(1), 1-13 (2006, available online 2005).
Reddy, et al., "Are mitochondria critical in the pathogenesis of Alzheimer's disease", Brain Res Brain Res Rev 49(3), 618-632 (2005).
Robuschi, et al., "The Action of Light and of Photodynamic Substances on Carbohydrate Metabolism", Sperimentale 94, 99-124 (1940).
Rotig, et al., "Molecular insights into Friedreich's ataxia and antioxidant-based therapies", Trends Mol Med 8(5), 221-224 (2002).
Rustin, et al., "Idebenone treatment in Friedreich patients: one-year-long randomized placebo-controlled trial", Neurology 62(3), 524-525 (2004).
Saraste, "Oxidative phosphorylation at the fin de siècle", Science 283, 1488-1493 (1999).
Scavo, et al., "Preparation of alpha,beta-dehydro-beta-amino acid derivatives by tin-promoted addition of malonates to simple nitriles", Tetrahedron Lett 26(22), 2603-2606 (1985).
Shue, et al., "Targeting antioxidants to mitochondria: a new therapeutic direction", Biochim Biophys Acta 1762(2), 256-265 (2006, available online 2005).
Smith, "[13] Preparation, properties, and conditions for assay of mitochondria: Slaughterhouse material, small-scale", Methods Enzymol 10, 81-86 (1967).
Smith, et al., "Delivery of Bioactive Molecules to Mitochondria in vivo", PNAS, vol. 100, No. 9, 5407-5412 (2003).
Smith, et al., "Measurement of protein using bicinchoninic acid", Anal Biochem 150(1), 76-85 (1985).
Smith, et al., "Using mitochondria-targeted molecules to study mitochondrial radical production and its consequences", Biochem Soc Trans 31(6), 1295-1299 (2003).
Syper, "The Baeyer-Villiger Oxidation of Aromatic Aldehydes and Ketones with Hydrogen Peroxide Catalyzed by Selenium Compounds. A Convenient Method for the Preparation of Phenols", Synthesis 1989(3), 167-172 (1989).
Takano, et al., "An Efficient Stereoselective Preparation of Vitamin E (α-Tocopherol) from Phytol", Synlett 1990(8), 451-452 (1990).

(56) References Cited

OTHER PUBLICATIONS

Takano, et al., "Asymmetric construction of optically active 3-hydroxyalkyne functionalities", J Chem Soc Chem Commun (18), 1344-1345 (1989).
Takenaka, et al., "The effect of alpha-tocopherol as an antioxidant on the oxidation of membrane protein thiols induced by free radicals generated in different sites", Arch Biochem Biophys 285(2), 344-350 (1991).
Tallman, et al., "Kinetic Products of Linoleate Peroxidation: Rapid β-Fragmentation of Nonconjugated Peroxyls", J Am Chem Soc 123(47), 11827-11828 (2001).
Tirmenstein, et al., "Glutathione depletion and the production of reactive oxygen species in isolated hepatocyte suspensions", Chem Biol Interact 127(3), 201-217 (2000).
Traber, et al., "Human plasma vitamin E kinetics demonstrate rapid recycling of plasma RRR-alpha-tocopherol", Proc Natl Acad Sci USA 91(21), 10005-10008 (1994).
Traber, et al., "Preferential incorporation of alpha-tocopherol vs gamma-tocopherol in human lipoproteins", Am J Clin Nutr 49(3), 517-526 (1989).
Trnka, et al., "Antioxidant properties of MitoTEMPOL and its hydroxylamine", Free Radic Res 43(1), 4-12 (2009).
Trounce, et al., "Assessment of mitochondrial oxidative phosphorylation in patient muscle biopsies, lymphoblasts, and transmitochondrial cell lines", Methods Enzymol. 264, 484-509 (1996).
Turrens, "Mitochondrial formation of reactive oxygen species", J Physiol 552, 335-344 (2003).
USPTO, Final Office Action for U.S. Appl. No. 13/855,133, dated Jun. 17, 2014, 9 pages.
USPTO, Final Office Action for U.S. Appl. No. 14/009,437, dated Mar. 18, 2015, 8 pages.
USPTO, Final Office Action for U.S. Appl. No. 14/371,579, dated Sep. 2, 2015, 11 pages.
USPTO, Final Office Action for U.S. Appl. No. 14/434,725, notification date Feb. 28, 2017, 10 pages.
USPTO, Non-Final Office Action for U.S. Appl. No. 13/855,133, dated Dec. 3, 2013, 10 pages.
USPTO, Non-Final Office Action for U.S. Appl. No. 14/009,437, dated Dec. 9, 2014, 8 pages.
USPTO, Non-Final Office Action for U.S. Appl. No. 14/371,579, dated Mar. 18, 2015, 17 pages.
USPTO, Non-Final Office Action for U.S. Appl. No. 14/432,885, dated Nov. 12, 2015, 6 pages.
USPTO, Non-Final Office Action for U.S. Appl. No. 14/434,725, notification date Aug. 23, 2017, 12 pages.
USPTO, Non-Final Office Action for U.S. Appl. No. 14/434,725, notification date Aug. 29, 2016, 17 pages.
USPTO, Non-Final Office Action for U.S. Appl. No. 14/731,950, dated Nov. 6, 2015, 7 pages.
Van Haaften, et al., "No reduction of alpha-tocopherol quinone by glutathione in rat liver microsomes", Biochem Pharmacol 61(6), 715-719 (2001).
Viehe, et al., "The captodative effect", Acc Chem Res 18(5), 148-154 (1985).
Vinod, et al., "Os(VIII) as an Efficient Homogeneous Catalyst for the Oxidative Decolorization of Methylene Blue Dye with Alkaline Chloramine-T: Kinetic, Mechanistic, and Platinum Metal Ions Reactivity Studies", Ind Eng Chem Res 49(7), 3137-3145 (2010).
Wallace, "Mouse models for mitochondrial disease", Am J Med Genet 106(1), 71-93 (2001).
Wijtmans, et al., "6-Amino-3-Pyridinols: Towards Diffusion-Controlled Chain-Breaking Antioxidants", Angew Chem Int Ed 42(36), 4370-4373 (2003).
Wijtmans, et al., "Synthesis and Reactivity of Some 6-Substituted-2,4-dimethyl-3-pyridinols, a Novel Class of Chain-Breaking Antioxidants", J. Org. Chem.69(26), 9215-9223 (2004).
Wilson, "Frataxin and frataxin deficiency in Friedreich's ataxia", J. Neurol. Sci. 207(1-2), 103-105 (2003).
Wilson, et al., "Respiratory deficiency due to loss of mitochondrial DNA in yeast lacking the frataxin homologue", Nature Genetics 16(4), 352-357 (1997).
Wright, et al., "Lifespan and mitochondrial control of neurodegeneration", Nat Genet 36(11), 1153-1158 (2004).
Wu, et al., "Autoxidation of phosphatidylcholine liposomes", Lipids 17(6), 403-413 (1982).
Yamada, et al., "Immunochemical detection of a lipofuscin-like fluorophore derived from malondialdehyde and lysine", J. Lipid Res. 42(8), 1187-1196 (2001).
Yin, et al., "Biochemical basis of lipofuscin, ceroid, and age pigment-like fluorophores", Free Rad. Biol. Med. 21(6), 871-888 (1996).
Ying, et al., "Inhibition of mitochondrial calcium ion transport by an oxo-bridged dinuclear ruthenium ammine complex", Biochemistry 30(20), 4949-4952 (1991).
Yoon, et al., "Frataxin-mediated Iron Delivery to Ferrochelatase in the Final Step of Heme Biosynthesis", J. Biol. Chem. 279(25), 25943-25946 (2004).
Yoon, et al., "Iron-sulfur cluster biosynthesis. Characterization of frataxin as an iron donor for assembly of [2Fe—2S] clusters in ISU-type proteins", J. Am. Chem. Soc. 125(20), 6078-6084 (2003).
Yoshihara, et al., "Hydroxybenzoquinones from Myrsinaceae Plants. IV. Further Confirmation of the Structures of Ardisiaquinones and Some Observations on Alkylaminobenzoquinone Derivatives", Chem Pharm Bull 16(12), 2383-2389 (1968).
Zhang, et al., "Bax and the mitochondrial permeability transition cooperate in the release of cytochrome c during endoplasmic reticulum-stress-induced apoptosis", Cell Death Differ 14(4), 703-715 (2007, available online 2006).
Zhang, et al., "The mitochondrial permeability transition regulates cytochrome c release for apoptosis during endoplasmic reticulum stress by remodeling the cristae junction", J Biol Chem 283(6), 3476-3486 (2008, available online 2007).
Zierz, et al., "Exogenous coenzyme Q (coq) fails to increase coq in skeletal muscle of two patients with mitochondrial myopathies", J Neurol Sci 95(3), 283-290 (1990).
Zimmerman, et al., "Mitochondrial Dysfunction and Mitochondrial-Produced Reactive Oxygen Species: New Targets for Neurogenic Hypertension?", Hypertension 53(2), 112-114 (2008).
L'Vova, et al., "Heterodiene condensation of 4-methyl-5-propoxyoxazole with vinylethynyldimethylcarbinol", Zhurnal Organicheskoi Khimii 11(7), 1537-1540 (1975).
Patent Cooperation Treaty, International Searching Authority, Search Report and Written Opinion for PCT/US2016/18166, 10 pages, dated Apr. 29, 2016.

* cited by examiner

THERAPEUTIC COMPOUNDS

PRIORITY OF INVENTION

This application claims priority from U.S. Provisional Patent Application No. 62/117,365, filed 17 Feb. 2015, which is hereby incorporated by reference in its entirety.

BACKGROUND

Mitochondria are central key organelles to regulate a multitude of different metabolic and signaling pathways and also play an important role in programmed cell death ((McBride et al. (2006) *Curr Biol.* 16:R551; Graier et al. (2007) *Eur J Physiol.* 455, 375). The primary function of mitochondria is to produce ATP through the process of oxidative phosphorylation (OXPHOS), which is performed by the four respiratory complexes (complexes I-IV) and the ATP synthase (complex V), all located in the inner mitochondrial membrane (Saraste et al. (1999) *Science,* 283, 1488; Henze et al. (2003) *Nature,* 426, 127). In mitochondria superoxide ($O_2.^-$) is generated at several sites within the electron-transport chain (ETC), which is linked to bioenergetic function. However, faulty electron transfer at any point in the electron transport chain has a major impact on mitochondrial coupling (ATP synthesis) and production of reactive oxygen species (Murphy et al. (2009) *Biochem J.* 417, 1; Turrens et al. (2003) *J Physiol.* 552,335). Normally, mitochondria likely serve as a net sink rather than a net source of ROS (Mates et al. (1999) *Clin Biochem.* 32, 595; Gaetani et al. (1989) *Blood.* 73, 334). The cells have developed a number of efficient scavenger systems including antioxidant enzymes and the glutathione redox cycle with its associated constitutive enzymes as well as glutathione itself in the mitochondria and cytosol to cope with the normal production of reactive oxygen species. Superoxide is converted rapidly to hydrogen peroxide ($H_2O_2$) by spontaneous dismutation using superoxide dismutase (SOD) in the mitochondrial matrix (MnSOD) and the inter membrane space (IMS) and cytosol (CuZnSOD). Peroxidases and catalases also participate in the conversion of reactive oxygen species to water. The impaired oxidative phosphorylation function (OXPHOS) would lead to further production of ROS, which further overwhelms the endogenous antioxidant systems and exposing cellular macromolecules to oxidative damage. Mitochondrial diseases are a clinically heterogeneous group of disorders that arise as a result of dysfunction of the mitochondrial respiratory chain. They can be caused by mutation of genes encoded by either nuclear DNA or mitochondrial DNA (mtDNA). While some mitochondrial disorders only affect a single organ (e.g., the eye in Leber hereditary optic neuropathy [LHON]), many involve multiple organ systems and often present with prominent neurologic and myopathic features. The underlying biochemistries of these diseases tend to be rather similar. They include increased lactate production, diminished respiration and ATP production, and reflect the consequences of oxidative stress.

Accordingly, there is a need for therapeutic agents that are useful for the treatment or suppression of diseases associated with impaired mitochondria. There is also a need for agents that raise ATP levels and/or suppress oxidative stress and/or lipid peroxidation.

SUMMARY OF THE INVENTION

One embodiment provides a compound of formula I:

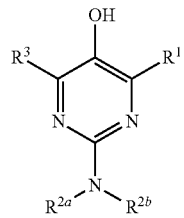

wherein:

$R^1$ is $(C_6$-$C_{26})$alkyl, $(C_6$-$C_{26})$alkenyl, $(C_6$-$C_{26})$alkynyl, —$O(C_6$-$C_{26})$alkyl, —$O(C_6$-$C_{26})$alkenyl or —$O(C_6$-$C_{26})$alkynyl, wherein any $(C_6$-$C_{26})$alkyl, $(C_6$-$C_{26})$alkenyl, $(C_6$-$C_{26})$alkynyl, —$O(C_6$-$C_{26})$alkyl, —$O(C_6$-$C_{26})$alkenyl or —$O(C_6$-$C_{26})$alkynyl of $R^1$ is optionally substituted with one or more groups independently selected from halogen, CN, $NO_2$, —$OR^{a1}$, —$N(R^{b1})_2$, —$CO_2R^{a1}$ and —$CON(R^{b1})_2$;

$R^{2a}$ and $R^{2b}$ are each independently hydrogen, $(C_1$-$C_6)$alkyl, $(C_2$-$C_6)$alkenyl or $(C_2$-$C_6)$alkynyl, wherein any $(C_1$-$C_6)$alkyl, $(C_2$-$C_6)$alkenyl or $(C_2$-$C_6)$alkynyl of $R^{2a}$ and $R^{2b}$ is optionally substituted with one or more groups independently selected from halogen, CN, $NO_2$, —$OR^{a2}$, —$N(R^{b2})_2$, —$CO_2R^{a2}$ and —$CON(R^{b2})_2$; or $R^{2a}$ and $R^{2b}$ together with the nitrogen to which they are attached form a 3-7 membered heterocyclyl wherein the heterocyclyl is optionally substituted with one more groups independently selected from halogen, $(C_1$-$C_6)$alkyl, $(C_2$-$C_6)$alkenyl, $(C_2$-$C_6)$alkynyl, CN, $NO_2$, —$OR^{a2}$, —$N(R^{b2})_2$, —$CO_2R^{a2}$ and —$CON(R^{b2})_2$;

$R^3$ is a carbocyclyl or —Ocarbocyclyl, wherein any carbocyclyl or —Ocarbocyclyl of $R^3$ is optionally substituted with one or more groups independently selected from halogen, CN, $NO_2$, —$OR^{a3}$, —$N(R^{b3})_2$, —$CO_2R^{a3}$ and —$CON(R^{b3})_2$;

each $R^{a1}$ is independently hydrogen, $(C_1$-$C_6)$alkyl, $(C_2$-$C_6)$alkenyl, $(C_2$-$C_6)$alkynyl or $(C_3$-$C_7)$carbocyclyl, wherein any $(C_1$-$C_6)$alkyl, $(C_2$-$C_6)$alkenyl, $(C_2$-$C_6)$alkynyl or $(C_3$-$C_7)$carbocyclyl of $R^{a1}$ is optionally substituted with one more halogen;

each $R^{b1}$ is independently hydrogen, $(C_1$-$C_6)$alkyl, $(C_2$-$C_6)$alkenyl, $(C_2$-$C_6)$alkynyl or $(C_3$-$C_7)$carbocyclyl, wherein any $(C_1$-$C_6)$alkyl, $(C_2$-$C_6)$alkenyl, $(C_2$-$C_6)$alkynyl or $(C_3$-$C_7)$carbocyclyl of $R^{b1}$ is optionally substituted with one more halogen, or two $R^{b1}$ groups together with the nitrogen to which they are attached form a 3-7 membered heterocyclyl optionally substituted with one or more halogen;

each $R^{a2}$ is independently hydrogen, $(C_1$-$C_6)$alkyl, $(C_2$-$C_6)$alkenyl, $(C_2$-$C_6)$alkynyl or $(C_3$-$C_7)$carbocyclyl, wherein any $(C_1$-$C_6)$alkyl, $(C_2$-$C_6)$alkenyl, $(C_2$-$C_6)$alkynyl or $(C_3$-$C_7)$carbocyclyl of $R^{a2}$ is optionally substituted with one more halogen;

each $R^{b2}$ is independently hydrogen, $(C_1$-$C_6)$alkyl, $(C_2$-$C_6)$alkenyl, $(C_2$-$C_6)$alkynyl or $(C_3$-$C_7)$carbocyclyl, wherein any $(C_1$-$C_6)$alkyl, $(C_2$-$C_6)$alkenyl, $(C_2$-$C_6)$alkynyl or $(C_3$-$C_7)$carbocyclyl of $R^{b2}$ is optionally substituted with one more halogen, or two $R^{b2}$ groups together with the nitrogen to which they are attached form a 3-7 membered heterocyclyl optionally substituted with one or more halogen;

each $R^{a3}$ is independently hydrogen, $(C_1$-$C_6)$alkyl, $(C_2$-$C_6)$alkenyl, $(C_2$-$C_6)$alkynyl or $(C_3$-$C_7)$carbocyclyl, wherein any $(C_1-C_6)$alkyl, $(C_2-C_6)$alkenyl, $(C_2-C_6)$alkynyl or $(C_3-C_7)$carbocyclyl of $R^{a3}$ is optionally substituted with one more halogen; and each $R^{b3}$ is independently hydrogen, $(C_1-C_6)$alkyl, $(C_2-C_6)$alkenyl, $(C_2-C_6)$alkynyl or $(C_3-C_7)$carbocyclyl, wherein any $(C_1-C_6)$alkyl, $(C_2-C_6)$alkenyl, $(C_2-C_6)$alkynyl or $(C_3-C_7)$carbocyclyl of $R^{b3}$ is optionally substituted with one more halogen, or two $R^{b3}$ groups together with the nitrogen to which they are attached form a 3-7 membered heterocyclyl optionally substituted with one or more halogen;

or a salt thereof.

One embodiment provides a compound of formula I or a pharmaceutically acceptable salt thereof as described herein, wherein one or more carbons of the compound of formula I is deuterated.

One embodiment provides a pharmaceutical composition comprising a compound of formula I or a pharmaceutically acceptable salt thereof as described herein and a pharmaceutically acceptable carrier.

One embodiment provides a method of treating a mitochondrial disease, obesity, heart disease, central nervous system disorder, cancer, fragile X syndrome or chronic fatigue syndrome in an animal (e.g., a mammal such as a human) comprising administering to the animal (e.g., a mammal such as a human) in need thereof a compound of formula I or a pharmaceutically acceptable salt thereof as described herein.

One embodiment provides a compound of formula I or a pharmaceutically acceptable salt thereof as described herein for use in medical therapy.

One embodiment provides a compound of formula I or a pharmaceutically acceptable salt thereof as described herein for the prophylactic or therapeutic treatment of a mitochondrial disease, obesity, heart disease, central nervous system disorder, cancer, fragile X syndrome or chronic fatigue syndrome.

One embodiment provides the use of a compound of formula I or a pharmaceutically acceptable salt thereof as described herein to prepare a medicament for treating a mitochondrial disease, obesity, heart disease, central nervous system disorder, cancer, fragile X syndrome or chronic fatigue syndrome in an animal (e.g., a mammal such as a human).

One embodiment provides processes and intermediates disclosed herein that are useful for preparing a compound of formula I or a salt thereof.

BRIEF DESCRIPTION OF THE FIGURES

FIG. 3 shows a bar graph of the means of the percentage of cells with intact ($\Delta\psi_m$) recorded by FACS (C6 Accuri, BD Biosciences, San Jose, Calif.).

DETAILED DESCRIPTION

Figure 1:
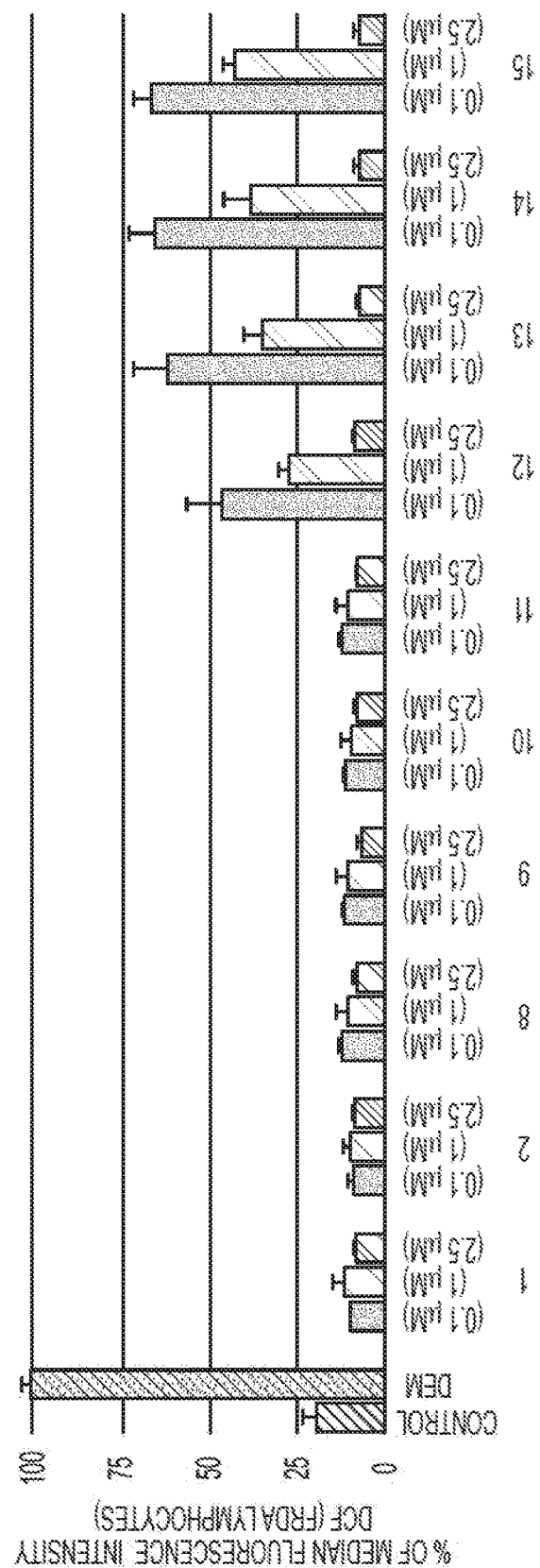
FIG. 1. Flow cytometric analysis of FRDA lymphocyte cells stained with dichlorofluorescein diacetate (DCFH-DA) for 20 min, following pretreatment with the test compounds at 0.1, 1 and 2.5 µM concentrations for 16 h, and subsequent treatment with diethyl maleate (DEM) for 1 h to induce the production of ROS. Increased DCF fluorescence, a measure of intracellular oxidation and ROS production was plotted as the percentage of the median fluorescence intensity of DCF fluorescence relative to a DEM-treated control.
Figure 2:
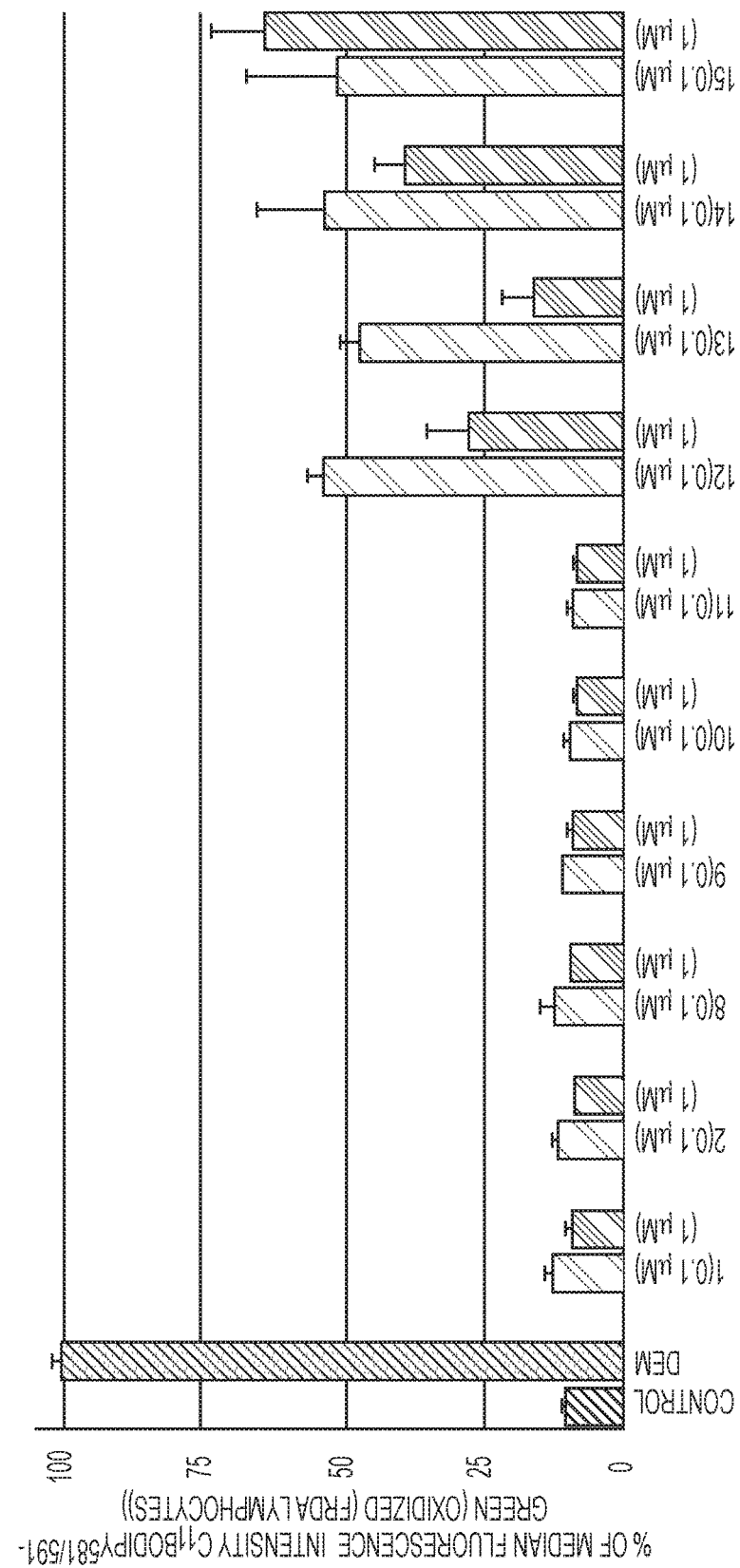
FIG. 2. Lipid peroxidation in FRDA lymphocytes depleted of glutathione was detected by utilizing the oxidation-sensitive fatty acid probe C11-BODIPY581/591 using flow cytometry. Increased $C_{11}$-BODIPY-green fluorescence (oxidized form), a measure of intracellular lipid peroxidation, was determined by increasing the median fluorescence intensity of $C_{11}$-BODIPY-green relative to the untreated control. A bar graph representing the percentage of the median fluorescence intensity of $C_{11}$-BODIPY-green fluorescence relative to a treated control is shown.
Figure 3:
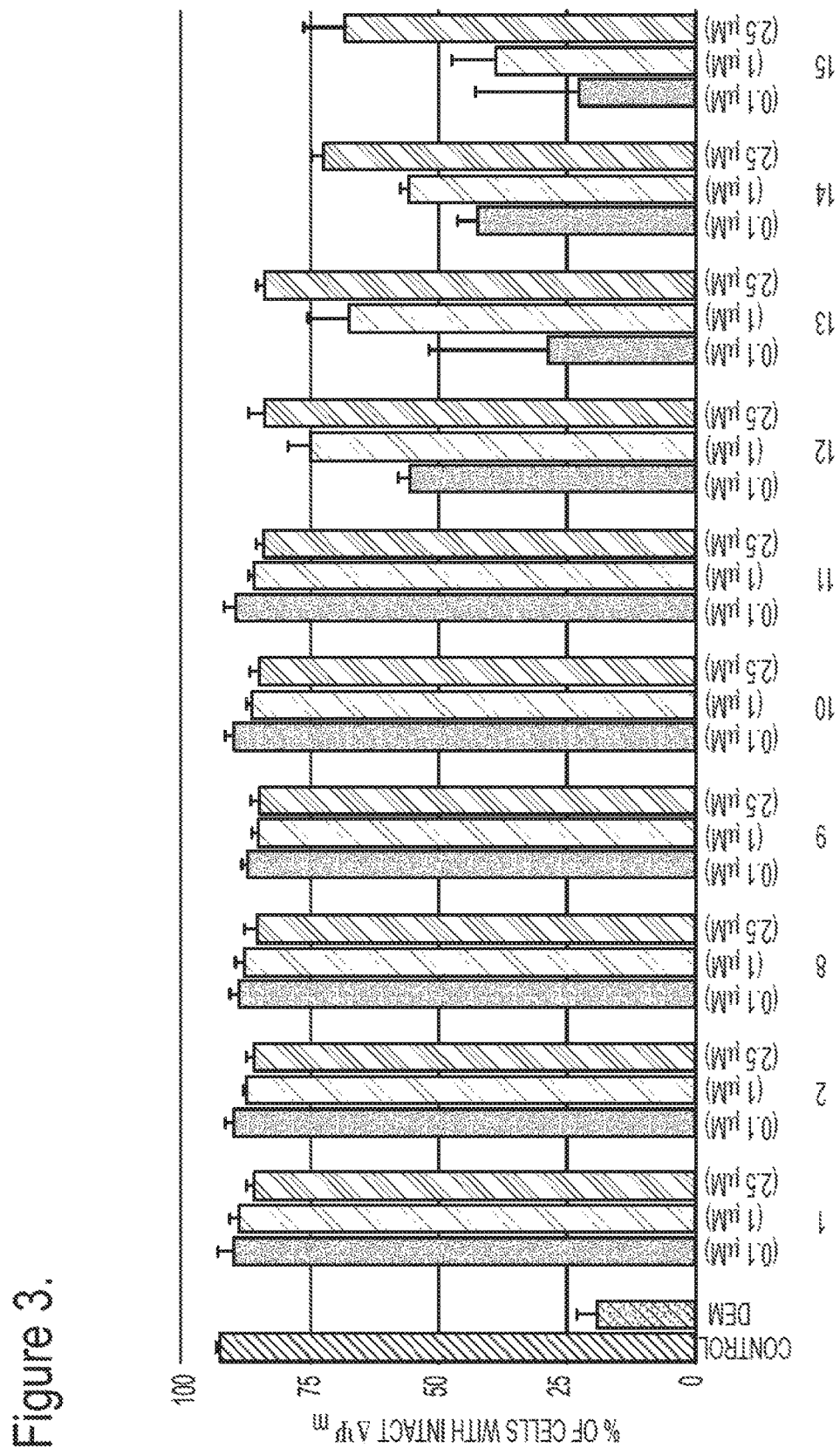
FIG. 3. Analyses of mitochondrial membrane potential ($\Delta\psi_m$) of FRDA lymphocyte cells stained with 250 nM TMRM and analyzed using the FL2-H channel as described in the experimental section. A total of 10,000 events were recorded for each sample and analyzed with the CellQuest software (BD Biosciences).
Figure 4:
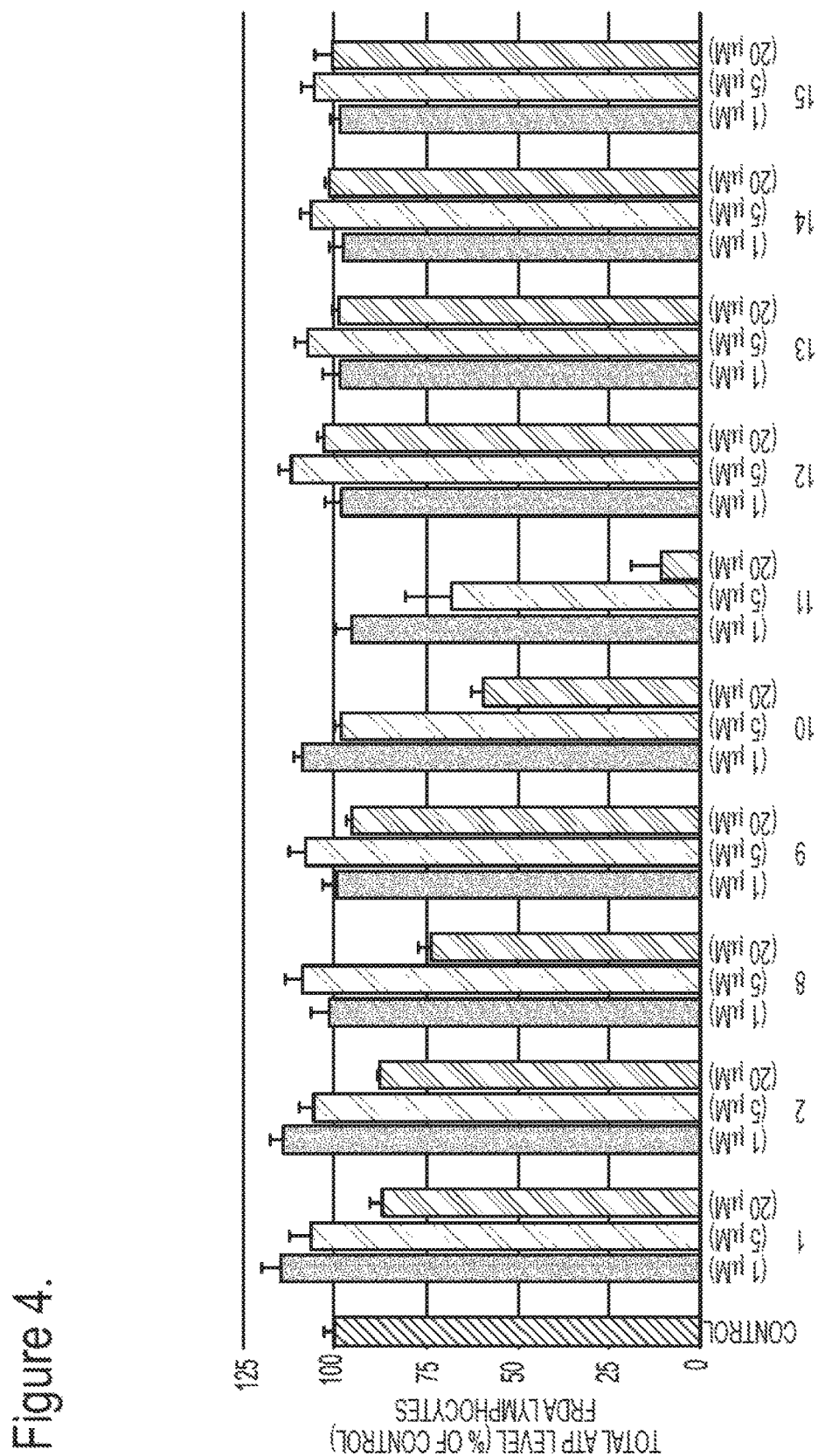
FIG. 4. Total ATP level in FRDA lymphocytes following incubation with test compounds for 48 h in glucose free media (25 mM galactose). Results are expressed as percentage of total ATP relative to untreated control.
Figure 5:
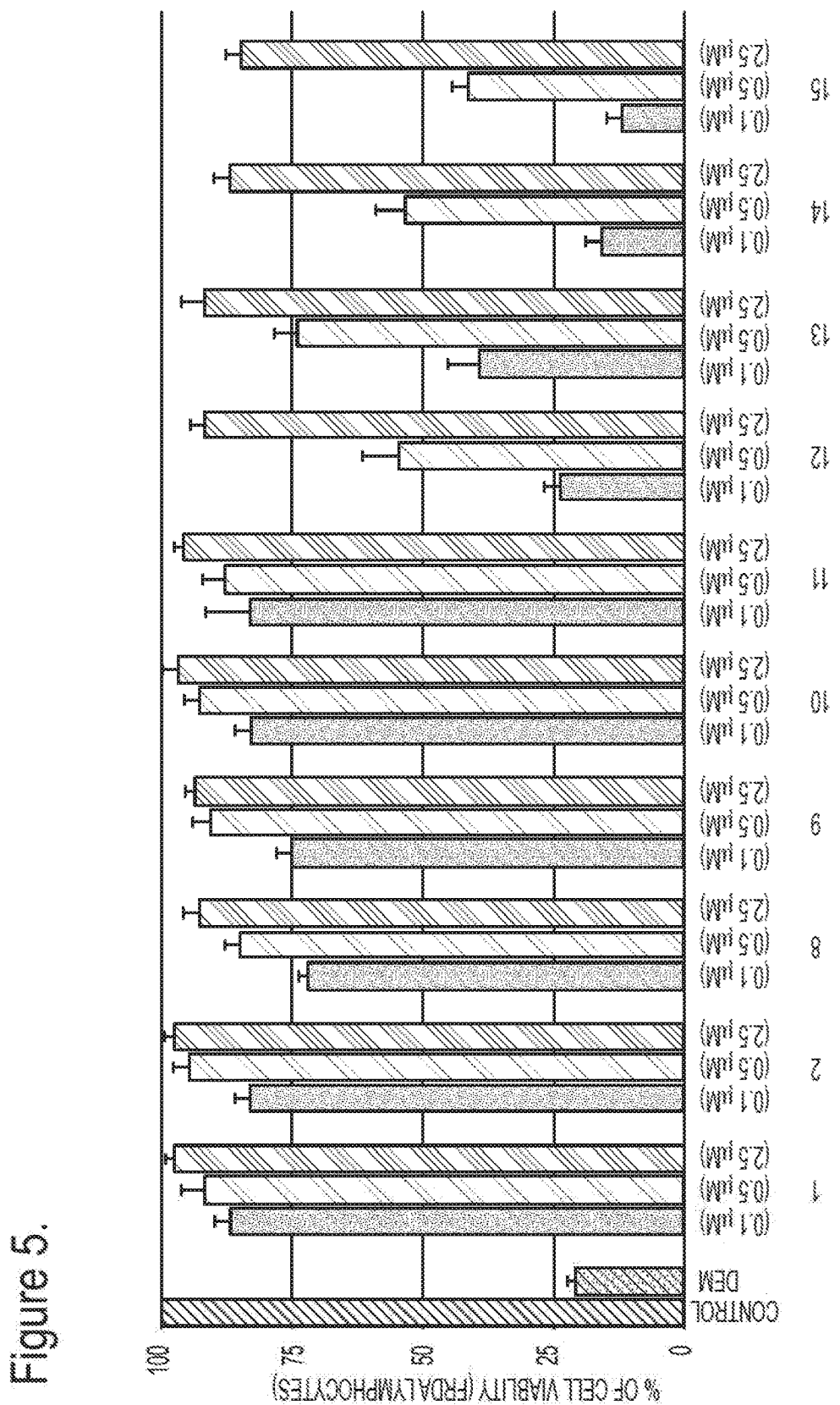
FIG. 5. Cell viability of Friedreich's ataxia lymphocytes following pretreatment with the test compounds for 16 h and then treatment with DEM (5 mM) for 6 h to induce oxidative stress. Flow cytometric determination of cell viability by fluorescence labeling was used employing calcein acetoxymethyl-ester and ethidium homodimer-1 (EthD-1) as live and dead cell stains.
Figure 6:
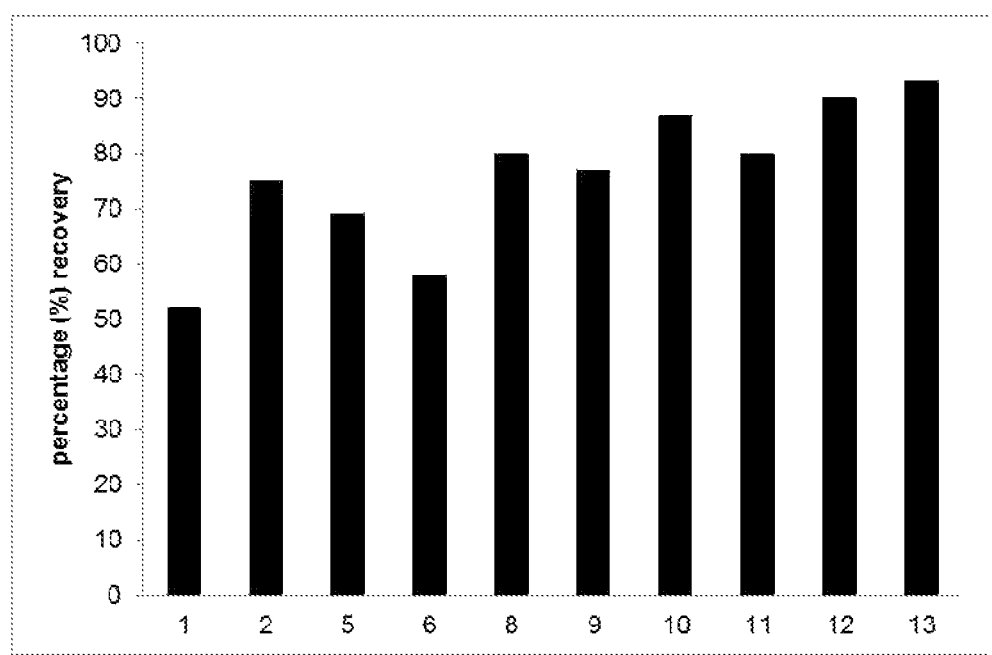
FIG. 6. Microsomal stability of the prepared compounds expressed as % of compound recovered after incubation with activated microsomes.

Provided herein are compounds (e.g., compounds of formula I or salts thereof) that are useful for the treatment or suppression of diseases associated with impaired mitochondrial function resulting in diminished ATP production and/or increased oxidative stress and/or lipid peroxidation. The compounds have been designed to include the properties of metabolic stability and bioavailability.

The compounds provided herein (e.g., compounds of formula I or salts thereof) include compounds that differ only in the presence of one or more isotopically enriched atoms. For example, compounds, wherein the independent replacement or enrichment of one or more hydrogen by deuterium or tritium, carbon by $^{13}$C- or $^{14}$C carbon, nitrogen by a $^{15}$N nitrogen, sulfur by a $^{33}$S, $^{34}$S or $^{36}$S sulfur, or oxygen by a $^{17}$O or $^{18}$O oxygen are included. Such compounds are useful, for example, as therapeutic agents, analytical tools or as probes in biological assays. In one embodiment, one or more hydrogens of the compound of formula I or a salt thereof are replaced by deuterium. In one embodiment, one or more carbons of the compound of formula I or a salt thereof is deuterated.

The following definitions are used, unless otherwise described.

The term "deuterated" means enriched in deuterium above its natural abundance at one or more positions of a compound. When a particular position, for example, a carbon atom, is deuterated, it is understood that the abundance of deuterium at that position is substantially greater than the natural abundance of deuterium, which is 0.015%. A deuterated position typically has a minimum isotopic enrichment factor of at least 3000 (45% deuterium incorporation).

The term "isotopic enrichment factor" as used herein means the ratio between the isotopic abundance and the natural abundance of a specified isotope. In certain embodiments, a compound has an isotopic enrichment factor of at least 3500 (52.5% deuterium incorporation) at a given deuterated atom, at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In some embodiments, 100% deuterium incorporation is achieved.

It is to be understood that a deuterated compound may contain one or more deuterium atoms. For example, a deuterated compound may contain just one deuterium. In some embodiments, a deuterated compound contains just two deuteriums. In some embodiments, a deuterated compound contains only three deuteriums. In some embodiments, a deuterated compound contains four deuteriums. In some embodiments, a deuterated compound contains 1, 2, 3, or 4 deuteriums. In some embodiments, a deuterated compound contains 1, 2, 3, or 4 or more deuteriums, or any range derivable therein. In some embodiments a carbon atom of a compound of formula I may be deuterated with a single deuterium. In some embodiments a carbon atom of a compound of formula I may be fully deuterated. The term fully deuterated refers to a carbon wherein each valence of the carbon that is not occupied by another atom is occupied by deuterium wherein the deuterium is enriched in deuterium above its natural abundance. It is to be understood that when a structure is shown herein with "D" it is a deuterium atom at that position that is enriched in deuterium above its natural abundance.

Deuterium can be incorporated into a compound of formula I using a variety of known reagents and synthetic techniques. For example, deuterium can be incorporated into a compound of formula I using a deuterated alkylating agent or a deuterio source. Deuterium can also be incorporated into a compound of formula I through other processes such as reduction, catalytic deuteration or isotopic exchange using appropriate deuterated reagents such as deuterides, $D_2$ and $D_2O$.

The compounds provided herein (e.g., compounds of formula I or salts thereof) also include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included.

The term "alkyl" as used herein is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms.

The term "alkenyl" as used herein is a straight or branched hydrocarbon with one or more carbon-carbon double bonds. For example, an alkenyl group can have 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=CH$_2$), allyl (—CH$_2$CH=CH$_2$) and 5-hexenyl (—CH$_2$CH$_2$CH$_2$CH$_2$CH=CH$_2$).

The term "alkynyl" as used herein is a straight or branched hydrocarbon with one or more carbon-carbon triple bonds. For example, an alkynyl group can have 2 to 8 carbon atoms (i.e. $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—CH$_2$C≡CH), and the like.

The term "halo" or "halogen" as used herein refers to fluoro, chloro, bromo and iodo.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e. ($C_3$-$C_7$)carbocycle). The term "carbocycle" or "carbocyclyl" also includes multiple condensed, saturated and partially unsaturated all carbon ring systems (e.g., ring systems comprising 2 or 3 carbocyclic rings). Accordingly, carbocycle includes multicyclic carbocyles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). The "carbocycle" or "carbocyclyl" can also be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g., ring systems comprising 2 or 3 rings) wherein a single heterocycle ring (as defined above) can be condensed with one or more groups selected from heterocycles (to form for example a decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one and pyrrolidin-2-one.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, 6 to 12 carbon atoms or 6-10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems may be optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Typical aryl groups include, but are not limited to, phenyl, indenyl, naphthyl, 1, 2, 3, 4-tetrahydronaphthyl, anthracenyl, and the like.

The term "treatment" or "treating," to the extent it relates to a disease or condition includes inhibiting the disease or condition, eliminating the disease or condition, and/or relieving one or more symptoms of the disease or condition.

The term "patient" as used herein refers to any animal including mammals such as humans, higher non-human primates, rodents domestic and farm animals such as cow, horses, dogs and cats. In one embodiment, the patient is a human patient.

The phrase "therapeutically effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific embodiments listed below for radicals, substituents, and ranges are for illustration only; they do not exclude other defined embodiments or values or other values within defined ranges for the radicals and substituents. It is to be understood that two or more embodiments may be combined.

In one embodiment $R^1$ is $(C_6-C_{26})$alkyl or $-O(C_6-C_{26})$alkyl wherein any $(C_6-C_{26})$alkyl of $R^1$ is optionally substituted with one or more groups independently selected from halogen, CN, $NO_2$, $-OR^{a1}$, $-N(R^{b1})_2$, $-CO_2R^{a1}$ and $-CON(R^{b1})_2$.

In one embodiment $R^1$ is $(C_6-C_{26})$alkyl wherein any $(C_6-C_{26})$alkyl of $R^1$ is optionally substituted with one or more groups independently selected from halogen, CN, $NO_2$, $-OR^{a1}$, $-N(R^{b1})_2$, $-CO_2R^{a1}$ and $-CON(R^{b1})_2$.

In one embodiment $R^1$ is $(C_{12}-C_{20})$alkyl wherein any $(C_{12}-C_{20})$alkyl of $R^1$ is optionally substituted with one or more groups independently selected from halogen, CN, $NO_2$, $-OR^{a1}$, $-N(R^{b1})_2$, $-CO_2R^{a1}$ and $-CON(R^{b1})_2$.

In one embodiment $R^1$ is $(C_{12}-C_{20})$alkyl.

In one embodiment $R^1$ is $-(CH_2)_{13}CH_3$, $-(CH_2)_{14}CH_3$ or $-(CH_2)_{15}CH_3$.

In one embodiment $R^{2a}$ and $R^{2b}$ are each independently $(C_1-C_6)$alkyl, wherein any $(C_1-C_6)$alkyl of $R^{2a}$ and $R^{2b}$ is optionally substituted with one or more groups independently selected from halogen, CN, $NO_2$, $-OR^{a2}$, $-N(R^{b2})_2$, $-CO_2R^{a2}$ and $-CON(R^{b2})_2$; or $R^{2a}$ and $R^{2b}$ together with the nitrogen to which they are attached form a 3-7 membered heterocyclyl wherein the heterocyclyl is optionally substituted with one more groups independently selected from halogen, $(C_1-C_6)$alkyl, $(C_2-C_6)$alkenyl, $(C_2-C_6)$alkynyl, CN, $NO_2$, $-OR^{a2}$, $-N(R^{b2})_2$, $-CO_2R^{a2}$ and $-CON(R^{b2})_2$;

In one embodiment $R^{2a}$ and $R^{2b}$ are each independently $(C_1-C_6)$alkyl; or $R^{2a}$ and $R^{2b}$ together with the nitrogen to which they are attached form a 3-7 membered heterocyclyl.

In one embodiment $-NR^{2a}R^{2b}$ is

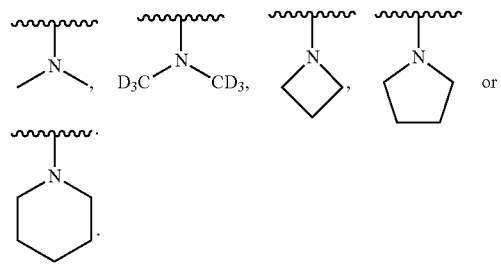

In one embodiment R³ is a carbocyclyl or —Ocarbocyclyl.

In one embodiment R³ is —Ocarbocyclyl, wherein any —Ocarbocyclyl of R³ is optionally substituted with one or more groups independently selected from halogen, CN, NO₂, —OR$^{a3}$, —N(R$^{b3}$)₂, —CO₂R$^{a3}$ and —CON(R$^{b3}$)₂.

In one embodiment R³ is —O(C₃-C₇)carbocyclyl wherein any —O(C₃-C₇)carbocyclyl is optionally substituted with one or more groups independently selected from halogen, CN, NO₂, —OR$^{a3}$, —N(R$^{b3}$)₂, —CO₂R$^{a3}$ and —CON(R$^{b3}$)₂.

In one embodiment wherein R³ is:

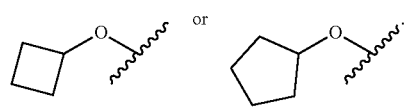

In one embodiment one or more carbons of the compound of formula I is deuterated.

In one embodiment R¹ is

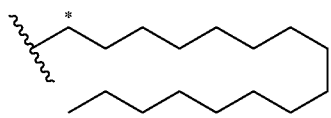 [SMILES: *CCCCCCCCCCCCCCCC]

wherein the carbon marked * is deuterated.
In one embodiment —NR$^{2a}$R$^{2b}$ is

wherein the carbons marked * are deuterated.
In one embodiment a compound of formula I is:

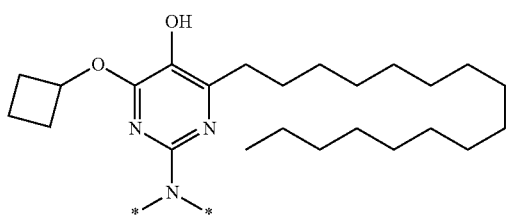 [SMILES: *N(*)c1nc(CCCCCCCCCCCCCCCC)c(O)c(OC2CCC2)n1]

or a salt thereof, wherein the carbons marked * are deuterated.

In one embodiment the deuterium of the deuterated carbon or deuterated carbons is enriched in deuterium with a minimum isotopic enrichment factor of at least 3000.

In one embodiment the carbon marked * is deuterated with one deuterium atom wherein the deuterium of the carbon marked * is enriched in deuterium with a minimum isotopic enrichment factor of at least 3000.

In one embodiment the deuterium of the deuterated carbon or deuterated carbons is enriched in deuterium over the natural abundance of deuterium for the corresponding non-deuterated carbon or carbons.

In one embodiment the carbon marked * is deuterated with one deuterium atom wherein the deuterium of the carbon marked * is enriched in deuterium above the natural abundance of deuterium for the corresponding non-deuterated carbon.

In one embodiment the carbon marked * is fully deuterated.

In one embodiment a compound of formula I is:

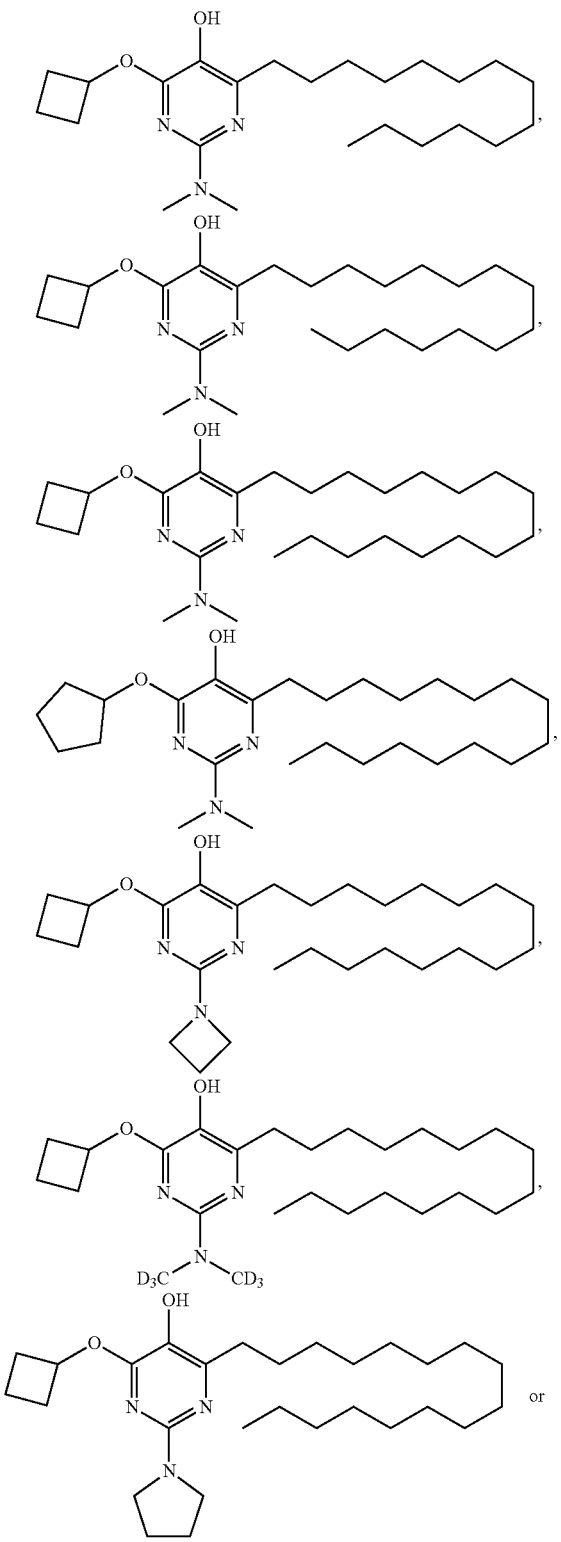

-continued

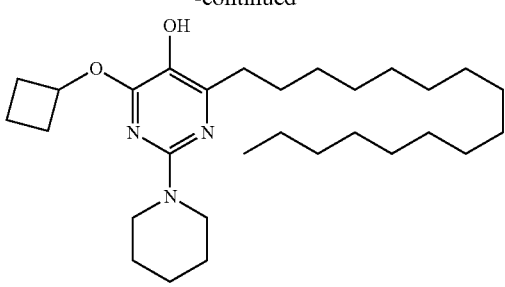

or a salt thereof.

One embodiment provides a compound which is:

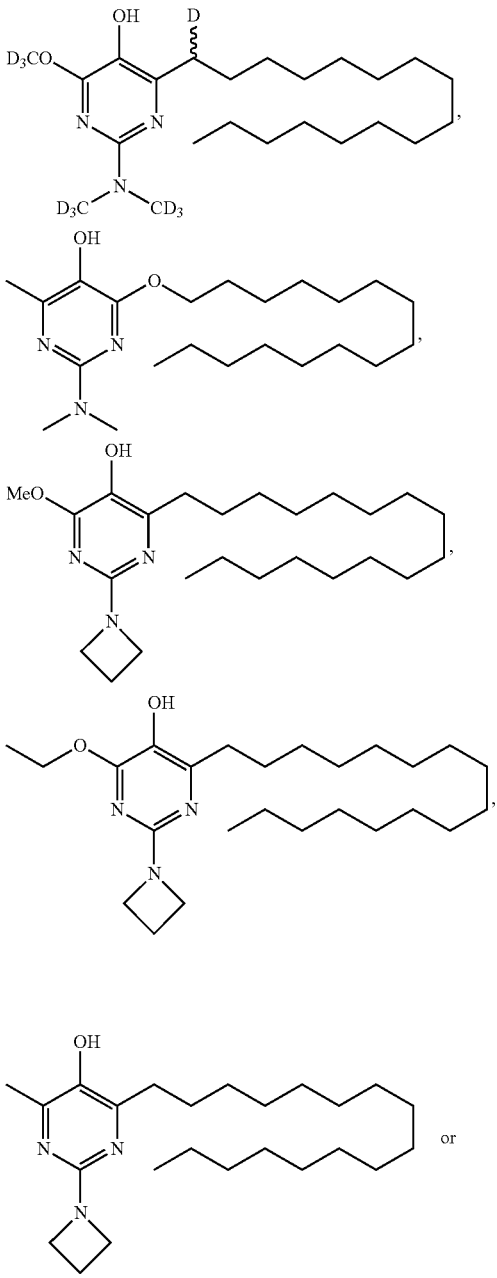

-continued

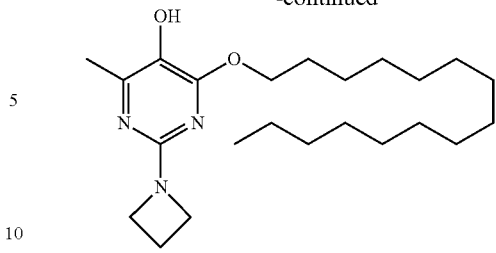

or a salt thereof.

In one embodiment the level of deuterium of the carbons bearing the deuterium is greater than the natural abundance of deuterium for the corresponding non-deuterated carbon.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts include organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic acid addition salts may also be formed, which include a physiological acceptable anion, for example, chloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of the compounds disclosed herein and one or more other active therapeutic agents are both present in the body of the patient.

In some embodiments, one or more of the compounds disclosed herein are co-administered with one or more active therapeutic agents by combining the compounds disclosed herein with the other therapeutic agents in a unitary dosage form for simultaneous or sequential administration to a patient. Thus, this combination therapy may be administered as a simultaneous or sequential regimen. When administered sequentially, the combination may be administered in two or more administrations.

Therapeutic Applications

Compounds disclosed herein are useful, for example, for treating or suppressing diseases associated with impaired mitochondrial function resulting in diminished ATP production and/or oxidative stress and/or lipid peroxidation in a subject in need of treatment. The present disclosure provides methods of treating a mitochondrial disease including but not limited to Friedreich's ataxia, Leber's hereditary optic neuropathy, Kearns-Sayre Syndrome, mitochondrial encephalomyopathy (e.g., with lactic acidosis and stroke-like episodes) and Leigh syndrome in an animal (e.g., a mammal such as a human).

The compounds disclosed herein are also useful for treating conditions including but not limited to obesity, atherosclerosis, Parkinson's disease, cancer, heart failure, myocardial infarction (MI), Alzheimer's disease, Huntington's disease, schizophrenia, bipolar disorder, fragile X syndrome and chronic fatigue syndrome, in an animal (e.g., a mammal such as a human).

One embodiment provides a method of treating a mitochondrial disease, obesity, heart disease, central nervous system disorder, cancer, fragile X syndrome or chronic fatigue syndrome in an animal (e.g., a mammal such as a human) comprising administering to the animal in need thereof a compound of formula I or a pharmaceutically acceptable salt as described herein.

One embodiment provides a method of treating a mitochondrial disease in an animal (e.g., a mammal such as a human) comprising administering to the animal in need thereof a compound of formula I or a pharmaceutically acceptable salt as described herein.

In one embodiment the mitochondrial disease is Friedreich's ataxia, Leber's hereditary optic neuropathy, Kearns-Sayre Syndrome, mitochondrial encephalomyopathy or Leigh syndrome.

One embodiment provides a method of treating a central nervous system disease in an animal (e.g., a mammal such as a human) comprising administering to the animal in need thereof a compound of formula I or a pharmaceutically acceptable salt as described herein.

In one embodiment the central nervous system disease is a neurodegenerative disease.

In one embodiment the neurodegenerative disease is Parkinson's Disease, Alzheimer's disease or Huntington's disease.

In one embodiment the central nervous system disease is schizophrenia or bipolar disorder.

One embodiment provides a method of treating heart disease in an animal (e.g., a mammal such as a human) comprising administering to the animal in need thereof a compound of formula I or a pharmaceutically acceptable salt as described herein.

In one embodiment the heart disease is atherosclerosis, heart failure or myocardial infarction.

Friedreich's ataxia is a severe neurodegenerative and cardiodegenerative condition. It is characterized by progressive ataxia of the limbs, muscle weakness, dysarthria, skeletal deformities and cardiomyopathy. While the biochemical basis of the disease is still under investigation, it is strongly associated with insufficient frataxin (Wilson et al. (1997) Nat. Genet. 16, 352-357; Wilson et al. (2003) J. Neurol. Sci. 207, 103-105). In the majority of patients the insufficiency of frataxin is a consequence of an intronic GAA triplet repeat expansion in the gene for frataxin, which results in a significant decrease in its mRNA levels, and ultimately in protein levels as well (Campuzano et al. (1996) Science 271, 1423-1427; Campuzano et al. (1997) Hum. Mol. Genet. 6, 1771-1780). Frataxin acts as an iron chaperone during heme biosynthesis (Bencze et al. (2007) J.C.S. Chem. Commun. 1798-1800) and has been shown to be capable of stimulating the in vitro assembly of heme and Fe—S clusters (Park et al. (2003) J. Biol. Chem. 278, 31340-31351; Yoon et al. (2003) J. Am Chem. Soc. 125, 6078-6084; Yoon et al. (2004) J. Biol. Chem. 279, 25943-25946). Frataxin can interact physically with mitochondrial electron transport chain proteins, as well as with mitochondrial aconitase (which contains an Fe—S cluster) (Bulteau et al. (2004) Science 305, 242-245; Gonzalez-Cabo et al. (2005) Hum. Mol. Genet. 14, 2091-2098). Therefore, frataxin deficiency results in disruption of cellular iron homeostasis, with a progressive iron accumulation in the mitochondrion, and a deficiency in heme and Fe—S clusters.

It is believed that a deficiency in frataxin leads to compromised mitochondrial respiratory chain function through a failure to assemble one or more Fe-utilizing proteins; one or more Fe—S clusters in the mitochondrial respiratory complexes are likely to represent a critical locus. In fact, diminished function of these complexes has been noted in Friedreich's ataxia patients (Bradley et al. (2000) Hum. Mol. Genet. 9, 275-282). The loss of mitochondrial respiratory chain function can lead to diminished ATP production, while the accumulation of Fe in the mitochondria makes the organelle highly susceptible to oxidative damage by reactive oxygen species, whose concentration increases concomitant with the decrease in respiratory chain function. There is compelling evidence that while oxidative damage is not the primary lesion in Friedreich's ataxia, oxidative stress helps to drive disease progression. Therefore, strategies to overcome oxidative stress should blunt disease progression and provide effective therapy.

Leber hereditary optic neuropathy is associated with degeneration of retinal ganglion cells and causes progressive loss of vision resulting in various degrees of blindness. Leber hereditary optic neuropathy primarily affects men over the age of 20 and is maternally transmitted due to mutations in the mitochondrial (not nuclear) genome.

Kearns-Sayre syndrome is a rare neuromuscular disorder typically with onset usually before the age of 20. It is characterized by progressive external ophthalmoplegia (paralysis of the eye muscles) and mild skeletal muscle weakness, hearing loss, loss of coordination, heart problems, and cognitive delays. There are many other names for the Kearns-Sayre syndrome including: Chronic progressive external ophthalmoplegia CPEO with myopathy; CPEO with ragged-red fibers; KSS; Mitochondrial cytopathy, Kearns-Sayre type; Oculocraniosomatic syndrome; Ophthalmoplegia-plus syndrome; Ophthalmoplegia with myopathy; and Ophthalmoplegia with ragged-red fibers.

Mitochondrial encephalomyopathy with lactic acidosis and stroke-like episodes is a progressive mitochondrial disease that involves multiple organ systems including the central nervous system, cardiac muscle, skeletal muscle, and gastrointestinal system. Symptoms include muscle weakness, stroke-like events, eye muscle paralysis, and cognitive impairment. Leigh syndrome is a degenerative brain disorder usually diagnosed at a young age (e.g. before age two). Deterioration is often rapid with symptoms such as seizures, dementia, feeding and speech difficulties, respiratory dysfunction, heart problems, and muscle weakness. Prognosis is poor with death typically occurring within a few years of diagnosis.

Mitochondrial Energy Production

Energy released from the citric acid (Krebs) cycle in the mitochondrial matrix enters the mitochondrial electron transport chain as NADH (complex I) and $FADH_2$ (complex II). These are the first two of five protein complexes involved in ATP production, all of which are located in the inner mitochondrial membrane. Electrons derived from NADH (by oxidation with a NADH-specific dehydrogenase) and $FADH_2$ (by oxidation with succinate dehydrogenase) travel down the respiratory chain, releasing their energy in discrete steps by driving the active transport of protons from the mitochondrial matrix to the intermembrane space (i.e., through the inner mitochondrial membrane).

The electron carriers in the respiratory chain include flavins, protein-bound iron-sulfur centers, quinones, cytochromes and copper. There are two molecules that transfer electrons between complexes: coenzyme Q (complex I→III, and complex II→III) and cytochrome c (complex III→IV). The final electron acceptor in the respiratory chain is $O_2$, which is converted to $H_2O$ in complex IV. In a functional mitochondrion, transport of two electrons through complex I results in the transport of $4H^+$ into the intermembrane space. Two more $H^+$ transfers to the intermembrane space result from electron transport through complex III, and four more $H^+$ transfers from electron transport through complex IV. The 10 protons transported to the intermembrane space create a proton electrochemical gradient; they can return to the mitochondrial matrix via complex V (ATP synthase), with the concomitant conversion of ADP to ATP. It is interesting that no $H^+$ is transferred to the intermembrane space as a consequence of electron transport through complex II. Therefore, $2e^-$ transfer from FADH2 (complex II→complex III→complex IV) results in the transport of only 6 protons, compared with 10 protons resulting from $2e^-$ transfer from NADH (complex I→complex III→complex IV), with correspondingly less ATP produced. Each glucose molecule metabolized by glycolysis produces 12 electrons; these are converted to 5 NADH molecules and 1 $FADH_2$ via the Krebs cycle in the mitochondrial matrix. The 5 NADH molecules employed in mitochondrial electron transport produce about 25 ATPs, while the single $FADH_2$ affords only about 3 ATP molecules. (There are another 4 molecules of ATP derived from glucose metabolism—2 during glycolysis and 2 in the Krebs cycle). While this analysis underscores the importance of complex I involvement in normal ATP production, it also tends to obscure certain metabolic realities/uncertainties that may offer important opportunities for therapeutic intervention. One metabolic reality is that complex I, while important quantitatively for ATP production in normal mitochondria, is not essential for all mitochondrial ATP production. Electrons can enter the electron transport chain at the level of coenzyme Q (either from complex II or from fatty acid oxidation), producing about 60% as much ATP as would have resulted had they entered the electron transport chain at complex I). While the flux of electrons that normally enter the individual mitochondrial complexes, ultimately passing through coenzyme Q, is probably dictated largely by the availability of electrons derived from NADH, $FADH_2$ and fatty acid oxidation, the actual intrinsic capacity of the individual pathways does not appear to have been studied carefully.

In functional mitochondria, a few experimental parameters can be measured readily, reflecting mitochondrial respiration. These include NADH and $O_2$ consumption, and ATP production. Less readily measured are the electrons that flow through the electron transport chain, thereby consuming oxygen, and producing $H_2O$ and ATP. The electrons within the mitochondria can really only be measured when they are associated with one of the mitochondrial electron carriers such as coenzyme Q. In humans, this mitochondrial coenzyme is present as coenzyme $Q_{10}$, which has a 50-carbon C-substituent that renders the molecule virtually insoluble in water (calculated octanol-water partition coefficient $>10^{20}$) (James et al. (2005) *J Biol. Chem.* 280, 21295-21312).

In dysfunctional mitochondria, one can still carry out the same types of measurements as noted above for functioning mitochondria. If the flow of electrons through complex I is interrupted, several measured parameters should change. These include diminished consumption of NADH (measured as increased lactate through pyruvate reduction) and diminished ATP production. Since electrons will not flow as efficiently from complex I to coenzyme Q, the concentration of this reduced coenzyme will diminish. Interestingly, a new pathway for oxygen consumption is created. While oxygen is not converted as efficiently to water in complex IV (an overall four electron reduction of each oxygen molecule), much of the flow of electrons into a defective complex I is redirected to oxygen, with the production of superoxide (a one electron reduction of each oxygen). Thus, the stoichiometry of oxygen utilization is altered. The production of superoxide by mitochondria actually occurs to some extent even in normal mitochondria, but is a much more frequent event in mitochondria containing defects in the respiratory chain. Superoxide is one form of reactive oxygen species (ROS). Superoxide itself is not believed to react readily with biological molecules such lipid membranes, proteins and DNA, and actually functions as a signaling molecule for the regulation of certain cellular processes. Biologically, the main fate of superoxide ($O_2.^-$) is a disproportionation reaction with itself to produce peroxide ($H_2O_2$) and oxygen, i.e.

$$2O_2^- + 2H^+ \rightarrow H_2O_2 + O_2$$

This reaction occurs spontaneously, and can also be catalyzed by superoxide dismutase. Superoxide can also be reduced to peroxide in a monovalent process. Like superoxide, hydrogen peroxide is also not intrinsically deleterious to cellular macromolecules, and is actually essential to the function of a number of enzymes. However, in the presence of metal ions such as iron and copper, hydrogen peroxide is converted to hydroxyl radical (HO.) and hydroxide ion ($OH^-$) according to the Fenton reaction, i.e.

$$HOOH + Fe^{2+} \rightarrow Fe^{3+} + HO. + OH^-$$

Hydroxyl radicals are very highly reactive, capable of reacting with virtually any biological molecule, including DNA, proteins and lipids. Hydroxyl radicals can also diffuse through cells readily, and their ability to damage cells is limited only by the distance that they travel before they react. Hydroxyl radicals can also react with superoxide, producing singlet oxygen (($^1O_2$)+$^-$OH), another highly reactive form of ROS that damages cellular macromolecules and assemblies. One particularly deleterious and well studied reaction mediated by hydroxyl radicals is the abstraction of hydrogen atoms (H.) from membrane lipids, forming a carbon-centered radical (R.). This radical $$HO. + RH(lipid) \rightarrow R^* + H_2O$$

$$R. + O_2 \rightarrow ROO.$$

$$ROO. + RH \rightarrow ROOH + R.$$

can readily react with oxygen, forming a hydroperoxy radical (ROO.). The hydroperoxy radical is also highly reactive, and can abstract another hydrogen atom from the membrane lipid, producing another carbon-centered radical (which can undergo precisely the same chemistry), ultimately producing a chain reaction affording many oxidative lesions in the membrane lipids from a single hydroxyl radical (lipid peroxidation). It is for this reason that lipid peroxidation likely represents a major process by which cellular and mitochondrial membranes are degraded in cells containing (partially) dysfunctional mitochondria. The observed accumulation of lipofuscin in Friedreich's ataxia patients is fully consistent with the thesis that lipid peroxidation is a central process that drives disease progression (La Marche et al. (1980) *Can. J. Neurosci.* 7, 389-396; Yin, D. (1996) *Free Rad. Biol. Med.* 21, 871-888; Yamada et al. (2001) *J. Lipid Res.* 42, 1187-1196). It may be noted that while all lesions in the mitochondrial electron transport chain that affect mitochondrial dysfunction will result in elevated levels of superoxide, some types of lesions may be expected to produce more functional damage. The latter would certainly include Friedreich's ataxia, in which suboptimal levels of the protein frataxin (which is responsible for cellular iron homeostasis; Park et al. (2003) *J. Biol. Chem.* 278, 31340-31351; Yoon et al. (2003) *J. Am. Chem. Soc.* 125, 6078-6084; Yoon et al. (2004) *J. Biol. Chem.* 279, 25943-25946; Bencze et al. (2007) *J.C.S. Chem. Commun.* 1798-1800) results in an accumulation of $Fe^{2+/3+}$ within the mitochondria, and contributes instead to the Fenton chemistry noted above. Likewise, disorders such as amyotrophic lateral sclerosis are associated with a deficiency in the detoxifying enzyme superoxide dismutase, and will have greatly enhanced concentrations of the ROS discussed above.

One poorly studied parameter of mitochondrial electron transport is whether the process is best characterized as involving one or two electron transfers. This is important because NADH is an obligatory two-electron donor, and coenzyme Q and cytochrome c participate in two-electron redox cycles, as does $FADH_2$. Virtually all publications represent the processes in which these species participate as involving a net two electron change. However, $FADH_2$ may (and generally does) transfer its reducing equivalents as single electrons. Further, the Q cycle in complex III clearly involves single-electron transfers. Reduced cytochrome c is known to transfer electrons one at a time to cytochrome c oxidase, the enzyme responsible for the final step in respiration. Finally, the accumulation of electrons within dysfunctional mitochondria (producing reductive stress) is relieved substantially by (one-electron) reduction of oxygen to superoxide (vide supra). Thus, while the electron transport chain has the capacity to transfer two electrons by virtue of the redox cycles of most of its participants, it is not clear that it necessarily must do so to function.

Given that the reductive stress (build-up of electrons) encountered initially in mitochondrial dysfunction is a one electron process, as is lipid peroxidation, carriers of single electrons could find utility in dealing with reductive stress, e.g. molecules in which the one-electron reduced intermediate is stabilized by dipole interactions, substituent effects, resonance effects or captodative effects. Molecules designed to traffic single electrons, and which can (i) accept electrons from superoxide (ii) donate electrons to complex III and (iii) quench carbon-centered lipid radicals are especially useful. Multifunctional Radical Quenchers (MRQs) of the invention can effectively protect mitochondria, cells and organisms from oxidative stress.

The compounds and methods of the disclosure are illustrated further by the following examples, which are provided for illustrative purposes and not intended to be construed as limiting the disclosure in scope or spirit to the specific compounds and methods described in them.

Methods of Synthesis

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

$^1$H-NMR spectra were recorded on a Varian Inova 500 MHz and 400 MHz, using chloroform-d. $^1$H-NMR chemical shifts were reported relative to residual $CHCl_3$ at 7.24 ppm. All solvents were analytical grade and were used without further purification. All chemicals were purchased from Aldrich Chemical Company and were used without further purification. The reactions were carried out under an atmosphere of argon unless specified otherwise. Column chromatography was carried out using silica gel (Silicycle R10030B, 60 particle size, 230-240 mesh). Analytical thin layer chromatography separations were carried out on glass plates coated with silica gel (60, particle size F254, E. Merck 5608/7). The TLC chromatograms were developed using UV (short wave) lamp irradiation or by immersing the plates in 2.5% potassium permanganate in ethanol or 2% anysaldehyde+5% sulfuric acid+1.5% of glacial acetic acid in ethanol fallowed by heating (heat gun).

Compound 1 was prepared by methods described in PCT/US2011/025613.

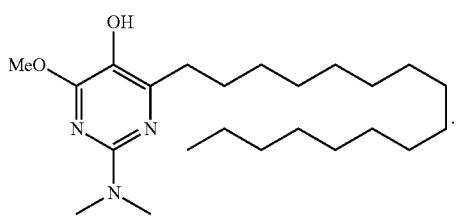

Example 1: Preparation of 2-(N,N-dimethylamino-$d_6$)-4-(1-hexadecyl-$d_1$)-6-(methoxy-$d_3$)-pyrimidin-5-ol (2)

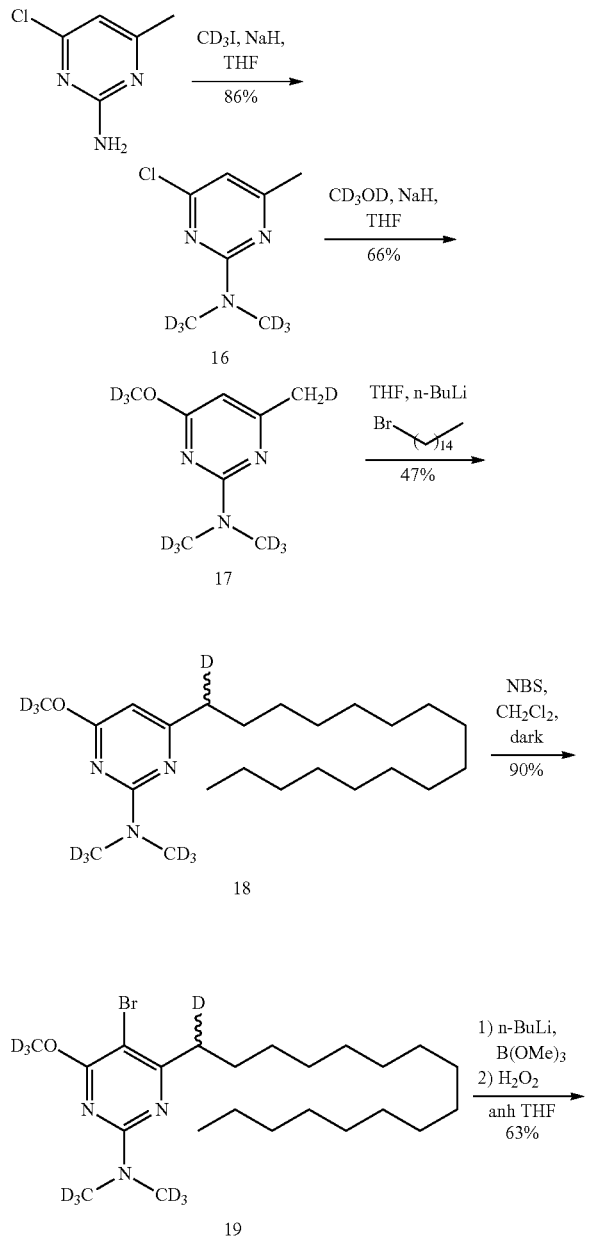

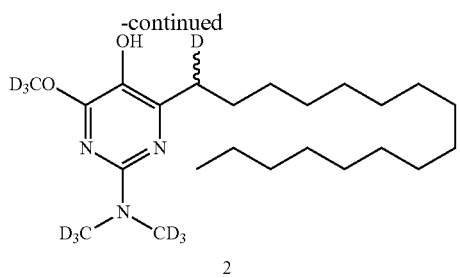

4-Chloro-6-methyl-(N,N-dimethylpyrimidin-2-amine-$d_6$) (16)

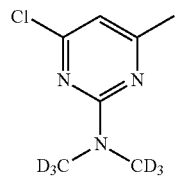 [SMILES: [2H]C([2H])([2H])N(c1nc(C)cc(Cl)n1)C([2H])([2H])[2H]]

To a stirred solution containing 500 mg (3.48 mmol) of 2-amino-4-chloro-6-methylpyrimidine and 435 µL (6.96 mmol) of methyl iodide-($d_3$) in 10 mL of anhydrous THF was added 417 mg (17.4 mmol) of NaH (60% suspension in oil) in two aliquots at 0° C. in the dark. The reaction mixture was slowly warmed to 23° C., stirred for 5 h under dark and then slowly poured into 100 mL of water. The crude was extracted with two 200-mL portions of EtOAc. The combined organic phase was washed with brine, dried (MgSO$_4$) and concentrated under diminished pressure. The residue was purified by chromatography on a silica gel column (15×3 cm). Elution with 9:1 hexane-EtOAc afforded 16 as a yellowish solid: yield 533 mg (86%); mp 29-30° C.; silica gel TLC R$_f$ 0.51 (4:1 hexane-EtOAc); $^1$H NMR (CDCl$_3$, 500 MHz) δ 2.19 (s, 3H) and 6.23 (s, 1H); $^{13}$C NMR (CDCl$_3$, 125 MHz) δ 23.9, 36.0, 107.2, 160.5, 161.9 and 168.8; mass spectrum (APCI), m/z 178.1017 (M+H)$^+$ (C$_7$H$_5$N$_3$$^2$H$_6$Cl requires 178.1018).

4-(Methoxy-$d_3$)-6-(methyl-$d_1$)-(N,N-dimethylpyrimidin-2-amine-$d_6$) (17)

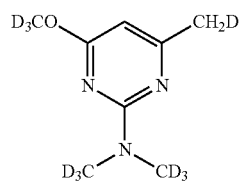

To a stirred solution containing 530 mg (2.98 mmol) of 16 in 10 mL of anhydrous THF was added 430 mg (17.9 mmol) of NaH (60% suspension in oil) and 244 µL (5.96 mmol) of CD$_3$OD. The reaction mixture was stirred at reflux for 20 h and then allowed to cool to room temperature. The mixture was slowly poured into 200 mL of water and extracted with two 300-mL portions of EtOAc. The combined organic phase was washed with brine, dried (MgSO$_4$) and concentrated under diminished pressure. The residue was purified by chromatography on a silica gel column (20×3 cm). Elution with hexane followed by 97:3 hexane-EtOAc afforded 17 as a colorless oil: yield 350 mg (66%); silica gel TLC $R_f$ 0.25 (7:1 hexane-EtOAc); $^1$H NMR (CDCl$_3$, 400 MHz) δ 2.23 (m, 2H) and 5.77 (s, 1H); $^{13}$C NMR (CDCl$_3$, 100 MHz) δ 24.2, 36.0, 52.0, 93.8, 162.4, 167.8 and 170.3; mass spectrum (APCI), m/z 178.1762 (M+H)$^+$ ($C_8H_4N_3O^2H_{10}$ requires 178.1765).

4-(Methoxy-d$_3$)-6-(1-hexadecyl-d$_1$)-(N,N-dimethyl-pyrimidin-2-amine-d$_6$) (18)

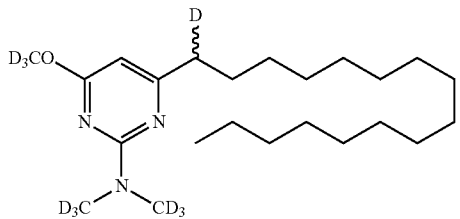

To a stirred solution containing 240 mg (1.36 mmol) of 17 in 15 mL of anhydrous THF at −78° C. was added 817 μL (2.04 mmol) of a 2.5 M solution of n-BuLi in hexane. The reaction mixture was stirred at −78° C. for 20 min and then 355 μL (1.22 mmol) of 1-bromopentadecane was added. The reaction was stirred at 0° C. for 15 min and then at room temperature for another 30 min. The reaction mixture was quenched with satd aq ammonium chloride and extracted with 150 mL of EtOAc. The combined organic phase was washed with brine, dried (MgSO$_4$) and concentrated under diminished pressure. The residue was purified by chromatography on a silica gel column (30×3 cm). Elution with 19:1 hexane-Et$_2$O afforded 18 as a colorless solid: yield 250 mg (47%); mp 45-46° C.; silica gel TLC $R_f$ 0.58 (4:1 hexane-Et$_2$O); $^1$H NMR (CDCl$_3$, 400 MHz) δ 0.88 (t, 3H, J=6.8 Hz), 1.19-1.37 (m, 26H), 1.64 (m, 2H), 2.48 (q, 1H, J=8.0 Hz) and 5.79 (s, 1H); $^{13}$C NMR (CDCl$_3$, 100 MHz) δ 14.2, 22.8, 28.6, 29.4, 29.5, 29.52, 29.7, 29.73, 29.8, 29.9, 32.1, 36.0, 37.6, 38.0, 52.0, 93.2, 162.5, 170.4 and 171.9; mass spectrum (FAB), m/z 388.4117 (M+H)$^+$ ($C_{23}H_{34}N_{32}H_{10}O$ requires 388.4112).

3-Bromo-4-(methoxy-d$_3$)-6-(1-hexadecyl-d$_1$)-(N,N-dimethylpyrimidin-2-amine-d$_6$) (19)

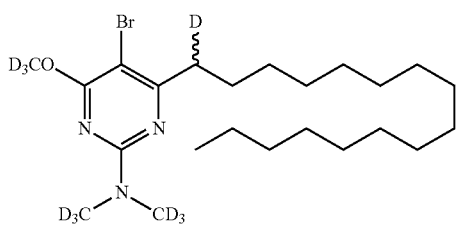

To a stirred solution containing 320 mg (0.83 mmol) of 18 in 10 mL CH$_2$Cl$_2$ was added 154 mg (0.87 mmol) of NBS under dark. The reaction mixture was stirred for 30 min at room temperature under dark, then diluted with CH$_2$Cl$_2$, washed with brine, dried (MgSO$_4$) and concentrated under diminished pressure. The residue was purified by chromatography on a silica gel column (15×3 cm). Elution with hexane followed by 19:1 hexane-EtOAc afforded 19 as a colorless solid: yield 159 mg (90%); mp 63-64° C.; silica gel TLC $R_f$ 0.31 (19:1 hexane-EtOAc); $^1$H NMR (CDCl$_3$, 400 MHz) δ 0.88 (t, 3H, J=7.2 Hz), 1.19-1.40 (m, 26H), 1.66 (m, 2H) and 2.69 (q, 1H, J=7.6 Hz); $^{13}$C NMR (CDCl$_3$, 100 MHz) δ 14.3, 22.8, 27.7, 29.5, 29.6, 29.63, 29.7, 29.8, 29.9, 32.1, 36.5, 36.9, 53.3, 91.3, 160.3, 165.2 and 169.2; mass spectrum (APCI), m/z 468.3208 (M+H) ($C_{23}H_{33}N_3O_2H_{10}{}^{81}Br$ requires 468.3197).

2-(N,N-dimethylamino-d$_6$)-4-(1-hexadecyl-d$_1$)-6-(methoxy-d$_3$)-pyrimidin-5-ol (2)

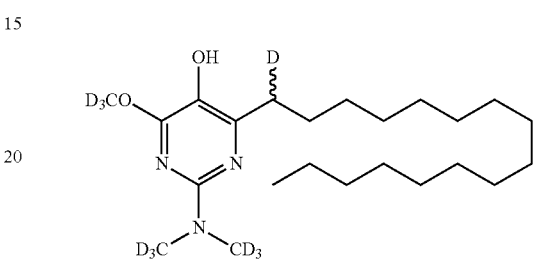

To a stirred solution containing 276 mg (0.59 mmol) of 19 in 10 mL of anhydrous THF at −5° C. was added 473 μL (1.18 mmol) of a 2.5 M solution of n-BuLi in hexane and 197 μL (1.77 mmol) of trimethoxyborane. The reaction mixture was stirred at 23° C. for 30 min followed by addition of 883 μL (12.9 mmol) of H$_2$O$_2$ (50% v/v). The reaction mixture was stirred for additional 30 min, poured into 20 mL NaHCO$_3$ and then extracted with 100 mL of CH$_2$Cl$_2$. The combined organic phase was washed with brine, dried (MgSO$_4$) and concentrated under diminished pressure. The residue was purified by chromatography on a silica gel column (20×3 cm). Elution with 95:5 hexane-EtOAc afforded 2 as a colorless powder: yield 150 mg (63%); mp 75-76° C.; silica gel TLC $R_f$ 0.38 (4:1 hexane-EtOAc); $^1$H NMR (CDCl$_3$, 400 MHz) δ 0.88 (t, 3H, J=7.2 Hz), 1.19-1.39 (m, 26H), 1.65 (m, 2H), 2.60 (m, 1H) and 4.50 (br s, 1H); $^{13}$C NMR (CDCl$_3$, 100 MHz) δ 14.3, 22.8, 27.9, 29.5, 29.6, 29.7, 29.72, 29.8, 29.82, 29.9, 32.1, 54.4, 127.1, 155.1, 156.1 and 158.2; mass spectrum (APCI), m/z 404.4067 (M+H)$^+$ ($C_{23}H_{34}N_3O_{22}H_{10}$ requires 404.4061).

Example 2: Preparation of 4-cyclobutoxy-2-(dimethylamino)-6-tetradecylpyrimidin-5-ol (3)

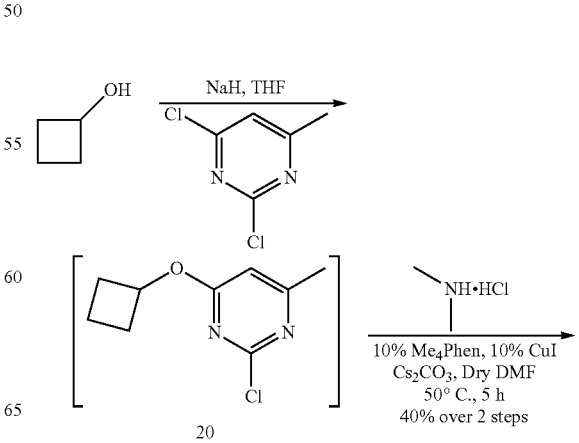

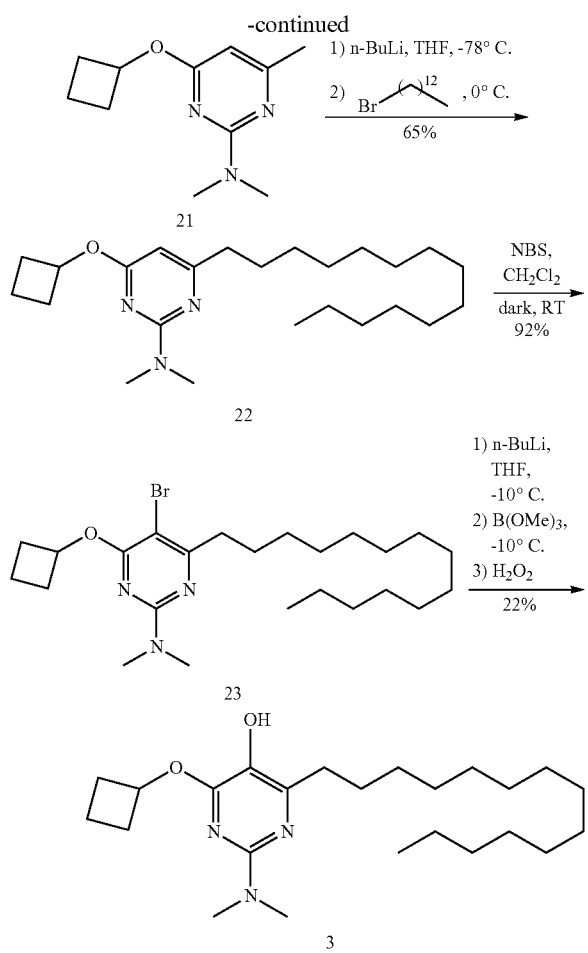

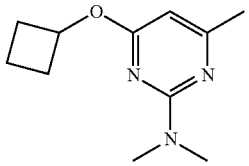

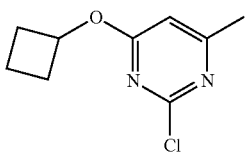

2-chloro-4-cyclobutoxy-6-methylpyrimidine (20)

To a stirred solution of cyclobutanol 1.4 g (19.4 mmol) in 100 mL of freshly distilled THF under argon was slowly added 1.55 g (38.8 mmol) of NaH (60% in paraffin) and The reaction mixture was stirred at room temperature for 30 min. The resulting reacting mixture was cooled at 0° C. and 3 g (18.48 mmol) of the 2,4-dichloro-6-methylpyrimidine in solution in 10 mL of distilled THF was added dropwise. The reaction was warmed to room temperature and kept under argon for 4 h. After the reaction was completed, the mixture was slowly poured into 100 mL of deionized water. The aqueous layer was extracted with three portions of 100 mL of EtOAc. The organic phases were combined, dried over MgSO$_4$ and evaporated to dryness under diminished pressure. The crude mixture was recovered as a yellowish oil and directly used for the next step. Mass spectrum (MALDI), m/z 199.0816 (M+H)$^+$ (C$_9$H$_{11}$ClN$_2$O requires m/z 198.056).

4-Cyclobutoxy-2-(N, N-dimethylamino)-6-methylpyrimidine (21)

To a solution of 400 mg (1.80 mmol) of crude 20 in 2 mL of DMF was added 13.0 mg (0.06 mmol) of 3,4,7,8-tetramethyl-1,10-phenanthroline, 10.0 mg (0.06 mmol) of dimethylamine HCl salt 137 mg (1.69 mmol), Cs$_2$CO$_3$ 641 mg (1.90 mmol) in ice. The reaction mixture was stirred for 5 h at 50° C. The reaction mixture was then diluted with 5 mL of water and extracted with seven 2-mL portions of dichloromethane. The organic layer was washed with water, brine and dried (Na$_2$SO$_4$). The excess solvent was concentrated under diminished pressure to afford a crude. The crude was purified by flash column chromatography on a silica gel column (24×2 cm). Elution with 1:5 ethyl acetate/hexane gave 21 as a colorless oil: yield 125 mg (40%); silica gel TLC Rf 0.30 (1:2 ethyl acetate/hexanes); $^1$H NMR (CDCl$_3$) δ 1.63-1.65 (m, 1H), 1.66-1.80 (m, 1H), 2.08-2.14 (m, 4H) 2.14 (s, 3H), 2.35-2.43 (m, 3H), 3.11 (m, 6H), 5.06-5.09 (m, 1H); $^{13}$CNMR (CDCl$_3$) δ 14.0, 23.8, 23.9, 24.1, 32.7, 32.8, 32.8, 36.8, 94.5, 164.6, 167.5 and 169.6; mass spectrum (APCI), m/z 222.1987 (M+H)+ (C$_{12}$H$_{20}$ClN$_3$O requires m/z 222.1987).

4-Cyclobutoxy-N,N-dimethyl-6-tetradecylpyrimidin-2-amine (22)

To a solution containing 200 mg (0.96 mmol) of 4-cyclobutoxy-N,N,6-trimethylpyrimidin-2-amine 21 in 4 mL dry THF was slowly added 1.22 mL (1.6 M in Hexanes, 2.17 mmol) of n-butyllithium dropwise at −78° C. The reaction mixture is warmed to 0° C. over 2 h, 0.7 mL (0.7 g, 2.75 mmol) of purified 1-bromotridecane added and the reaction mixture stirred at room temperature under an atmosphere of argon for 3 h. The reaction mixture was quenched with 20 mL of saturated NH$_4$Cl and extracted with five 10 mL portions of diethyl ether. The organic layer was washed with distilled water, brine and dried over MgSO$_4$. The excess solvent was concentrated under diminished pressure to afford a crude residue. The crude residue was applied to a silica gel column (6×3 cm). Elution with 1:9 ethyl acetate-hexanes afforded 22 as a colorless solid: yield 135 mg (65%); silica gel TLC Rf 0.45 (1:1 ethyl ether/hexanes); $^1$H NMR (CDCl$_3$) δ 0.84-0.87 (t, 3H, J=7.2 Hz), 1.28 (m, 23H), 1.60-1.76 (m, 2H), 1.78-1.83 (q, 1H, J=10 Hz), 2.07-2.14 (q, 2H, J=10 Hz), 2.36-2.40 (m, 2H), 2.44-2.48 (t, 2H, J=8 Hz), 3.12 (s, 6H), 5.07-5.13 (q, 1H, J=8 Hz), 6.40 (s, 1H); $^{13}$C NMR (CDCl$_3$) δ 14.1, 14.5, 23.1, 28.9, 29.7, 29.8, 29.9, 30.0, 30.1, 30.1, 31.1, 32.3, 37.2, 38.3, 70.2, 93.6, 162.6, 169.5 and 172.4; mass spectrum (APCI), m/z 390.3486 (M+H)+ (C$_{24}$H$_{44}$N$_3$O requires m/z 390.3484).

5-Bromo-4-cyclobutoxy-2-(N,N-dimethylamino)-6-tetradecylpyrimidine (23)

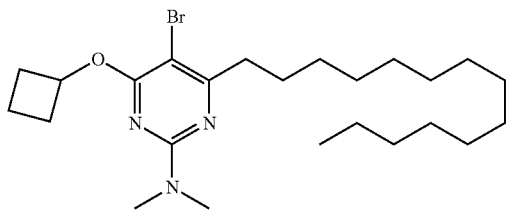 [SMILES: CCCCCCCCCCCCCCc1nc(N(C)C)nc(OC2CCC2)c1Br]

To a solution containing 150 mg (0.38 mmol) of 22 in 5.00 mL of freshly distilled dichloromethane was slowly added 71.0 mg (0.40 mmol) of recrystallised N-bromosuccinimide at 0° C. The reaction mixture was stirred at room temperature under an atmosphere of argon for 15 min. The reaction mixture was quenched with 20 mL of saturated NH$_4$Cl and extracted with three 10-mL portions of diethyl ether. The organic layer was successively washed with distilled water, brine and dried (MgSO$_4$). The excess solvent was concentrated under diminished pressure to afford a crude residue. The crude residue was applied to a silica gel column (6×3 cm). Elution with 1:20 ethyl acetate/hexanes afforded 23 as a colorless solid: yield 165 mg (92%); silica gel TLC R$_f$ 0.45 (1:10 ethyl ether/hexanes); $^1$H NMR (CDCl$_3$) δ 0.84-0.87 (t, 3H, J=7.2 Hz), 1.28 (m, 23H), 1.60-1.76 (m, 2H), 1.78-1.83 (q, 1H, J=10 Hz), 2.07-2.14 (q, 2H, J=10 Hz), 2.36-2.40 (m, 2H), 2.44-2.48 (t, 2H, J=8 Hz), 3.12 (s, 6H), 5.07-5.13 (q, 1H, J=8 Hz); $^{13}$C NMR (CDCl$_3$) δ 22.6, 24.9, 27.6, 29.1, 29.3, 29.3, 29.3, 29.4, 29.4, 29.5, 29.5, 29.6, 29.6, 29.7, 29.8, 29.8, 29.8, 30.5, 30.5, 30.6, 31.8, 35.9, 36.7, 36.7, 36.7, 36.8, 36.8, 36.9, 36.9, 36.9, 51.1, 70.9, 90.5, 160.1, 164.9 and 168.9; mass spectrum (APCI), m/z 468.5265 (M+H)+ (C$_{24}$H$_{43}$BrN$_3$O$_2$ requires m/z 468.5259).

4-Cyclobutoxy-2-(N,N-dimethylamino)-6-tetradecylpyrimidin-5-ol (3)

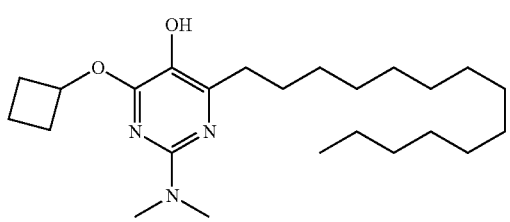 [SMILES: CCCCCCCCCCCCCCc1nc(N(C)C)nc(OC2CCC2)c1O]

To a stirred solution containing 120 mg (0.25 mmol) of 23 at −5° C. in 3.00 mL dry THF was added 390 μL (0.62 mmol) of N-butyllithium dropwise over 5 min. The mixture was stirred for 20 minutes. To the mixture was added 84.0 μL (78.0 mg, 0.75 mmol) of trimethyl borate and stirred for 1 h. To the reaction mixture was added 0.55 mL of 30% aq H$_2$O$_2$. The reaction mixture was then stirred for 30 min and poured into water. The reaction mixture was quenched with 20 mL of saturated NH$_4$Cl and extracted with five 10-mL portions of ethyl acetate. The organic layer was washed with distilled water, brine and dried (MgSO$_4$). The excess solvent was concentrated under diminished pressure to afford a crude residue. The crude residue was applied to a silica gel column (6×3 cm). Elution with 1:4 ethyl acetate/hexanes afforded 3 as a colorless solid: yield 22 mg (22%); silica gel TLC R$_f$ 0.3 (1:1 ethyl ether/hexanes); $^1$H NMR (CDCl$_3$) δ 0.84-0.87 (t, 3H, J=7.2 Hz), 1.28 (m, 24H), 1.60-1.76 (m, 2H), 1.78-1.83 (q, 1H, J=10 Hz), 2.07-2.14 (q, 2H, J=10 Hz), 2.36-2.40 (m, 2H), 2.44-2.48 (t, 2H, J=8 Hz), 3.12 (s, 6H), 5.07-5.13 (q, 1H, J=8 Hz); $^{13}$C NMR (CDCl$_3$) δ 13.5, 14.1, 22.6, 28.4, 29.3, 29.3, 29.4, 29.5, 29.6, 29.6, 29.7, 29.7, 29.7, 30.6, 31.9, 37.07, 38.7, 68.1, 128.7, 156.6, 156.9 and 157.1; mass spectrum (APCI), m/z 406.3454 (M+H)+ (C$_{24}$H$_{44}$N$_3$O$_2$ requires m/z 406.3434).

Example 3: Preparation of 4-cyclobutoxy-2-(dimethylamino)-6-pentadecylpyrimidin-5-ol (4)

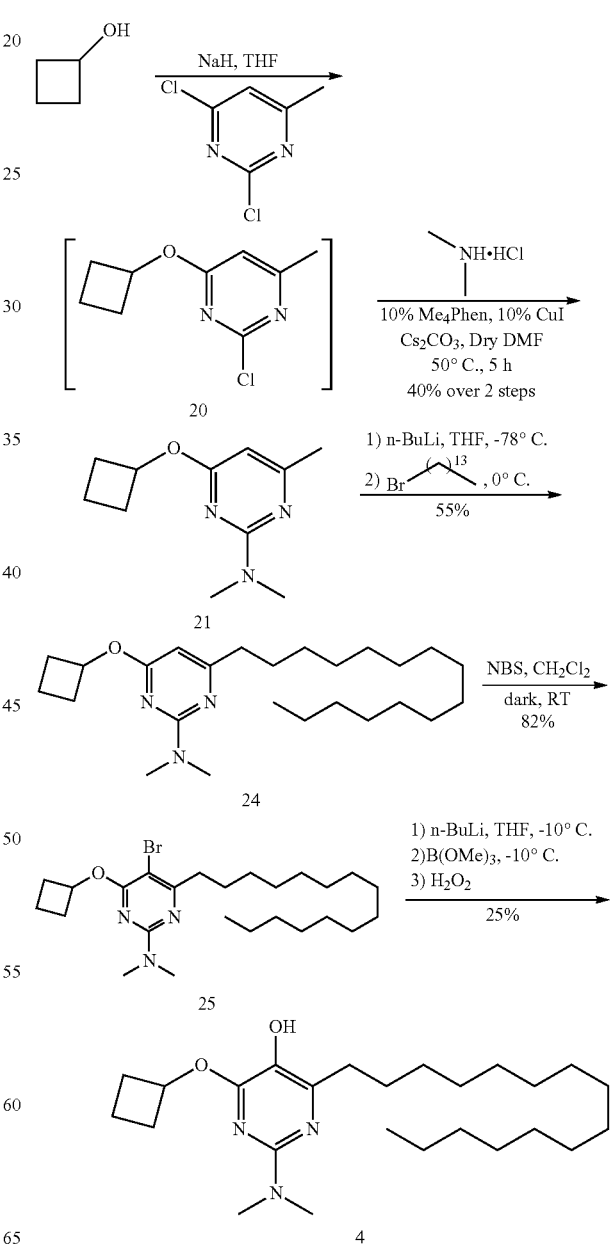

4-Cyclobutoxy-2-(N,N-dimethylamino)-6-pentadecylpyrimidine (24)

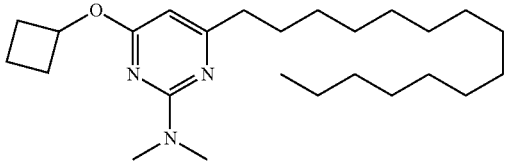 [SMILES: CCCCCCCCCCCCCCCc1cc(OC2CCC2)nc(N(C)C)n1]

To a solution containing 148 mg (0.71 mmol) of 21 in 4.00 mL dry THF was added 0.80 mL (1.6 M in hexanes, 1.08 mmol) of n-butyllithium dropwise at −78° C. The reaction mixture was kept at −78° C. for 1 h, then 0.40 mL (0.47 g, 1.70 mmol) of purified 1-bromotetradecane was added and the reaction mixture stirred at room temperature under an atmosphere of argon for 3 h. The reaction mixture was quenched with 20 mL of saturated NH$_4$Cl and extracted with five 10-mL portions of diethyl ether. The organic layer was washed successively with distilled water, brine and dried (MgSO$_4$). The excess solvent was concentrated under diminished pressure. The crude was applied to a silica gel column (6×3 cm). Elution with 1:9 ethyl acetate/hexanes afforded 24 as a colorless solid: yield 158 mg (55%); silica gel TLC R$_f$ 0.45 (1:1 ethyl ether/hexanes); $^1$H NMR (CDCl$_3$) δ 0.84-0.87 (t, 3H, J=7.2 Hz), 1.28 (m, 25H), 1.60-1.76 (m, 2H), 1.78-1.83 (q, 1H, J=10 Hz), 2.07-2.14 (q, 2H, J=10 Hz), 2.36-2.40 (m, 2H), 2.44-2.48 (t, 2H, J=8 Hz), 3.12 (s, 6H), 5.07-5.13 (q, 1H, J=8 Hz), 6.40 (s, 1H); $^{13}$C NMR (CDCl$_3$) δ 14.0, 14.5, 23.1, 28.9, 29.7, 29.8, 29.9, 30.01, 30.1, 30.1, 31.1, 32.3, 37.2, 38.3, 70.2, 93.6, 162.6, 169.5 and 172.4; mass spectrum (APCI), m/z 404.5158 (M+H)$^+$ (C$_{25}$H$_{46}$N$_3$O requires m/z 404.5155).

5-Bromo-4-cyclobutoxy-(N,N-dimethylamino)-6-pentadecylpyrimidine (25)

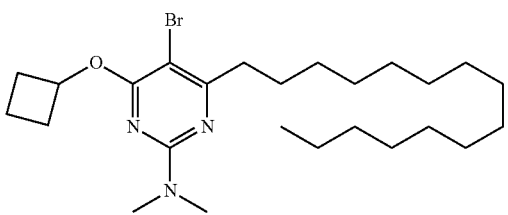 [SMILES: CCCCCCCCCCCCCCCc1nc(N(C)C)nc(OC2CCC2)c1Br]

To a solution containing 120 mg (0.30 mmol) of 4-cyclobutoxy-N,N-dimethyl-6-ridecylpyrimidin-2-amine 24 in 5.00 mL of freshly distilled dichloromethane was added 53.3 mg (0.30 mmol) of recrystallized N-Bromosuccinimide slowly at 0° C. The reaction mixture was stirred at room temperature under an atmosphere of argon for 1 h. The reaction mixture was quenched with 20 mL of saturated NH$_4$Cl and extracted with three 10-mL portions of diethyl ether. The organic layer was washed successively with distilled water, brine and dried (MgSO$_4$). The excess solvent was concentrated under diminished pressure. The crude was applied to a silica gel column (6×3 cm). Elution with 1:20 ethyl acetate/hexanes afforded 25 as a colorless solid: yield 116 mg (82%); silica gel TLC R$_f$ 0.45 (1:10 ethyl ether/hexanes); $^1$H NMR (CDCl$_3$) δ 0.84-0.87 (t, 3H, J=7.2 Hz), 1.28 (m, 25H), 1.60-1.76 (m, 2H), 1.78-1.83 (q, 1H, J=10 Hz), 2.07-2.14 (q, 2H, J=10 Hz), 2.36-2.40 (m, 2H), 2.44-2.48 (t, 2H, J=8 Hz), 3.12 (s, 6H), 5.07-5.13 (q, 1H, J=8 Hz); $^{13}$C NMR (CDCl$_3$) δ 14.1, 22.7, 27.6, 29.3, 29.4, 29.4, 29.5, 29.6, 30.6, 31.9, 36.8, 36.9, 71.0, 91.2, 160.0, 164.1 and 169.0; mass spectrum (APCI), m/z 482.2746 (M+H)$^+$ (C$_{25}$H$_{45}$BrN$_3$O$_2$ requires m/z 482.2746).

4-Cyclobutoxy-2-(dimethylamino)-6-pentadecylpyrimidin-5-ol (4)

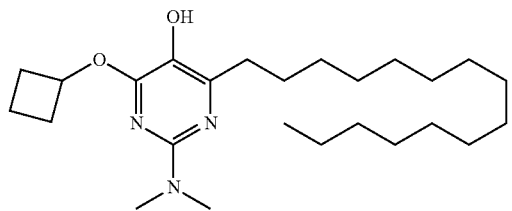 [SMILES: CCCCCCCCCCCCCCCc1nc(N(C)C)nc(OC2CCC2)c1O]

To a stirred solution containing 100 mg (0.21 mmol) of compound 25 at −5° C. in 3.00 mL dry THF was added 390 μL (1.6 M in hexanes, 0.62 mmol) of n-butyllithium dropwise over 5 min. The mixture was stirred for 20 min. To the mixture was added 84.0 μL (78.0 mg, 0.75 mmol) of trimethyl borate and was stirred for 1 h. To the reaction mixture was added 0.55 mL of 30% aq H$_2$O$_2$. The reaction mixture was then stirred for 30 min and poured into water. The reaction mixture was quenched with 20 mL of saturated NH$_4$Cl and extracted with five 10-mL portions of ethyl acetate. The organic layer was washed successively with distilled water, brine and dried (MgSO$_4$). The excess solvent was concentrated under diminished pressure to afford a crude. The crude was applied to a silica gel column (6×3 cm). Elution with 1:4 ethyl acetate/hexanes afforded 4 as a colorless solid: yield 21 mg (25%); silica gel TLC R$_f$ 0.3 (1:1 ethyl ether/hexanes); $^1$H NMR (CDCl$_3$) δ 0.84-0.87 (t, 3H, J=7.2 Hz), 1.28 (m, 25H), 1.60-1.76 (m, 2H), 1.78-1.83 (q, 1H, J=10 Hz), 2.07-2.14 (q, 2H, J=10 Hz), 2.36-2.40 (m, 2H), 2.44-2.48 (t, 2H, J=8 Hz), 3.12 (s, 6H), 5.07-5.13 (q, 1H, J=8 Hz), 6.40 (s, 1H); $^{13}$C NMR (CDCl$_3$) δ13.5, 14.0, 14.1, 22.7, 22.9, 23.7, 27.7, 28.9, 29.3, 29.5, 29.6, 29.6, 29.7, 29.8, 30.3, 30.8, 31.9, 37.3, 37.3, 38.7, 68.1, 126.8, 153.9, 154.6, 156.2; mass spectrum (APCI), m/z 420.4413, (M+H)$^+$ (C$_{25}$H$_{46}$N$_3$O$_2$ requires m/z 420.4410).

Example 4: Preparation of 4-cyclobutoxy-2-(dimethylamino)-6-hexadecylpyrimidin-5-ol (5)

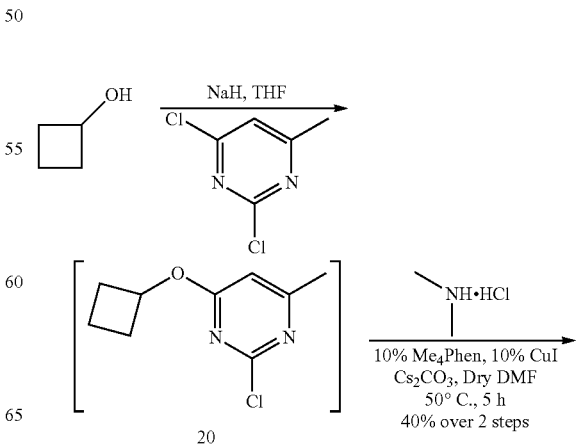

-continued

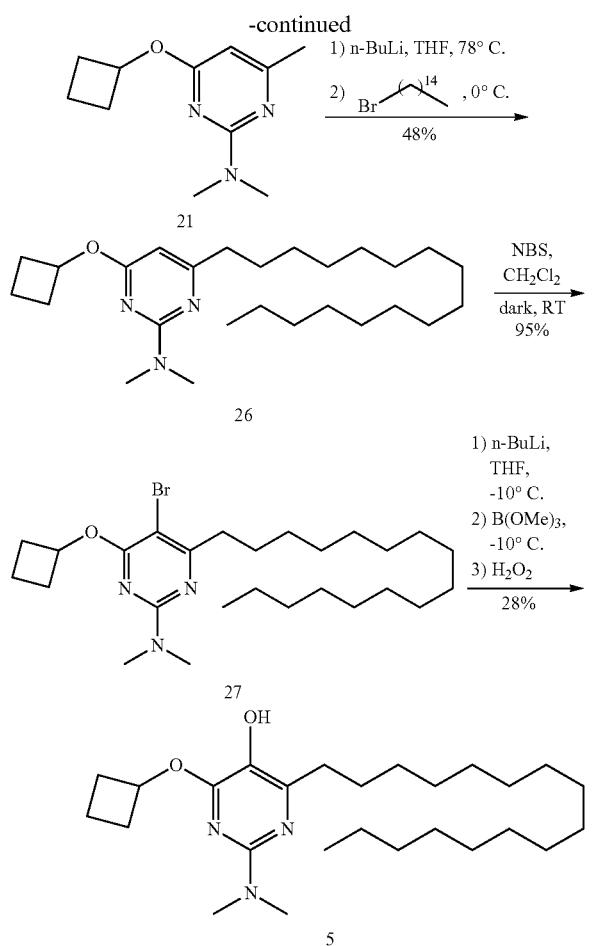

To a stirred solution containing 933 mg (5.58 mmol) of 21 in 10.0 mL of freshly distilled THF at −78° C. under inert atmosphere was added 5.23 mL (8.37 mmol) of 1.6 M n-BuLi in hexanes. The reaction mixture was stirred at −78° C. for 1 h. 0.55 mL (0.57 g, 2.10 mmol) of purified 1-bromopentadecane was added and The reaction was warmed to room temperature then kept under stirring for 30 more min. The reaction mixture was quenched with NH$_4$Cl$_{Sat}$ and poured into 100 mL of water. The compound was extracted with two 80-mL portions of ethyl acetate. The combined organic layer was washed with 80 mL of brine, dried (MgSO$_4$) and concentrated under diminished pressure. The residue was purified by chromatography on a silica gel column (15×5 cm). Elution with 9:1 hexanes-ethyl acetate afforded compound 26 as a colorless solid: yield 902 mg (48%); silica gel TLC R$_f$ 0.45 (9:1 hexanes-ethyl acetate);

$^1$H NMR (CDCl$_3$) δ 0.87 (t, 3H, J=7.2 Hz), 1.25-1.32 (m, 27H), 1.63-1.65 (m, 1H), 1.66-1.80 (m, 1H), 2.08-2.14 (m, 2H) 2.14 (s, 3H), 2.35-2.43 (m, 3H), 3.11 (m, 6H), 5.06-5.09 (m, 1H); $^{13}$C NMR (CDCl$_3$) δ 13.9, 14.5, 23.1, 28.9, 29.7, 29.8, 29.9, 30.0, 30.1, 30.1, 31.1, 32.3, 37.2, 38.3, 70.2, 93.6, 162.6, 169.5 and 172.4; mass spectrum (APCI), m/z 418.3800 (M+H)$^+$ (C$_{26}$H$_{48}$ClN$_3$O requires m/z 418.3797).

5-Bromo-4-cyclobutoxy-2-(N,N-dimethylamino)-6-hexadecylpyrimidine (27)

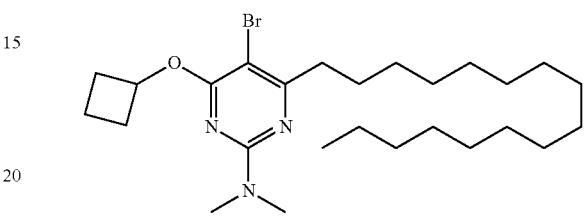

To a solution of 60.0 mg (0.17 mmol) of compound 26 in 3.00 mL of freshly distilled CH$_2$Cl$_2$ was added 43.6 mg (0.25 mmol) of recrystallized N-bromosuccinimide at 0° C. The reaction mixture was stirred for 2 h at room temperature. The reaction mixture was then diluted with 5 mL of water and extracted trice with 10-mL portions of dichloromethane. The organic layer was washed successively with water, brine and dried over MgSO$_4$. The excess solvent was concentrated under diminished pressure to afford a crude residue. The residue was purified by flash column chromatography on a silica gel column (24×2 cm). Elution with 1:5 ethyl acetate/hexane gave 27 as a colorless solid: yield, 68 mg (95%); silica gel TLC R$_f$ 0.30 (1:2 ethyl acetate/hexanes); $^1$H NMR (CDCl$_3$) δ 0.87 (t, 3H, J=7.2 Hz), 1.25-1.32 (m, 27H), 1.63-1.65 (m, 1H), 1.66-1.80 (m, 1H), 2.08-2.14 (m, 2H) 2.14 (s, 3H), 2.35-2.43 (m, 3H), 3.11 (m, 6H); $^{13}$C NMR (CDCl$_3$) δ13.5, 14.0, 22.6, 27.4, 27.6, 29.0, 29.2, 29.3, 29.3, 29.4, 29.5, 29.6, 29.6, 30.6, 31.9, 35.9, 36.7, 36.9, 70.9, 91.27 160.0, 164.1 and 168.9; mass spectrum (APCI), m/z 496.2911 (M+H)$^+$ (C$_{26}$H$_{47}$BrN$_3$O requires m/z 496.2902).

4-cyclobutoxy-2-(N,N-dimethylamino)-6-hexadecylpyrimidin-5-ol (5)

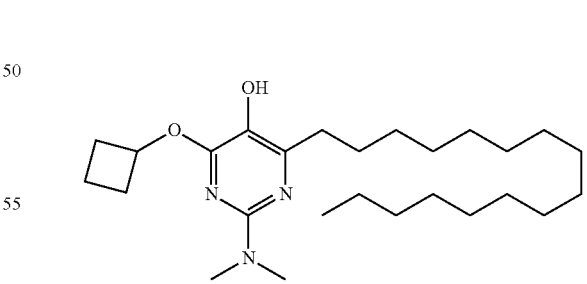

To a stirred solution at −5° C. containing 81.0 mg (0.19 mmol) of compound 27 in 3.00 mL of anh THF was added 300 μL (0.47 mmol) of 1.6 M solution of n-BuLi in hexanes. The reaction mixture was stirred at −5° C. for 20 min. To the mixture was added 64.0 μL (60.0 mg; 0.57 mmol) of trimethyl borate and the reaction mixture was stirred for 1 h. To the reaction mixture was added 0.42 mL of 30% aq H$_2$O$_2$ followed by 0.13 mL of 3 N aq NaOH. The reaction mixture was stirred for 30 min and poured into 15 mL of water. The aq mixture was neutralized with dilute aq HCl and extracted with two 5-mL portions of ethyl acetate. The combined organic solution was washed successively with 8 mL of brine and distilled water, dried (MgSO$_4$). The excess solvent was concentrated under diminished pressure. The residue was purified by chromatography on a silica gel column (10×3 cm). Elution with 2:1 hexanes-ethyl acetate afforded compound 2-(dimethylamino)-4-methyl-6-(pentadecyloxy) pyrimidin-5-ol 5 as a colorless solid: yield 19 mg (28%); silica gel TLC R$_f$ 0.3 (1:1 ethyl ether/hexanes) $^1$H NMR (CDCl$_3$) δ 0.87 (t, 3H, J=7.2 Hz), 1.25-1.32 (m, 25H), 1.51 (s, 3H), 1.62-1.74 (m, 2H), 1.72-1.83 (q, 1H, J=10 Hz), 2.07-2.14 (q, 2H, J=10 Hz), 2.34-2.39 (m, 2H), 2.44-2.43 (t, 2H, J=8 Hz), 3.10 (s, 6H), 4.09 (br s, 1H); $^{13}$C NMR (CDCl$_3$) δ 13.5, 14.1, 22.6, 28.4, 29.3, 29.5, 29.5, 29.6, 29.6, 30.7, 30.8, 31.9, 37.2, 70.5, 126.8, 151.2, 154.8 and 158.5; mass spectrum (APCI), m/z 434.3739 (M+H)$^+$ (C$_{26}$H$_{48}$N$_3$O$_2$ requires m/z 434.3747).

Example 5: Preparation of 2-(dimethylamino)-4-methyl-6-(pentadecyloxy) pyrimidin-5-ol (6)

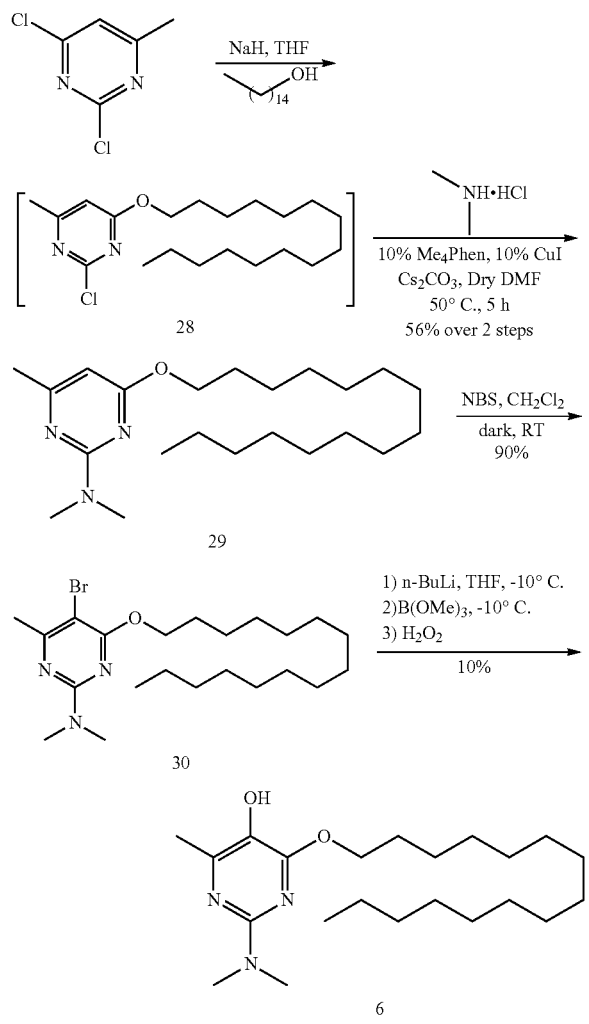

2-Chloro-4-methyl-6-(pentadecyloxy)-pyrimidine (28)

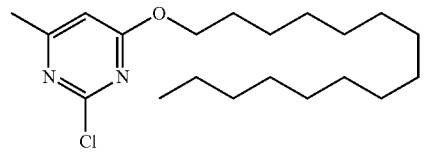 [SMILES: CCCCCCCCCCCCCCCOc1cc(C)nc(Cl)n1]

To a solution of 699 mg (3.07 mmol) of 1-pentadecanol and 147 mg (6.12 mmol) NaH in 6 mL of THF was added 500 mg (3.07 mmol) of 2,4-dichloro-6-methylpyrimidine in ice. The reaction mixture was stirred for 27 h at room temperature. The reaction mixture was then diluted with 5 mL of water and extracted with three 10-mL portions of dichloromethane. The organic layer was washed with water, brine and dried (MgSO$_4$). The excess solvent was concentrated under diminished pressure to afford crude residue 28 as a yellow oil. The crude material (28) was used directly in the next step.

4-Methyl-2-(N,N-dimethylamino)-6-(pentadecyloxy) pyrimidine (29)

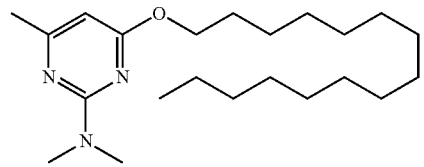 [SMILES: CCCCCCCCCCCCCCCOc1cc(C)nc(N(C)C)n1]

To a solution of 200 mg (0.56 mmol) of crude 28 in 2 mL of DMF at 0° C. was added 13.0 mg (0.06 mmol) of 3,4,7,8-tetramethyl-1,10-phenanthroline, 11.0 mg (0.06 mmol) of CuI, 37 (1.69 mmol) of dimethylamine hydrochloride, and 641 mg (1.90 mmol) of cesium carbonate. The reaction mixture was stirred for 5 h at 50° C. The reaction mixture was then diluted with 5 mL of water and extracted with seven 2-mL portions of dichloromethane. The organic layer was washed successively with water, brine and dried (Na$_2$SO$_4$). The excess solvent was concentrated under diminished pressure to afford a crude residue. The residue was purified by flash column chromatography on a silica gel column (24×2 cm). Elution with 1:5 ethyl acetate-hexane gave 29 as a colorless solid: yield—633 mg (56%); silica gel TLC R$_f$ 0.30 (1:2 ethyl acetate-hexanes); $^1$H NMR (CDCl$_3$) δ 0.87 (t, 3H, J=7.2 Hz), 1.25-1.32 (m, 26H), 1.51 (s, 3H), 2.01 (s, 6H), 4.09 (t, 2H, J=6.8 Hz) and 5.25 (s, 1H); $^{13}$C NMR (CDCl$_3$) δ14.2, 22.7, 24.5, 26.0, 28.7, 28.8, 29.4, 29.4, 29.5, 29.5, 29.5, 29.6, 29.6, 29.7, 29.7, 29.8, 29.8, 29.9, 29.9, 29.9, 30.0, 30.0, 32.0, 32.7, 37.1, 37.1, 67.1, 94.9, 162.8, 166.6 and 169.8 mass spectrum (APCI), m/z 364.5510 (M+H)$^+$ (C$_{22}$H$_{42}$ClN$_3$O requires m/z 364.5508).

5-Bromo-4-methyl-2-(N,N-dimethylamino)-6-(pentadecyloxy)pyrimidine (30)

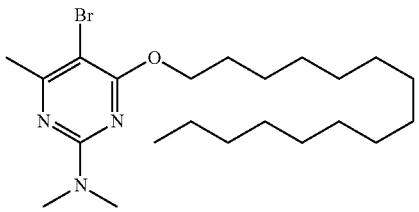

To a solution of 60.0 mg (0.17 mmol) of 29 in 3.00 mL of CH$_2$Cl$_2$ was added 44.0 mg (0.25 mmol) recrystallized N-bromosuccinimide at 0° C. The reaction mixture was stirred for 2 h at room temperature. The reaction mixture was then diluted with 5 mL of water and extracted with two 10-mL portions of dichloromethane. The organic layer was washed successively with water, brine and dried (MgSO$_4$). The excess solvent was concentrated under diminished pressure to afford a crude. The residue was purified by flash column chromatography on a silica gel column (24×2 cm). Elution with 1:5 ethyl acetate-hexane gave 30 as a colorless solid: yield 65 mg (90%); silica gel TLC R$_f$ 0.30 (1:2 ethyl acetate-hexanes); $^1$H NMR (CDCl$_3$) δ 0.87 (t, 3H, J=7.2 Hz), 1.25-1.32 (m, 26H), 1.51 (s, 3H), 2.01 (s, 6H), 4.09 (t, 2H, J=6.8 Hz); $^{13}$C NMR (CDCl$_3$) δ 14.2, 22.7, 24.5, 26.0, 28.7, 28.8, 29.4, 29.4, 29.5, 29.5, 29.5, 29.6, 29.6, 29.7, 29.7, 29.8, 29.8, 29.9, 29.9, 29.9, 30.0, 30.0, 32.0, 32.7, 37.1, 37.1, 67.1, 91.9, 159.9, 164.9 and 165.6; mass spectrum (APCI), m/z 442.5002 (M+H) (C$_{22}$H$_{41}$BrN$_3$O requires m/z 442.5002).

4-Methyl-2-(N,N-dimethylamino)-6-(pentadecyloxy)pyrimidin-5-ol (6)

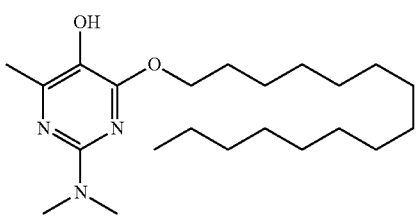 [SMILES: CCCCCCCCCCCCCCCOc1nc(N(C)C)nc(C)c1O]

To a stirred solution at −5° C. containing 93.0 mg (0.23 mmol) of compound 30 in 3.0 mL of anh THF was added 362 μL (0.57 mmol) of 1.6 M solution of n-BuLi in hexanes. The reaction mixture was stirred at −5° C. for 20 min. To the reaction mixture was added 81.0 μL (72.0 mg; 0.69 mmol) of trimethyl borate and the reaction mixture was stirred for 1 h. To the reaction mixture was added 0.51 mL of 30% aq H$_2$O$_2$. The reaction mixture was stirred for 30 min and poured into 50 mL of water. The aq. mixture was neutralized with dilute aq. HCl and extracted with two 50-mL portions of ethyl acetate. The combined organic solution was washed successively with 80 mL of brine and 125 distilled water and dried (MgSO$_4$). The excess solvent was concentrated under diminished pressure. The residue was purified by chromatography on a silica gel column (10×3 cm). Elution with 2:1 hexanes-ethyl acetate afforded compound 6 as colorless solid: yield 7.9 mg (10%); silica gel TLC R$_f$ 0.3 (1:1 ethyl ether-hexanes) $^1$H NMR (CDCl$_3$) δ 0.87 (t, 3H, J=7.2 Hz), 1.2-1.32 (m, 26H), 1.51 (s, 3H), 2.01 (s, 6H), 4.09 (t, 2H, J=6.8 Hz), 5.09 (br s, 1H); $^{13}$C NMR (CDCl$_3$) δ14.7, 22.6, 24.5, 26.2, 28.7, 28.8, 29.4, 29.4, 29.5, 29.5, 29.5, 29.6, 29.6, 29.7, 29.7, 29.8, 29.8, 29.9, 29.9, 29.9, 30.0, 30.0, 32.0, 32.7, 37.1, 37.1, 65.1, 129.9, 155.3, 154.8 and 157.2; mass spectrum (APCI), m/z 380.4944 (M+H)+ (C$_{22}$H$_{42}$N$_3$O$_2$ requires m/z 380.4940).

Example 6: Preparation of 4-(cyclopentyloxy)-2-(N,N-dimethylamino)-6-hexadecylpyrimidin-5-ol (7)

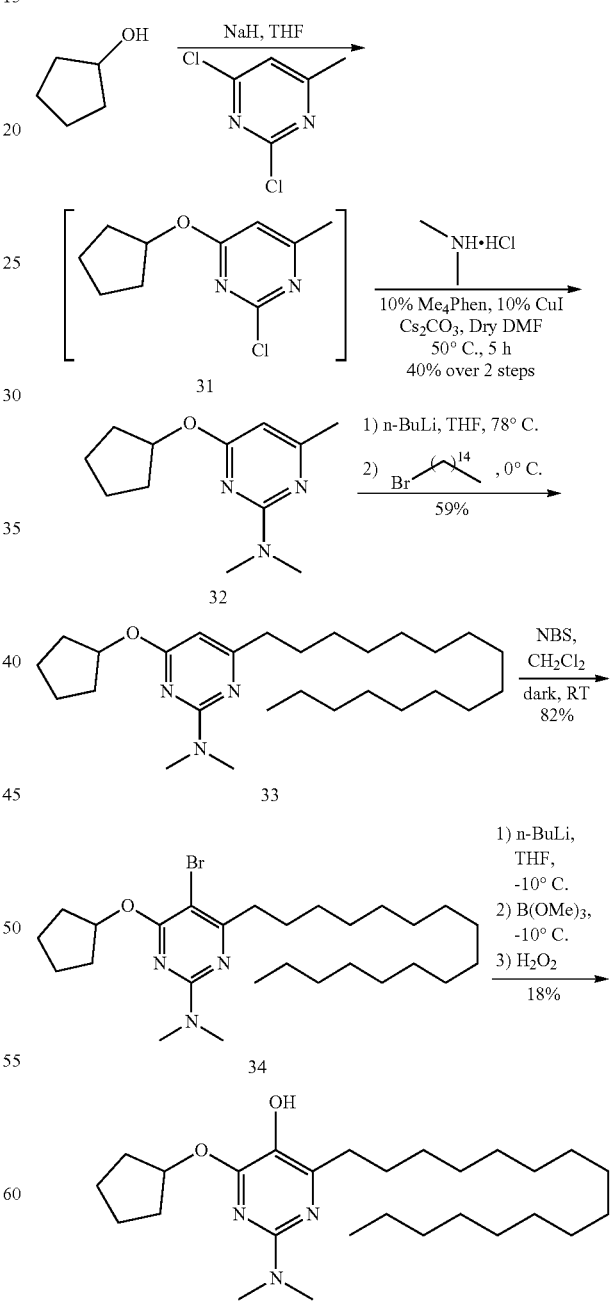

2-Chloro-4-(cyclopentyloxy)-6-methylpyrimidine (31)

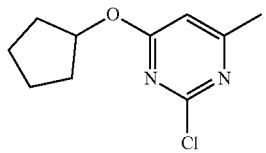

To a stirred solution of cyclopentanol 1.67 g (19.4 mmol) in 100 mL of freshly distilled THF under argon was slowly added 1.55 g (38.8 mmol) of NaH (60% in paraffin) and the reaction mixture was stirred at room temperature for 30 min. The resulting reacting mixture was cooled at 0° C. and 3 g (18.48 mmol) of the 2,4-dichloro-6-methylpyrimidine in solution in 10 mL of distilled THF was added dropwise. The reaction was warmed to 50° C. and kept under argon for 12 h. After The reaction was completed, the mixture was slowly poured into 100 mL of deionized water. The aqueous layer was extracted with three portions of 100 mL of Ethyl Acetate. The organic phases were combined, dried over MgSO$_4$ and evaporated to dryness under diminished pressure. The crude 31 was recovered as a yellowish oil and directly used for the next step.

4-(Cyclopentyloxy)-2-(N,N-dimethylamino)-6-methylpyrimidine (32)

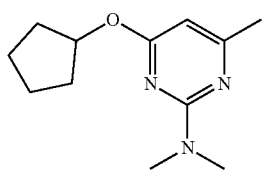 [SMILES: Cc1cc(OC2CCCC2)nc(N(C)C)n1]

To a solution of 400 mg (1.80 mmol) of crude mixture 31 in 2 mL of DMF at 0° C. was added 13.0 mg (0.06 mmol) of 3,4,7,8-tetramethyl-1,10-phenanthroline, 11 mg (0.06 mmol) of CuI, 137 mg (1.69 mmol) of dimethylamine hydrochloride salt, and 641 mg (1.90 mmol) of cesium carbonate. The reaction mixture was stirred for 5 h at 50° C. The reaction mixture was then diluted with 5 mL of water and extracted with seven 2-mL portions of dichloromethane. The organic layer was washed with water, brine and dried (Na$_2$SO$_4$). The excess solvent was concentrated under diminished pressure to afford a crude. The crude was purified by flash column chromatography on a silica gel column (24×2 cm). Elution with 1:5 ethyl acetate/hexane gave 32 as a colorless oil: yield 125 mg (40%); silica gel TLC R$_f$ 0.30 (1:2 ethyl acetate/hexanes); $^1$H NMR (CDCl$_3$) δ 1.63-1.65 (m, 1H), 1.66-1.80 (m, 1H), 2.08-2.14 (m, 4H) 2.14 (s, 3H), 2.35-2.43 (m, 3H), 3.11 (m, 6H), 5.06-5.09 (m, 1H); $^{13}$C NMR (CDCl$_3$) δ 14.0, 23.8, 23.9, 24.1, 32.7, 32.8, 32.8, 36.8, 94.5, 164.6, 167.5 and 169.6; mass spectrum (APCI), m/z 222.1987 (M+H)$^+$ (C$_{12}$H$_{20}$ClN$_3$O requires m/z 222.1987).

4-(Cyclopentyloxy)-2-(N,N-dimethylamino)-6-hexadecylpyrimidine (33)

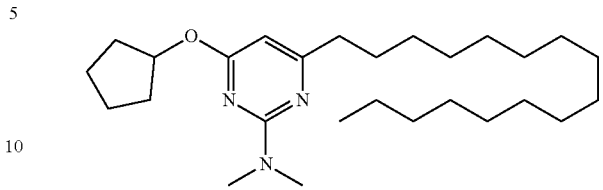

To a stirred solution containing 633 mg (2.86 mmol) of compound 32 in 6.00 mL anh THF at −78° C. was added 1.79 mL (8.37 mmol) of 1.6 M n-BuLi in hexanes. The reaction mixture was stirred at −78° C. for 20 min. 1.20 mL (4.10 mmol) 1-bromopentadecane was added to the mixture. The reaction was then stirred at 0° C. for 1 h. The reaction mixture was quenched with saturated aqueous ammonium chloride and poured into 100 mL of water. The compound was extracted with two 80-mL portions of ethyl acetate. The combined organic layer was washed successively with 80 mL of brine, dried (MgSO$_4$) and concentrated under diminished pressure. The residue was purified by chromatography on a silica gel column (15×5 cm). Elution with 9:1 hexanes-ethyl acetate afforded compound 33 as a colorless solid: yield 735 mg (59%); silica gel TLC R$_f$ 0.45 (9:1 hexanes-ethyl acetate); $^1$H NMR (CDCl$_3$) δ 0.87 (t, 3H, J=7.2 Hz), 1.25-1.32 (m, 27H), 1.63-1.65 (m, 1H), 1.66-1.80 (m, 1H), 2.08-2.14 (m, 4H) 2.14 (s, 3H), 2.35-2.43 (m, 3H), 3.11 (m, 6H), 5.06-5.09 (m, 1H); $^{13}$C NMR (CDCl$_3$) δ14.1, 22.6, 24.0, 28.4, 29.3, 29.4, 29.5, 29.6, 29.6, 29.7, 31.9, 32.8, 36.8, 50.25, 93.8, 163.3, 169.6 and 172.7; mass spectrum (APCI), m/z 432.3955 (M+H)$^+$ (C$_{27}$H$_{50}$ClN$_3$O requires m/z 432.3954).

5-Bromo-4-(cyclopentyloxy)-2-(N,N-dimethylamino)-6-methylpyrimidine (34)

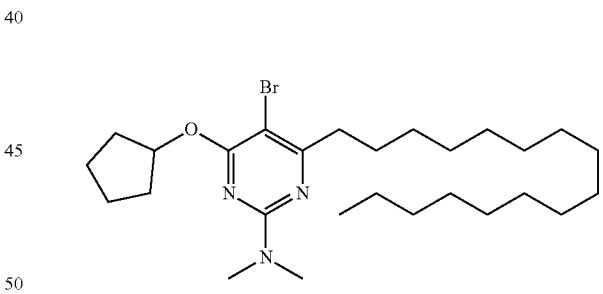

To a solution of 64.0 mg (0.18 mmol) of compound 33 in 3.00 mL of dry CH$_2$Cl$_2$ was added 46.0 mg (0.26 mmol) of recrystallized N-bromosuccinimide at 0° C. The reaction mixture was stirred for 2 h at room temperature. The reaction mixture was then diluted with 5 mL of water and extracted with seven 2-mL portions of dichloromethane. The organic layer was washed successively with water, brine and dried (MgSO$_4$). The excess solvent was concentrated under diminished pressure to afford a crude. The residue was purified by flash column chromatography on a silica gel column (24×2 cm). Elution with 1:5 ethyl acetate/hexane gave 34 as a colorless solid: yield 62 mg (82%); silica gel TLC R$_f$ 0.30 (1:2 ethyl acetate/hexanes); $^1$H NMR (CDCl$_3$) δ 0.87 (t, 3H, J=7.2 Hz), 1.25-1.32 (m, 27H), 1.63-1.65 (m, 11H), 1.66-1.80 (m, 1H), 2.08-2.14 (m, 4H) 2.14 (s, 3H), 2.35-2.43 (m, 3H), 3.11 (m, 6H); $^{13}$C NMR (CDCl$_3$) δ14.3, 22.8, 23.7, 24.09, 24.1, 24.2, 25.1, 27.6, 27.8, 29.0, 29.2, 29.4, 29.5, 29.5, 29.5, 29.6, 29.6, 29.7, 29.7, 29.8, 29.8, 32.1, 32.4, 32.9, 32.9, 34.8, 36.1, 36.2, 36.9, 37.1, 37.1, 79.9, 91.4, 160.3, 164.8 and 168.9; mass spectrum (MALDI), m/z 510.3059 (M+H)$^+$ (C$_{27}$H$_{49}$BrN$_3$O requires m/z 510.3059).

4-(Cyclopentyloxy)-2-(N,N-dimethylamino)-6-hexadecylpyrimidin-5-ol (7)

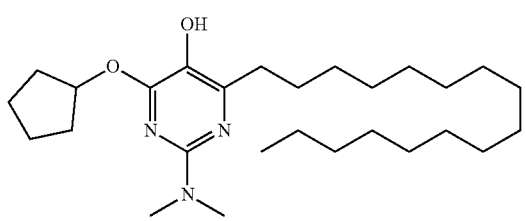 [SMILES: CCCCCCCCCCCCCCCCc1nc(N(C)C)nc(OC2CCCC2)c1O]

To a stirred solution at containing 84.0 mg (0.15 mmol) of compound 34 in 3.00 mL of anh THF was added 210 μL (0.33 mmol) of 1.6 M solution of n-BuLi in hexanes. The reaction mixture was stirred at −5° C. for 20 min. To the mixture was added 40.0 μL (36.0 mg; 0.33 mmol) of trimethyl borate and the reaction mixture was stirred for 1 h. To the reaction mixture was added 0.46 mL of 30% aq H$_2$O$_2$ followed by 0.15 mL of 3 N aq NaOH. The reaction mixture was stirred for 30 min and poured into 50 mL of water. The aq. mixture was neutralized with dilute aq. HCl and extracted with two 50-mL portions of ethyl acetate. The combined organic solution was washed successively with 80 mL of brine and distilled water, dried (MgSO$_4$). The excess solvent was concentrated under diminished pressure. The residue was purified by chromatography on a silica gel column (10×3 cm). Elution with 2:1 hexanes-ethyl acetate afforded compound 2-(dimethylamino)-4-methyl-6-(pentadecyloxy)pyrimidin-5-ol 7 as a colorless solid: yield 13 mg (18%); silica gel TLC R$_f$ 0.3 (1:1 ethyl ether/hexanes) $^1$H NMR (CDCl$_3$) δ 0.87 (t, 3H, J=7.2 Hz), 1.25-1.32 (m, 28H), 1.63-1.65 (m, 1H), 1.66-1.80 (m, 1H), 2.08-2.14 (m, 4H) 2.14 (s, 3H), 2.35-2.43 (m, 3H), 3.11 (m, 6H); $^{13}$C NMR (CDCl$_3$) δ 13.7, 14.3, 22.6, 28.4, 29.3, 29.5, 29.5, 29.8, 29.6, 30.7, 30.8, 31.9, 37.1, 47.2, 70.5, 128.8, 151.4, 154.2 and 157.5; mass spectrum (APCI), m/z 448.3903 (M+H)$^+$ (C$_{27}$H$_{50}$N$_3$O$_2$ requires m/z 448.3903).

Example 7: Preparation of 2-(Azetidin-1-yl)-4-methoxy-6-hexadecylpyrimidin-5-ol (8)

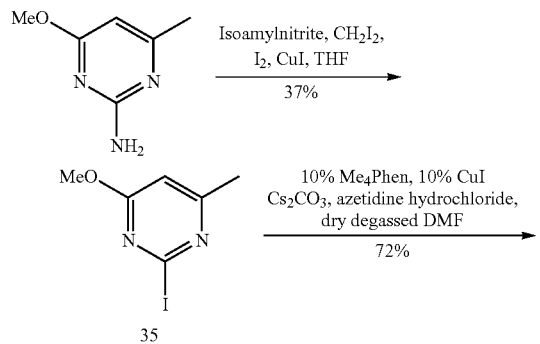

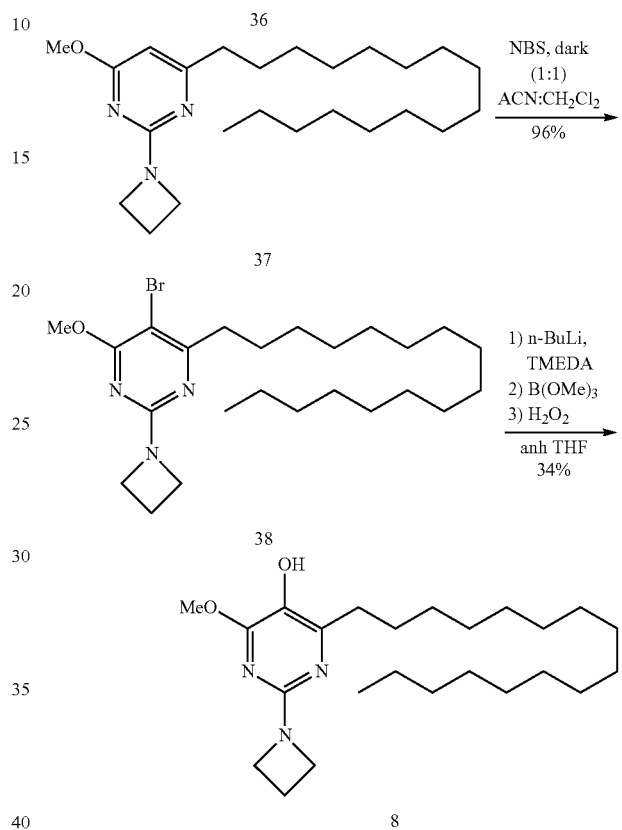

2-Iodo-4-methoxy-6-methylpyrimidine (35)

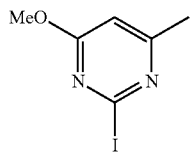

To a stirred solution containing 3.00 g (21.6 mmol) of 2-amino-4-methoxy-6-methylpyrimidine, 5.46 g (21.6 mmol) of iodine, 4.31 g (22.6 mmol) of CuI and 2.5 mL (30.9 mmol) of CH$_2$I$_2$ in 120 mL of anhydrous THF was added 10.5 mL (78.2 mmol) of isoamylnitrite. The reaction mixture was stirred at reflux for 3 h. The reaction mixture was allowed to warm to room temperature and then filtered through Celite, and the Celite pad was washed with CH$_2$Cl$_2$. The combined organic phase was washed with water and then with brine, dried (MgSO$_4$) and concentrated under diminished pressure. The residue was purified by flash chromatography on a silica gel column (20×5 cm). Elution with hexane followed by 95:5 hexane-Et$_2$O and then 80:20 hexane-Et₂O afforded 35 as a yellowish solid: yield 2.01 g (37%); mp 43-44° C.; silica gel TLC R$_f$ 0.35 (4:1 hexane-Et₂O); ¹H NMR (CDCl₃, 400 MHz) δ 2.37 (s, 3H), 3.93 (s, 3H) and 6.50 (s, 1H); ¹³C NMR (CDCl₃, 100 MHz) δ 23.7, 54.6, 106.5, 127.4, 169.0 and 169.1; mass spectrum (APCI), m/z 250.9675 (M+H)⁺ (C₆H₅N₂OI requires 250.9682).

2-(Azetidin-1-yl)-4-methoxy-6-methylpyrimidine (36)

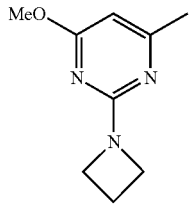

To a stirred solution containing 560 mg (5.98 mmol) of azetidine hydrochloride, 76.0 mg (0.39 mmol) of CuI, and 3.90 g (11.9 mmol) of Cs₂CO₃ in 10 mL dry degassed DMF was added 1.00 g (3.99 mmol) of 35 and 95.0 mg (0.39 mmol) of 3,4,7,8-tetramethyl-1,10-phenanthroline sequentially. The reaction mixture was stirred at 50° C. for 5 h. The mixture was allowed to warm to room temperature and then filtered through Celite and the Celite pad was washed with CH₂Cl₂. The combined organic phase was washed with water and then with brine, dried (MgSO₄) and concentrated under diminished pressure. The residue was purified by flash chromatography on a silica gel column (20×3 cm). Elution with hexane followed by 95:5 hexane-EtOAc and then 85:15 hexane-EtOAc afforded 36 as a yellowish oil: yield 515 mg (72%); silica gel TLC R$_f$ 0.26 (3:2 hexane-EtOAc); ¹H NMR (CDCl₃, 400 MHz) δ 2.25 (s, 3H), 2.30 (quint, 2H, J=8.0 Hz), 3.84 (s, 3H), 4.11 (t, 4H, J=7.6 Hz) and 5.83 (s, 1H); ¹³C NMR (CDCl₃, 100 MHz) δ 16.3, 24.1, 50.2, 53.0, 95.0, 163.2, 168.0 and 170.7; mass spectrum (APCI), m/z 180.1136 (M+H)⁺ (C₉H₁₄N₃O requires 180.1137).

2-(Azetidin-1-yl)-4-methoxy-6-hexadecylpyrimidine (37)

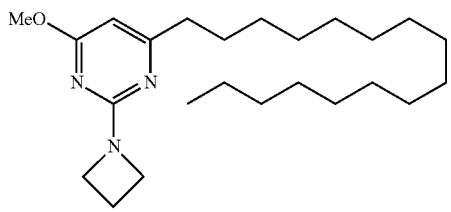 [SMILES: CCCCCCCCCCCCCCCCc1cc(OC)nc(N2CCC2)n1]

To a stirred solution containing 261 mg (1.45 mmol) of 36 in 7 mL of anhydrous THF at −78° C. was added 870 μL (2.17 mmol) of a 2.5 M solution of n-BuLi in hexane. The reaction mixture was stirred at −78° C. for 15 min and then 300 μL (1.03 mmol) of 1-bromopentadecane was added. The reaction was stirred at 0° C. for another 30 min, then quenched with satd aq ammonium chloride and extracted with 150 mL of EtOAc. The combined organic phase was washed with brine, dried (MgSO₄) and concentrated under diminished pressure. The residue was purified by chromatography on a silica gel column (20×3 cm). Elution with hexane followed by 95:5 hexane-Et₂O afforded 37 as a yellowish solid: yield 142 mg (25%) and 87 mg (33%) starting material was recovered; mp 45-46° C.; silica gel TLC R$_f$ 0.32 (4:1 hexane-Et₂O); ¹H NMR (CDCl₃, 400 MHz) δ 0.87 (t, 3H, J=7.2 Hz), 1.18-1.35 (m, 26H), 1.62 (quint, 2H, J=7.2 Hz), 2.29 (quint, 2H, J=7.2 Hz), 2.48 (t, 2H, J=7.6 Hz), 3.82 (s, 3H), 4.10 (t, 4H, J=7.6 Hz) and 5.83 (s, 1H); ¹³C NMR (CDCl₃, 100 MHz) δ 14.2, 16.3, 22.8, 28.7, 29.46, 29.5, 29.6, 29.7, 29.78, 29.8, 32.0, 37.9, 50.2, 52.9, 94.3, 163.3, 170.7 and 172.2; mass spectrum (APCI), m/z 390.3481 (M+H)⁺ (C₂₄H₄₄N₃O requires 390.3484).

2-(Azetidin-1-yl)-5-bromo-4-methoxy-6-hexadecylpyrimidine (38)

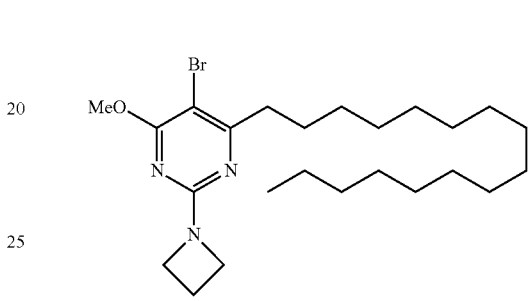

To a stirred solution containing 106 mg (0.27 mmol) of 37 in 4 mL (1:1) CH₂Cl₂-acetonitrile was added 58.0 mg (0.33 mmol) of NBS under dark. The reaction mixture was stirred for 30 min at room temperature under dark, then diluted with 50 mL CH₂Cl₂, washed with brine, dried (MgSO₄) and concentrated under diminished pressure. The residue was purified by chromatography on a silica gel column (15×3 cm). Elution with hexane followed by 95:5 hexane-Et₂O afforded 38 as a colorless solid: yield 121 mg (96%); mp 82-83° C.; silica gel TLC R$_f$ 0.55 (4:1 hexane-Et₂O); ¹H NMR (CDCl₃, 400 MHz) δ 0.88 (t, 3H, J=7.2 Hz), 1.19-1.37 (m, 26H), 1.64 (quint, 2H, J=7.2 Hz), 2.32 (quint, 2H, J=7.2 Hz), 2.69 (t, 2H, J=7.6 Hz), 3.93 (s, 3H) and 4.10 (t, 4H, J=7.6 Hz); ¹³C NMR (CDCl₃, 100 MHz) δ 14.3, 16.3, 22.8, 28.0, 29.5, 29.6, 29.7, 29.8, 29.9, 32.1, 37.0, 50.5, 54.3, 92.7, 161.2, 165.7 and 169.6; mass spectrum (APCI), m/z 468.2589 (M+H)⁺ (C₂₄H₄₃N₃OBr requires 468.2589).

2-(Azetidin-1-yl)-4-methoxy-6-hexadecylpyrimidin-5-ol (8)

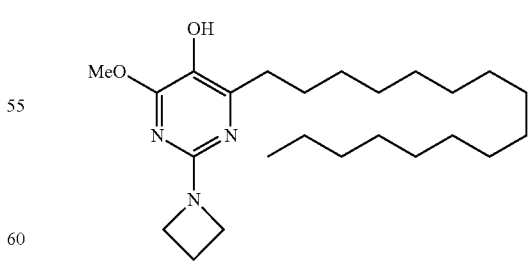

To a stirred solution containing 93.0 mg (0.19 mmol) of 38 in 2 mL of anhydrous THF at −5° C. was added 30 μL (0.19 mmol) of TMEDA and 198 μL (0.49 mmol) of a 2.5 M solution of n-BuLi in hexane. The reaction mixture was stirred at −5° C. for 15 min and then 66 μL (0.59 mmol)

trimethoxyborane was added. The reaction was stirred for 30 min at room temperature followed by addition of 426 μL (4.35 mmol) of H₂O₂ (35% v/v). The reaction mixture was stirred for additional 30 min and poured into 20 mL water, neutralized with dilute aq HCl and then extracted with 100 mL of EtOAc. The combined organic phase was washed with brine, dried (MgSO₄) and concentrated under diminished pressure. The residue was purified by chromatography on a silica gel column (15×3 cm). Elution with hexane followed by 90:10 hexane-EtOAc afforded 8 as a yellowish solid: yield 27.0 mg (34%); mp 59-60° C.; silica gel TLC $R_f$ 0.22 (4:1 hexane-EtOAc); ¹H NMR (CDCl₃, 400 MHz) δ 0.88 (t, 3H, J=7.2 Hz), 1.19-1.37 (m, 26H), 1.64 (quint, 2H, J=7.2 Hz), 2.27 (quint, 2H, J=7.2 Hz), 2.61 (t, 2H, J=8.0 Hz), 3.92 (s, 3H), 4.04 (t, 4H, J=7.6 Hz) and 4.61 (br s, 1H); ¹³C NMR (CDCl₃, 100 MHz) δ 14.3, 16.3, 22.8, 28.1, 29.5, 29.7, 29.72, 29.8, 29.82, 29.9, 31.5, 32.1, 51.0, 53.6, 128.3, 155.2, 157.6 and 158.6; mass spectrum (APCI), m/z 406.3436 (M+H)⁺ (C₂₄H₄₄N₃O₂ requires 406.3434).

Example 8: Preparation of 2-(Azetidin-1-yl)-4-ethoxy-6-hexadecylpyrimidin-5-ol (9)

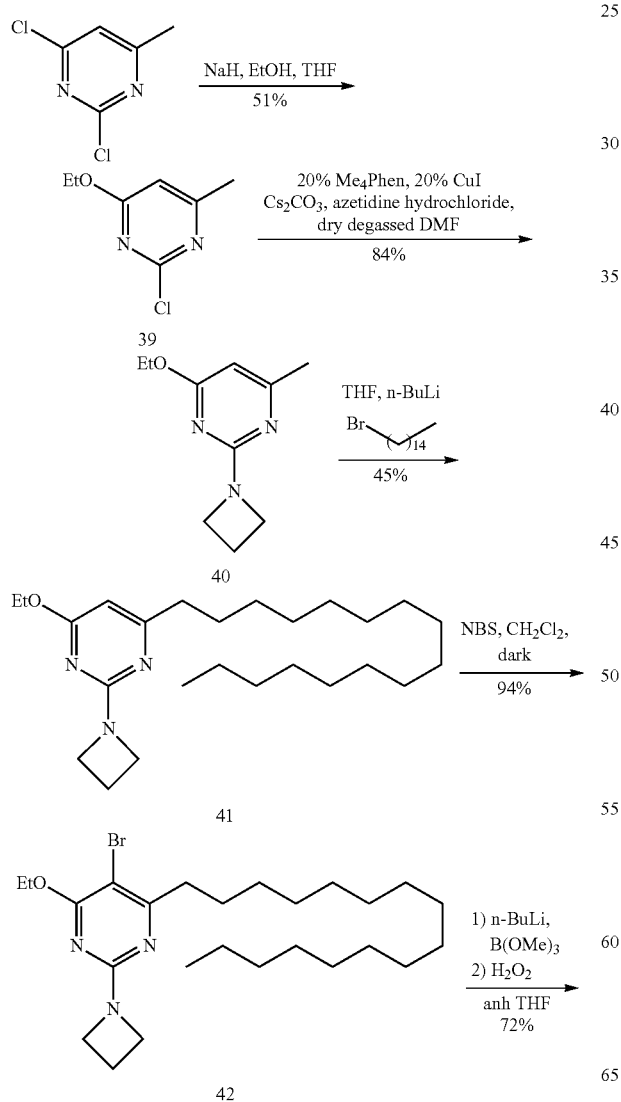

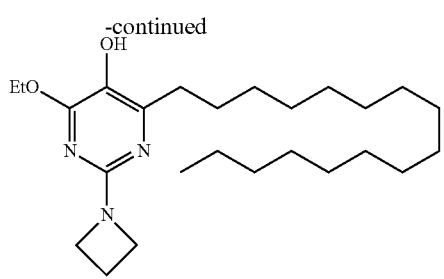

9

2-Chloro-4-ethoxy-6-methylpyrimidine (39)

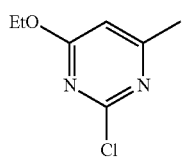

To a stirred solution containing 2.01 g (12.3 mmol) of 2,4-dichloro-6-methylpyrimidine in 40 mL of anhydrous THF was added 927 mg (38.6 mmol) of NaH (60% suspension in oil) and 392 L (12.9 mmol) of EtOH. The reaction mixture was stirred for 5 h at room temperature and then slowly poured into 200 mL of water. The crude was extracted with two 300-mL portions of EtOAc. The combined organic phase was washed with brine, dried (MgSO₄) and concentrated under diminished pressure. The residue was purified by chromatography on a silica gel column (15×6 cm). Elution with 19:1 hexane-EtOAc afforded 39 as a colorless solid: yield 2.16 g (51%); mp 37-38° C.; silica gel TLC $R_f$ 0.41 (4:1 hexane-EtOAc); ¹H NMR (CDCl₃, 400 MHz) δ 1.38 (t, 3H, J=7.2 Hz), 2.42 (s, 3H), 4.42 (d, 2H, J=7.2 Hz) and 6.46 (s, 1H); ¹³C NMR (CDCl₃, 100 MHz) δ 14.4, 23.8, 63.5, 105.7, 159.8, 169.8 and 170.9; mass spectrum (APCI), m/z 173.0477 (M+H)⁺ (C₇H₁₀N₂OCl requires 173.0482).

2-(Azetidin-1-yl)-4-ethoxy-6-methylpyrimidine (40)

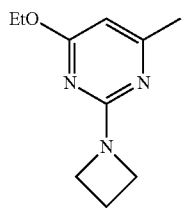

To a round bottom flask containing 600 mg (3.48 mmol) of 39, 489 mg (5.22 mmol) of azetidine hydrochloride, 131 mg (0.69 mmol) of CuI, 164 mg (0.69 mmol) of 3,4,7,8-tetramethyl-1,10-phenanthroline and 2.83 g (8.70 mmol) of Cs₂CO₃ was added 15 mL of dry degassed DMF. The reaction mixture was stirred at 50° C. for 3 h. The mixture was allowed to cool to room temperature and then filtered through Celite and the Celite pad was washed with CH₂Cl₂. The combined organic phase was washed with water and then with brine, dried (MgSO₄) and concentrated under diminished pressure. The residue was purified by flash chromatography on a silica gel column (15×3 cm). Elution with 19:1 hexane-EtOAc followed by 9:1 hexane-EtOAc afforded 40 as a colorless solid: yield 565 mg (84%); mp 42-43° C.; silica gel TLC $R_f$ 0.29 (3:2 hexane-EtOAc); $^1$H NMR (CDCl$_3$, 400 MHz) δ 1.24 (t, 3H, J=7.2 Hz), 2.16 (s, 3H), 2.20 (quint, 2H, J=7.6 Hz), 4.01 (t, 4H, J=7.6 Hz), 4.20 (q, 2H, J=7.2 Hz) and 5.73 (s, 1H); $^{13}$C NMR (CDCl$_3$, 100 MHz) δ 14.4, 16.1, 23.9, 49.9, 61.2, 95.0, 163.0, 167.7 and 170.1; mass spectrum (APCI), m/z 194.1289 (M+H)$^+$ (C$_{10}$H$_{16}$N$_3$O requires 194.1293).

2-(Azetidin-1-yl)-4-ethoxy-6-hexadecylpyrimidine (41)

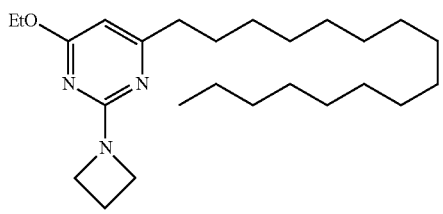 [SMILES: CCCCCCCCCCCCCCCCc1cc(OCC)nc(N2CCC2)n1]

To a stirred solution containing 450 mg (2.32 mmol) of 40 in 20 mL of anhydrous THF at −78° C. was added 1.02 mL (2.56 mmol) of a 2.5 M solution of n-BuLi in hexane. The reaction mixture was stirred at −78° C. for 15 min and then 475 µL (1.63 mmol) of 1-bromopentadecane was added. The reaction was stirred at 0° C. for another 30 min, then quenched with satd aq ammonium chloride and extracted with 150 mL of EtOAc. The combined organic phase was washed with brine, dried (MgSO$_4$) and concentrated under diminished pressure. The residue was purified by chromatography on a silica gel column (15×3 cm). Elution with 19:1 hexane-EtOAc afforded 41 as a colorless solid: yield 421 mg (45%); mp 40-41° C.; silica gel TLC $R_f$ 0.42 (4:1 hexane-EtOAc); $^1$H NMR (CDCl$_3$, 400 MHz) δ 0.84 (t, 3H, J=6.8 Hz), 1.18-1.33 (m, 29H), 1.60 (quint, 2H, J=6.8 Hz), 2.24 (quint, 2H, J=7.6 Hz), 2.44 (t, 2H, J=7.6 Hz), 4.05 (t, 4H, J=7.6 Hz), 4.26 (q, 2H, J=7.2 Hz) and 5.78 (s, 1H); $^{13}$C NMR (CDCl$_3$, 100 MHz) δ 14.1, 14.5, 16.2, 22.7, 28.6, 29.39, 29.42, 29.55, 29.61, 29.7, 29.8, 32.0, 37.8, 50.1, 61.3, 94.4, 163.2, 170.21 and 172.0; mass spectrum (FAB), m/z 404.3632 (M+H)$^+$ (C$_{25}$H$_{46}$N$_3$O requires 404.3641).

2-(Azetidin-1-yl)-5-bromo-4-ethoxy-6-hexadecylpyrimidine (42)

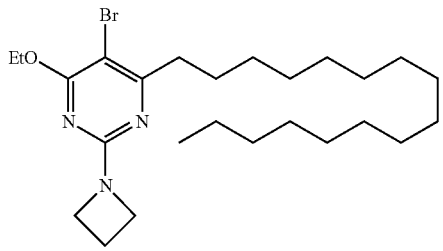 [SMILES: CCCCCCCCCCCCCCCCc1nc(N2CCC2)nc(OCC)c1Br]

To a stirred solution containing 464 mg (1.15 mmol) of 41 in 10 mL CH$_2$Cl$_2$ was added 209 mg (1.17 mmol) of NBS under dark (round bottom flask was wrapped with aluminum foil). The reaction mixture was stirred for 30 min at room temperature under dark, then diluted with CH$_2$Cl$_2$, washed with brine, dried (MgSO$_4$) and concentrated under diminished pressure. The residue was purified by chromatography on a silica gel column (15×3 cm). Elution with hexane followed by 96:4 hexane-EtOAc afforded 42 as a colorless solid: yield 522 mg (94%); mp 69-70° C.; silica gel TLC $R_f$ 0.56 (4:1 hexane-EtOAc); $^1$H NMR (CDCl$_3$, 400 MHz) δ 0.87 (t, 3H, J=7.2 Hz), 1.18-1.40 (m, 29H), 1.64 (quint, 2H, J=7.6 Hz), 2.29 (quint, 2H, J=7.6 Hz), 2.69 (t, 2H, J=7.6 Hz), 4.06 (t, 4H, J=7.6 Hz) and 4.37 (q, 2H, J=7.2 Hz); $^{13}$C NMR (CDCl$_3$, 100 MHz) δ 14.2, 14.5, 16.2, 22.8, 27.9, 29.5, 29.56, 29.58, 29.7, 29.78, 29.83, 32.1, 37.0, 50.3, 62.8, 92.9, 161.1, 165.2 and 169.4; mass spectrum (FAB), m/z 482.2753 (M+H)$^+$ (C$_{25}$H$_{45}$N$_3$OBr requires 482.2746).

2-(Azetidin-1-yl)-4-ethoxy-6-hexadecylpyrimidin-5-ol (9)

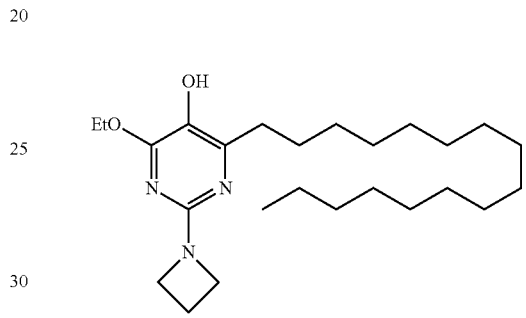

To a stirred solution containing 400 mg (0.83 mmol) of 42 in 10 mL of anhydrous THF at −5° C. was added 663 µL (1.66 mmol) of a 2.5 M solution of n-BuLi in hexane and 278 µL (2.49 mmol) of trimethoxyborane. The reaction mixture was stirred at 23° C. for 30 min followed by addition of 1.2 mL (18.3 mmol) of H$_2$O$_2$ (50% v/v). The reaction mixture was stirred for additional 30 min, poured into 20 mL NaHCO$_3$ and then extracted with 100 mL of CH$_2$Cl$_2$. The combined organic phase was washed with brine, dried (MgSO$_4$) and concentrated under diminished pressure. The residue was purified by chromatography on a silica gel column (15×3 cm). Elution with 95:5 hexane-EtOAc afforded 9 as a colorless powder: yield 250 mg (72%); mp 79-80° C.; silica gel TLC $R_f$ 0.33 (4:1 hexane/EtOAc); $^1$H NMR (CDCl$_3$, 400 MHz) δ 0.88 (t, 3H, J=7.2 Hz), 1.19-1.39 (m, 29H), 1.63 (quint, 2H, J=7.6 Hz), 2.26 (quint, 2H, J=7.2 Hz), 2.61 (t, 2H, J=7.6 Hz), 4.02 (t, 4H, J=7.6 Hz), 4.37 (q, 2H, J=7.2 Hz) and 4.89 (br s, 1H); $^{13}$C NMR (CDCl$_3$, 100 MHz) δ 14.3, 14.7, 16.3, 22.8, 28.1, 29.5, 29.71, 29.73, 29.77, 29.81, 29.85, 31.5, 32.1, 50.9, 62.3, 128.3, 155.1, 157.6 and 158.3; mass spectrum (FAB), m/z 420.3578 (M+H)$^+$ (C$_{25}$H$_{46}$N$_3$O$_2$ requires 420.3590).

Example 9: Preparation of 2-(Azetidin-1-yl)-4-hexadecyl-6-methylpyrimidin-5-ol (10)

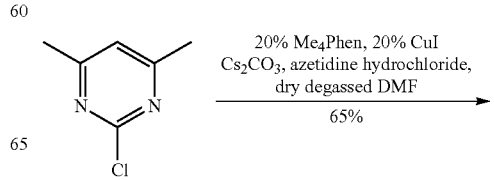

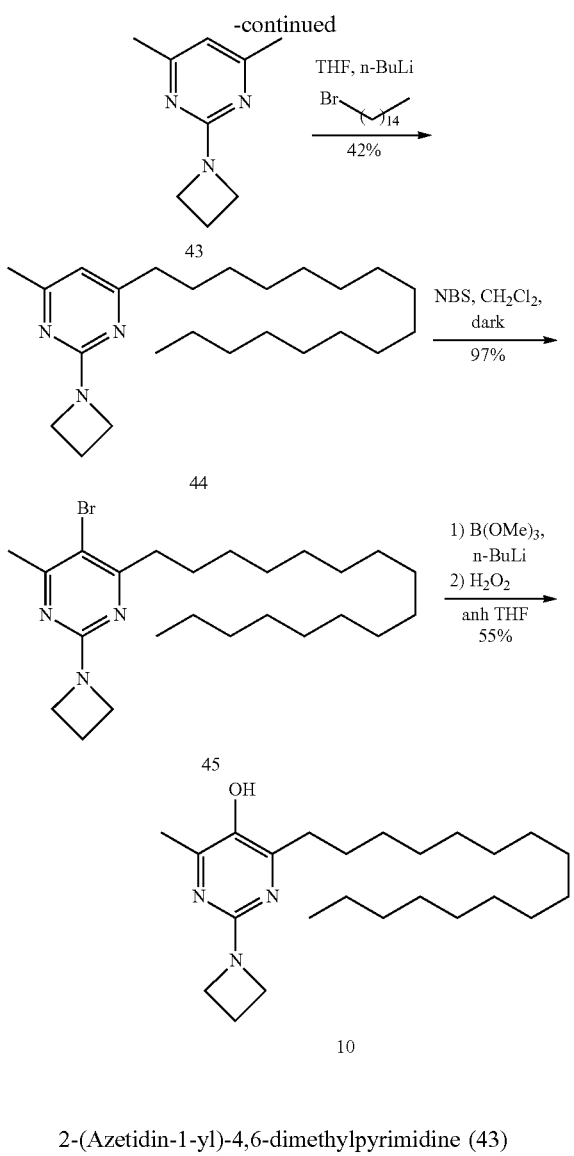

2-(Azetidin-1-yl)-4,6-dimethylpyrimidine (43)

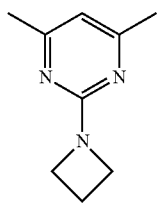

To a stirred solution containing 655 mg (6.99 mmol) of azetidine hydrochloride, 133 mg (6.99 mmol) of CuI, and 3.42 g (10.5 mmol) of Cs$_2$CO$_3$ in 10 mL dry degassed DMF was added 500 mg (3.49 mmol) of 2-chloro-4,6-dimethylpyrimidine and 165 mg (6.99 mmol) 3,4,7,8-tetramethyl-1,10-phenanthroline sequentially. The reaction mixture was stirred at 50° C. for 4 h. The reaction mixture was allowed to warm to room temperature and was then filtered through Celite, and the Celite pad was washed with CH$_2$Cl$_2$. The combined organic phase was washed with water and then with brine, dried (MgSO$_4$) and concentrated under diminished pressure. The residue was purified by flash chromatography on a silica gel column (15×3 cm). Elution with hexane followed by 4:1 hexane-EtOAc and then 1:1 hexane-EtOAc afforded 43 as yellowish solid: yield 372 mg (65%); mp 51-52° C.; silica gel TLC R$_f$ 0.22 (3:2 hexane-EtOAc); $^1$H NMR (CDCl$_3$, 400 MHz) δ 2.20 (s, 6H), 2.24 (t, 2H, J=7.6 Hz), 4.05 (t, 4H, J=7.2 Hz) and 6.19 (s, 1H); $^{13}$C NMR (CDCl$_3$, 100 MHz) δ 16.2, 23.9, 50.1, 109.1, 163.2 and 167.0; mass spectrum (FAB), m/z 164.1192 (M+H)$^+$ (C$_9$H$_{14}$N$_3$ requires 164.1188).

2-(Azetidin-1-yl)-4-hexadecyl-6-methylpyrimidine (44)

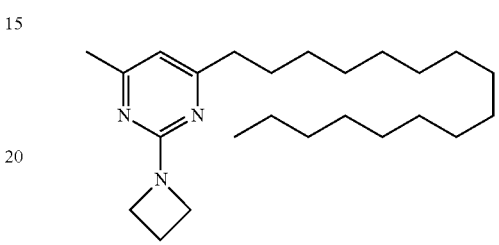

To a stirred solution containing 321 mg (1.96 mmol) of 43 in 10 mL of anhydrous THF at −78° C. was added 1.02 mL (2.56 mmol) of a 2.5 M solution of n-BuLi in hexane. The reaction mixture was stirred at −78° C. for 15 min and then 398 μL (1.37 mmol) of 1-bromopentadecane was added. The reaction was stirred at 0° C. for another 30 min, then quenched with satd aq ammonium chloride and extracted with 150 mL of EtOAc. The combined organic phase was washed with brine, dried (MgSO$_4$) and concentrated under diminished pressure. The residue was purified by chromatography on a silica gel column (20×3 cm). Elution with hexane followed by 96:4 hexane-EtOAc and then 90:10 hexane-EtOAc afforded 44 as a colorless solid: yield 307 mg (42%); mp 63-64° C.; silica gel TLC R$_f$ 0.45 (3:2 hexane-EtOAc); $^1$H NMR (CDCl$_3$, 400 MHz) δ 0.86 (t, 3H, J=6.8 Hz), 1.18-1.37 (m, 26H), 1.62 (quint, 2H, J=7.6 Hz), 2.27 (s, 3H), 2.29 (quint, 2H, J=7.6 Hz), 2.49 (t, 2H, J=7.2 Hz), 4.11 (t, 4H, J=7.2 Hz) and 6.24 (s, 1H); $^{13}$C NMR (CDCl$_3$, 100 MHz) δ 14.2, 16.4, 22.8, 24.2, 28.8, 29.46, 29.5, 29.6, 29.64, 29.75, 29.8, 32.0, 37.9, 50.3, 108.6, 163.4, 167.0 and 171.2; mass spectrum (FAB), m/z 374.3545 (M+H)$^+$ (C$_{24}$H$_{44}$N$_3$ requires 374.3535).

2-(Azetidin-1-yl)-5-bromo-4-hexadecyl-6-methylpyrimidine (45)

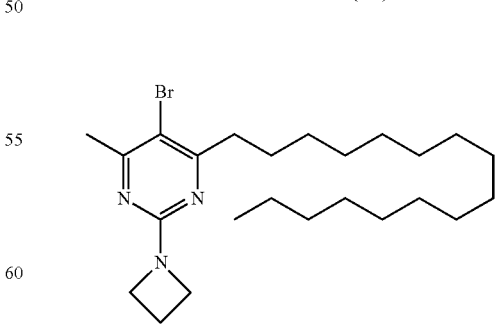

To a stirred solution containing 290 mg (0.77 mmol) of 44 in 5 mL CH$_2$Cl$_2$ was added 152 mg (0.85 mmol) of NBS under dark. The reaction mixture was stirred for 30 min at room temperature under dark, then diluted with 20 mL CH$_2$Cl$_2$, washed with brine, dried (MgSO$_4$) and concentrated under diminished pressure. The residue was purified by chromatography on a silica gel column (15×3 cm). Elution with hexane followed by 96:4 hexane-EtOAc afforded 45 as a colorless solid: yield 338 mg (97%); mp 74-75° C.; silica gel TLC R$_f$ 0.45 (4:1 hexane-EtOAc); $^1$H NMR (CDCl$_3$, 400 MHz) δ 0.87 (t, 3H, J=7.2 Hz), 1.18-1.37 (m, 26H), 1.65 (quint, 2H, J=7.6 Hz), 2.31 (quint, 2H, J=7.6 Hz), 2.44 (s, 3H), 2.71 (t, 2H, J=7.6 Hz) and 4.09 (t, 4H, J=7.6 Hz); $^{13}$C NMR (CDCl$_3$, 100 MHz) δ 14.2, 16.3, 22.8, 25.3, 27.8, 29.5, 29.6, 29.7, 29.8, 29.84, 32.1, 37.4, 50.5, 108.6, 161.3, 165.7 and 168.8; mass spectrum (FAB), m/z 454.2611 (M+H)$^+$ (C$_{24}$H$_{43}$N$_3$O$^{81}$Br requires 454.2620).

2-(Azetidin-1-yl)-4-hexadecyl-6-methylpyrimidin-5-ol (10)

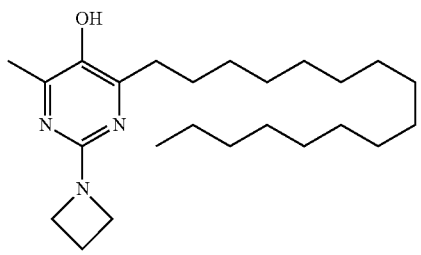 [SMILES: CCCCCCCCCCCCCCCCc1nc(N2CCC2)nc(C)c1O]

To a stirred solution containing 57.0 mg (0.13 mmol) of 45 in 2 mL of anhydrous THF at −5° C. was added 84 µL (0.75 mmol) of trimethoxyborane and 156 µL (0.39 mmol) of a 2.5 M solution of n-BuLi in hexane. The reaction mixture was stirred at 23° C. for 30 min followed by addition of 221 µL (3.25 mmol) of H$_2$O$_2$ (50% v/v). The reaction mixture was stirred for additional 30 min and poured into 20 mL water, neutralized with dilute aq HCl and then extracted with 100 mL of EtOAc. The combined organic phase was washed with brine, dried (MgSO$_4$) and concentrated under diminished pressure. The residue was purified by chromatography on a silica gel column (15×3 cm). Elution with 95:5 hexane-EtOAc followed by 80:20 hexane-EtOAc afforded 10 as a yellowish oil: yield 28.0 mg (55%); silica gel TLC R$_f$ 0.27 (3:2 hexane-EtOAc); $^1$H NMR (CD$_3$OD, 400 MHz) δ 0.90 (t, 3H, J=6.8 Hz), 1.27-1.32 (m, 26H), 1.64 (m, 2H), 2.25-2.34 (m, 5H), 2.65 (m, 2H), 4.04 (t, 4H, J=7.6 Hz) and 4.28 (br s, 1H); $^{13}$C NMR (CD$_3$OD, 100 MHz) δ 14.5, 17.0, 18.6, 23.8, 29.1, 30.5, 30.6, 30.7, 30.8, 30.81, 30.83, 32.8, 33.1, 52.2, 140.7, 157.6, 159.9 and 161.6; mass spectrum (FAB), m/z 390.3480 (M+H)$^+$ (C$_{24}$H$_{44}$N$_3$O requires 390.3484).

Example 10: Preparation of 2-(Azetidin-1-yl)-4-methyl-6-(pentadecyloxy)-pyrimidin-5-ol (11)

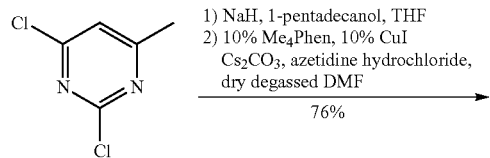

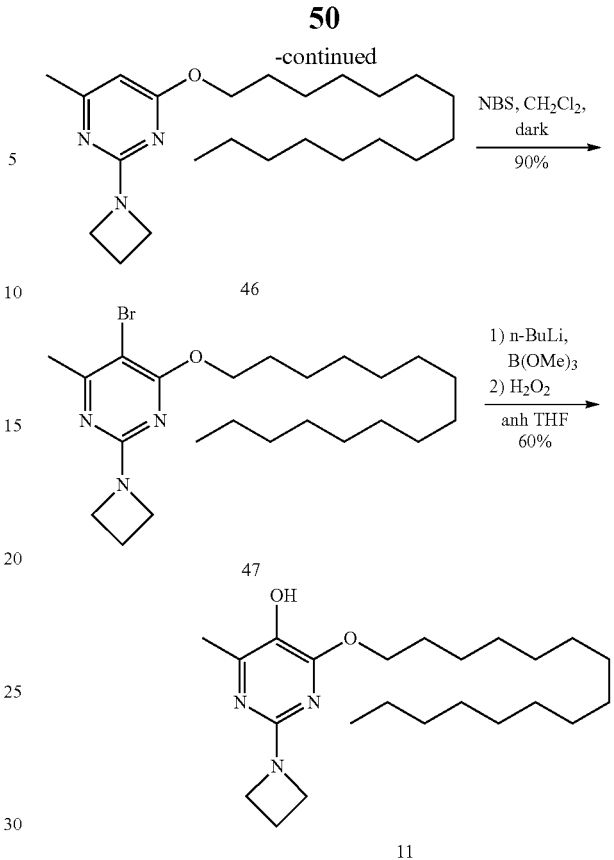

2-(Azetidin-1-yl)-4-methyl-6-(pentadecyloxy)pyrimidine (46)

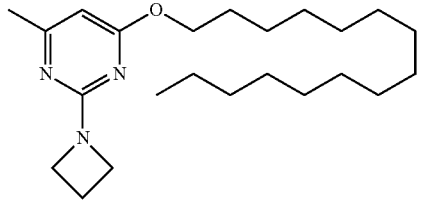 [SMILES: CCCCCCCCCCCCCCCOc1cc(C)nc(N2CCC2)n1]

To a stirred solution containing 1.01 g (6.13 mmol) of 2,4-dichloro-6-methylpyrimidine in 20 mL of anhydrous THF was added 620 mg (25.8 mmol) of NaH (60% suspension in oil) and 1.47 g (6.44 mmol) of 1-pentadecanol. The reaction mixture was stirred for 24 h at room temperature and then slowly poured into 100 mL of water. The crude was extracted with two 200-mL portions of EtOAc. The combined organic phase was washed with brine, dried (MgSO$_4$) and concentrated under diminished pressure to afford 790 mg of crude 2-chloro-4-methyl-6-(pentadecyloxy)pyrimidine. To a round bottom flask containing 350 mg (0.99 mmol) of crude 2-chloro-4-methyl-6-(pentadecyloxy)pyrimidine, 139 mg (1.49 mmol) of azetidine hydrochloride, 19.0 mg (0.09 mmol) of CuI, 23.0 mg (0.09 mmol) of 3,4,7,8-tetramethyl-1,10-phenanthroline and 806 mg (2.48 mmol) of Cs$_2$CO$_3$ was added 15 mL dry degassed DMF. The reaction mixture was stirred at 50° C. for 5 h. The mixture was allowed to cool to room temperature and then filtered through Celite and the Celite pad was washed with CH$_2$Cl$_2$.

The combined organic phase was washed with water and then with brine, dried (MgSO$_4$) and concentrated under diminished pressure. The residue was purified by flash chromatography on a silica gel column (15×3 cm). Elution with 19:1 hexane-EtOAc followed by 9:1 hexane-EtOAc afforded 46 as a colorless solid: yield 282 mg (76%); mp 40-41° C.; silica gel TLC R$_f$ 0.27 (4:1 hexane-EtOAc); $^1$H NMR (CDCl$_3$, 400 MHz) δ 0.86 (t, 3H, J=6.8 Hz), 1.21-1.38 (m, 24H), 1.70 (quint, 2H, J=7.2 Hz), 2.24 (s, 3H), 2.29 (quint, 2H, J=7.6 Hz), 4.09 (t, 4H, J=7.6 Hz), 4.21 (t, 2H, J=6.8 Hz) and 5.81 (s, 1H); $^{13}$C NMR (CDCl$_3$, 100 MHz) δ 14.3, 16.4, 22.9, 24.2, 26.2, 29.1, 29.5, 29.7, 29.76, 29.8, 29.9, 32.1, 50.3, 65.9, 95.3, 163.2, 168.0 and 170.6; mass spectrum (FAB), m/z 376.3317 (M+H)$^+$ (C$_{23}$H$_{42}$N$_3$O requires 376.3328).

2-(Azetidin-1-yl)-5-bromo-4-methyl-6-(pentadecyloxy)pyrimidine (47)

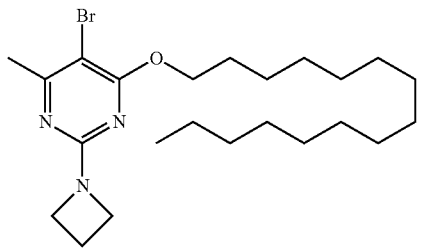

To a stirred solution containing 145 mg (0.39 mmol) of 46 in 4 mL CH$_2$Cl$_2$ was added 72.0 mg (0.41 mmol) of NBS under dark. The reaction mixture was stirred for 30 min at room temperature under dark, then diluted with CH$_2$Cl$_2$, washed with brine, dried (MgSO$_4$) and concentrated under diminished pressure. The residue was purified by chromatography on a silica gel column (15×3 cm). Elution with hexane followed by 96:4 hexane-EtOAc afforded 47 as a colorless solid: yield 159 mg (90%); mp 71-72° C.; silica gel TLC R$_f$ 0.53 (4:1 hexane-EtOAc); $^1$H NMR (CDCl$_3$, 400 MHz) δ 0.87 (t, 3H, J=6.8 Hz), 1.21-1.47 (m, 24H), 1.75 (quint, 2H, J=7.6 Hz), 2.30 (quint, 2H, J=7.2 Hz), 2.40 (s, 3H), 4.07 (t, 4H, J=7.6 Hz) and 4.30 (t, 2H, J=6.8 Hz); $^{13}$C NMR (CDCl$_3$, 100 MHz) δ 14.2, 16.2, 22.8, 24.5, 26.1, 28.9, 29.45, 29.5, 29.7, 29.72, 29.8, 29.83, 32.1, 50.4, 67.1, 93.3, 161.0, 165.3 and 166.0; mass spectrum (FAB), m/z 454.2421 (M+H)$^+$ (C$_{23}$H$_{41}$N$_3$OBr requires 454.2433).

2-(Azetidin-1-yl)-4-methyl-6-(pentadecyloxy)pyrimidin-5-ol (11)

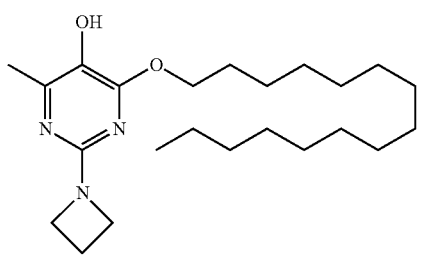 [SMILES: CCCCCCCCCCCCCCCOc1nc(N2CCC2)nc(C)c1O]

To a stirred solution containing 130 mg (0.28 mmol) of 47 in 3 mL of anhydrous THF at −5° C. was added 229 µL (0.57 mmol) of a 2.5 M solution of n-BuLi in hexane and 94 µL (0.84 mmol) of trimethoxyborane. The reaction mixture was stirred at 23° C. for 30 min followed by addition of 419 µL (6.16 mmol) of H$_2$O$_2$ (50% v/v). The reaction mixture was stirred for additional 30 min, poured into 20 mL NaHCO$_3$ and then extracted with 100 mL of CH$_2$Cl$_2$. The combined organic phase was washed with brine, dried (MgSO$_4$) and concentrated under diminished pressure. The residue was purified by chromatography on a silica gel column (15×3 cm). Elution with 95:5 hexane-EtOAc afforded 11 as a colorless powder: yield 66.0 mg (60%); mp 83-85° C.; silica gel TLC R$_f$ 0.21 (3:2 hexane-EtOAc); $^1$H NMR (CDCl$_3$, 400 MHz) δ 0.86 (t, 3H, J=6.8 Hz), 1.05-1.41 (m, 24H), 1.70 (quint, 2H, J=6.8 Hz), 2.15-2.32 (m, 5H), 4.01 (t, 4H, J=7.2 Hz), 4.30 (t, 2H, J=6.8 Hz) and 5.11 (br s, 1H); $^{13}$C NMR (CDCl$_3$, 100 MHz) δ 14.2, 16.3, 17.8, 22.8, 26.1, 29.0, 29.5, 29.7, 29.74, 29.8, 29.83, 32.1, 50.9, 66.6, 128.6, 151.1, 157.3 and 158.5; mass spectrum (FAB), m/z 392.3286 (M+H)$^+$ (C$_{23}$H$_{42}$N$_3$O$_2$ requires 392.3277).

Example 11: Preparation of 2-(Azetidin-1-yl)-4-cyclobutyl-6-hexadecylpyrimidin-5-ol (12)

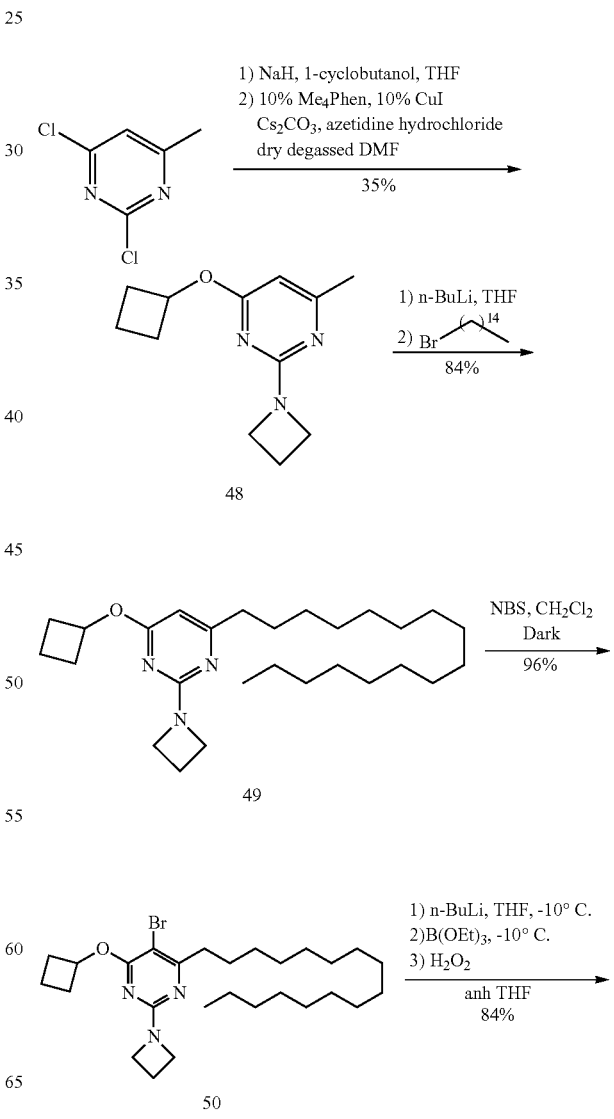

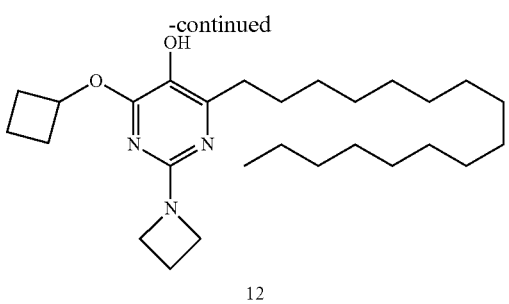

2-(Azetidin-1-yl)-4-cyclobutanoxy-6-methylpyrimidine (48)

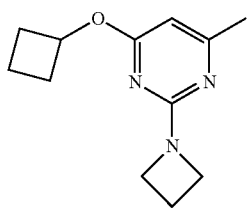 [SMILES: Cc1cc(OC2CCC2)nc(N2CCC2)n1]

To a stirred solution containing 1 g (5 mmol) of the crude mixture 20 in 3 mL of previously dried and degassed DMF was added 3.25 g (10 mmol) of $Cs_2CO_3$ and 936 mg (10 mmol) of azetidine hydrochloride. The suspension was stirred under argon at room temperature for 10 min and 118 mg (0.5 mmol) of 3, 4, 7, 8-tetramethyl-1,10-phenanthroline and 95 mg (0.5 mmol) of copper (I) iodide where added to the mixture successively. The reaction mixture was then warmed to 50° C. and kept under argon for 12 h. After the reaction was complete, the reaction mixture was diluted in 30 mL of EtOAc and filtrated through Celite. The resulting filtrate was concentrated to dryness. The crude residue was purified by flash chromatography on a silica gel column (15×4 cm). Elution with 9:1 hexane-EtOAc afforded 48 as a colorless solid: yield 390 mg (35%); mp 60-61° C.; silica gel TLC $R_f$ 0.22 (4:1 hexane-EtOAc); $^1$H NMR (CDCl$_3$) δ 1.58-1.70 (m, 1H), 1.76-1.84 (m, 1H), 2.05-2.17 (m, 2H), 2.24 (s, 3H), 2.29 (qt, 2H, J=7.4 Hz), 2.38 (m, 2H), 4.08 (t, 4H, J=7.5 Hz), 5.04 (qt, 1H, J=7.4 Hz), 5.77 (s, 1H); $^{13}$C NMR (CDCl$_3$) δ 13.6, 16.3, 24.2, 30.8, 50.2, 70.1, 95.0, 163.2, 168.2, 169.6; mass spectrum (APCI), m/z 220.1145 (M+H)$^+$ ($C_{12}H_{18}N_3O$ requires m/z 220.1450).

2-(Azetidin-1-yl)-4-cyclobutanoxy-6-hexadecylpyrimidine (49)

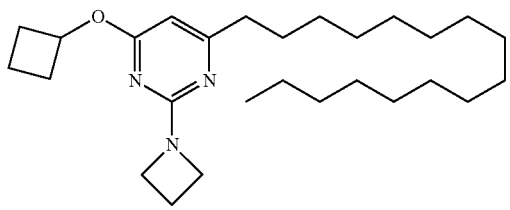 [SMILES: CCCCCCCCCCCCCCCCc1cc(OC2CCC2)nc(N2CCC2)n1]

A stirred solution containing 242 mg (1.075 mmol) of 48 in 6 mL of freshly distilled THF was cooled under argon at −78° C. and kept under argon for 15 min. 739 μL (1.183 mmol) of a 1.6 M solution of n-BuLi in hexane was slowly added dropwise and the resulting mixture was kept under stirring at −78° C. for 1 h. 319 mg (1.075 mmol) of 1-bromopentadecane in a solution in 500 μL of distilled THF was then added dropwise and the reaction mixture was warmed to 0° C. and stirred for 1 h. The reaction was quenched by adding 30 mL of saturated NH$_4$Cl, and extracted with two 25 mL portions of CH$_2$Cl$_2$. The organic phase was combined, dried over MgSO$_4$ and concentrated under diminished pressure. The residue was purified by flash chromatography on a silica gel column (15×2 cm). Elution with 98:2 to 95:5 hexane:EtOAc afforded compound 49 as a colorless solid: yield 389 mg (84%); mp 39-40° C.; silica gel TLC $R_f$ 0.5 (9:1 Hexane/EtOAc); $^1$H NMR (CDCl$_3$) δ 0.87 (t, 3H, J=6.6 Hz), 1.2-1.35 (m, 26H), 1.58-1.70 (m, 3H), 1.76-1.85 (m, 1H), 2.07-2.18 (m, 2H), 2.25-2.32 (m, 2H), 2.35-2.45 (m, 2H), 2.7 (t, 2H, J=7.6 Hz), 4.08 (t, 4H, J=7.5 Hz), 5.06 (qt, 1H, J=7.4 Hz), 5.78 (s, 1H); $^{13}$C NMR (CDCl$_3$) δ 13.7, 14.2 16.3, 22.8, 28.8, 29.5, 29.5, 29.6, 29.7, 29.8, 29.8, 29.8, 30.8, 32.1, 38.0, 50.2, 70.1, 94.3, 163.4, 169.6 and 172.5; mass spectrum (FAB), m/z 430.3786 (M+H)$^+$ ($C_{25}H_{48}N_3O$ requires m/z 430.3797).

2-(Azetidin-1-yl)-5-bromo-4-cyclobutanoxy-6-hexadecylpyrimidine (50)

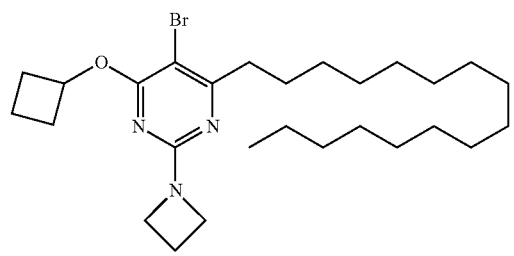

To a stirred solution containing 340 mg (0.791 mmol) of 49 were dissolved in 8 mL of freshly distilled CH$_2$Cl$_2$ at room temperature under darkness was added 147 mg (0.83 mmol) of recrystallised NBS. The reaction mixture was stirred under argon for 1 h. The solvent was removed under reduced pressure and the resulting residue was purified by flash chromatography on a silica gel column (15×2 cm). Elution with 98:2 Hexane/EtOAc to afford compound 50 as a colorless solid: yield 389 mg (96%); mp 71-73° C. silica gel TLC $R_f$ 0.5 (95:5 hexane/EtOAc); $^1$H NMR (CDCl$_3$) δ 0.88 (t, 3H, J=6.6 Hz), 1.2-1.35 (m, 26H), 1.58-1.70 (m, 3H), 1.78-1.86 (m, 1H), 2.13-2.22 (m, 2H), 2.25-2.33 (m, 2H), 2.39-2.46 (m, 2H), 2.67-2.71 (m, 2H), 4.06 (t, 4H, J=7.5 Hz), 5.13 (qt, 1H, J=7.4 Hz); $^{13}$C NMR (CDCl$_3$) δ 13.7, 14.2, 16.2, 22.8, 28.0, 29.5, 29.6, 29.7, 29.8, 29.8, 29.81, 29.9, 30.8, 32.1, 37.0, 50.3, 71.3, 92.7, 161.1, 164.7, 169.5; mass spectrum (FAB), m/z 508.2897 (M+H)$^+$ ($C_{25}H_{47}BrN_3O$ requires m/z 508.2902).

2-(Azetidin-1-yl)-4-cyclobutanoxy-6-hexadecylpyrimidin-5-ol (12)

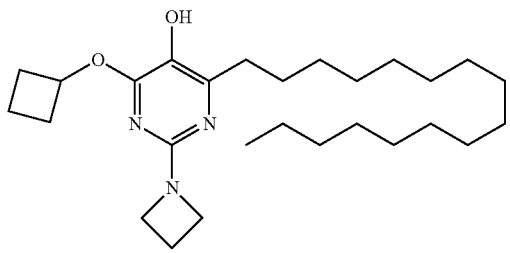 [SMILES: CCCCCCCCCCCCCCCCc1nc(N2CCC2)nc(OC2CCC2)c1Br]

a stirred solution containing 340 mg (0.666 mmol) of 50 in 6 mL of freshly distilled THF was cooled down to −10° C. and kept under argon for 10 min. To the resulting suspension was added 458 μL of 1.6 M solution of n-butyllithium in hexane (0.733 mmol) and the resulting mixture was kept under stirring at −10° C. for 1 h leading to a clear yellowish solution. 120 μL (1.332 mmol) of Triethyl borate was slowly added and the reaction was kept at −10° C. for 1 more hour. 600 μL of $H_2O_2$ (30% v/v) were then added and The reaction was warmed to room temperature and stirred for 30 min. The mixture was diluted by addition of 30 mL of $NH_4Cl$ Sat. and extracted with two portions of 25 mL of $CH_2Cl_2$. The organic phases were combined, dried over $MgSO_4$ and concentrated under diminished pressure. The residue was purified by flash chromatography on a silica gel column (15×2 cm). Elution with 98:2 to 9:1 hexane/EtOAc afforded compound 12 as a colorless solid: yield 248 mg (84%); mp 95-97° C.; silica gel TLC $R_f$ 0.42 (4:1 hexane-EtOAc); $^1H$ NMR (CDCl$_3$) δ 0.88 (t, 3H, J=6.6 Hz), 1.2-1.35 (m, 26H), 1.55-1.70 (m, 3H), 1.63 (m, 3H), 1.83 (m, 1H), 2.06-2.16 (m, 2H), 2.26 (quint, 2H, J=7.2 Hz), 2.37-2.45 (m, 2H), 2.61 (m, 2H), 4.01 (t, 4H, J=7.2 Hz), 4.76 br s, 1H) and 5.17 (qt, 1H, J=7.4 Hz); $^{13}C$ NMR (CDCl$_3$) δ 13.6, 14.3, 16.3, 22.8, 28.2, 29.5, 29.71, 29.73, 29.8, 29.81, 29.86, 29.9, 30.9, 31.5, 32.1, 50.9, 70.8, 128.1, 155.2, 157.6, 157.8; mass spectrum (FAB), m/z 446.3742 (M+H)$^+$ ($C_{25}H_{48}N_3O_2$ requires m/z 446.3747).

Example 12: Preparation of 4-Cyclobutoxy-2-(N,N-dimethylamino-$d_6$)-6-hexadecylpyrimidin-5-ol (13)

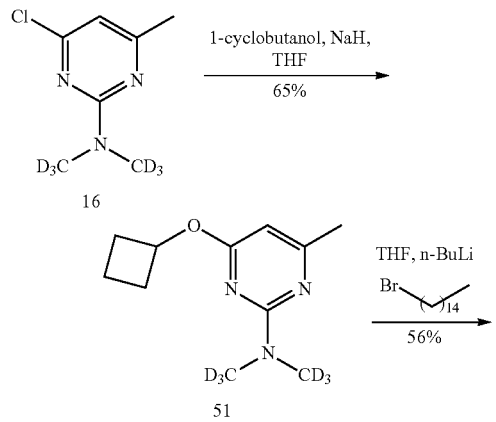

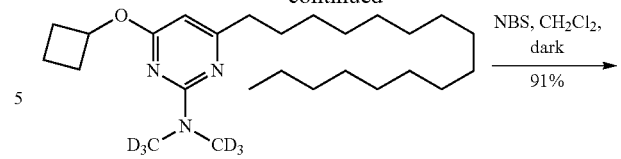

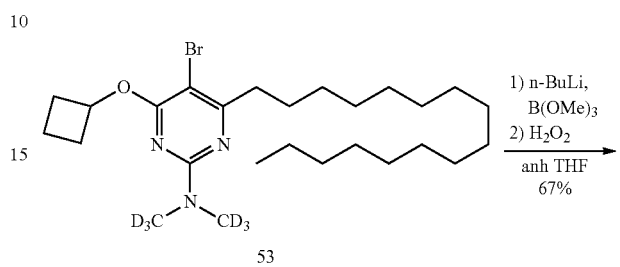

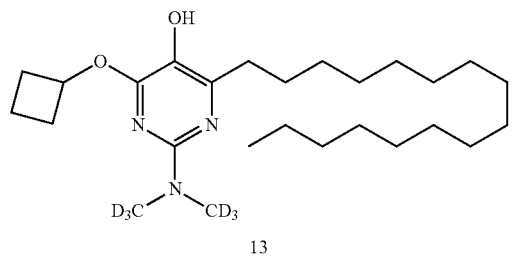

4-Cyclobutoxy-2-(N,N-dimethylamino)-6-methylpyrimidine-$d_6$ (51)

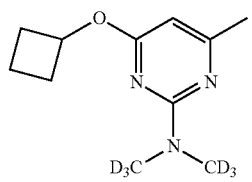 [SMILES: [2H]C([2H])([2H])N(c1nc(C)cc(OC2CCC2)n1)C([2H])([2H])[2H]]

To a stirred solution containing 500 mg (2.81 mmol) of 16 in 10 mL of anhydrous THF was added 405 mg (16.9 mmol) of NaH (60% suspension in oil) and 343 μL (4.38 mmol) of 1-cyclobutanol. The reaction mixture was stirred at reflux for 48 h and then allowed to cool to room temperature. The mixture was slowly poured into 100 mL of water and extracted with two 150-mL portions of EtOAc. The combined organic phase was washed with brine, dried (MgSO$_4$) and concentrated under diminished pressure. The residue was purified by chromatography on a silica gel column (20×3 cm). Elution with 19:1 hexane-Et$_2$O afforded 51 as a colorless oil: yield 391 mg (65%); silica gel TLC $R_f$ 0.36 (4:1 hexane-Et$_2$O); $^1H$ NMR (CDCl$_3$, 400 MHz) δ 1.62 (m, 1H), 1.78 (m, 1H), 2.10 (m, 2H), 2.21 (s, 3H), 2.38 (m, 2H), 5.08 (quint, 1H, J=7.2 Hz) and 5.71 (s, 1H); $^{13}C$ NMR (CDCl$_3$, 100 MHz) δ 13.6, 24.2, 30.7, 36.0, 69.8, 93.9, 162.4, 167.9 and 169.2; mass spectrum (APCI), m/z 214.1832 (M+H)$^+$ ($C_{11}H_{12}N_3O^2H_6$ requires 214.1827).

4-Cyclobutoxy-2-(N,N-dimethylamino)-6-hexadecylpyrimidine-d₆ (52)

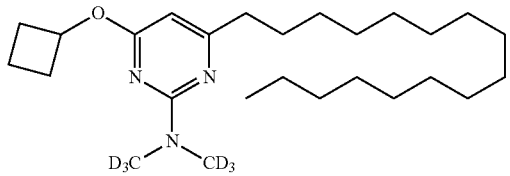 [SMILES: [2H]C([2H])([2H])N(c1nc(CCCCCCCCCCCCCCCC)cc(OC2CCC2)n1)C([2H])([2H])[2H]]

To a stirred solution containing 391 mg (1.83 mmol) of 51 in 20 mL of anhydrous THF at −78° C. was added 1.09 mL (2.74 mmol) of a 2.5 M solution of n-BuLi in hexane. The reaction mixture was stirred at −78° C. for 20 min and then 477 µL (1.64 mmol) of 1-bromopentadecane was added. The reaction was stirred at 0° C. for 15 min and then at room temperature for another 30 min. The reaction mixture was quenched with satd aq ammonium chloride and extracted with 300 mL of EtOAc. The combined organic phase was washed with brine, dried (MgSO₄) and concentrated under diminished pressure. The residue was purified by chromatography on a silica gel column (20×3 cm). Elution with 19:1 hexane-Et₂O afforded 52 as a colorless solid: yield 434 mg (56%); mp 39-40° C.; silica gel TLC $R_f$ 0.58 (4:1 hexane-Et₂O); ¹H NMR (CDCl₃, 400 MHz) δ 0.88 (t, 3H, J=7.2 Hz), 1.15-1.39 (m, 26H), 1.65 (m, 3H), 1.81 (m, 1H), 2.14 (m, 2H), 2.41 (m, 2H), 2.47 (m, 2H), 5.12 (quint, 1H, J=7.2 Hz) and 5.74 (s, 1H); ¹³C NMR (CDCl₃, 100 MHz) δ 13.7, 14.2, 22.8, 28.6, 29.48, 29.5, 29.6, 29.7, 29.8, 29.83, 30.8, 32.1, 36.0, 38.0, 69.8, 93.3, 162.4, 169.2 and 172.0; mass spectrum (APCI), m/z 424.4182 (M+H)⁺ ($C_{26}H_{42}N_3O^2H_6$ requires 424.4174).

5-Bromo-4-cyclobutoxy-2-(N,N-dimethylamino)-6-hexadecylpyrimidine-d₆ (53)

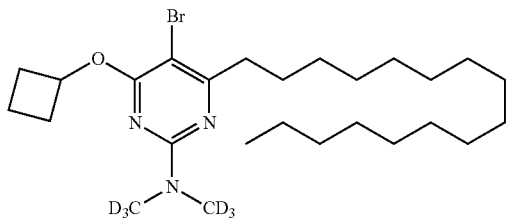

To a stirred solution containing 286 mg (0.67 mmol) of 52 in 5 mL CH₂Cl₂ was added 126 mg (0.71 mmol) of NBS under dark. The reaction mixture was stirred for 30 min at room temperature under dark, then diluted with 50 mL CH₂Cl₂, washed with brine, dried (MgSO₄) and concentrated under diminished pressure. The residue was purified by chromatography on a silica gel column (15×3 cm). Elution with hexane followed by 98:2 hexane-EtOAc afforded 53 as a colorless solid: yield 306 mg (91%); mp 57-59° C.; silica gel TLC $R_f$ 0.66 (4:1 hexane-EtOAc); ¹H NMR (CDCl₃, 400 MHz) δ 0.89 (t, 3H, J=6.8 Hz), 1.21-1.41 (m, 26H), 1.68 (m, 3H), 1.84 (m, 1H), 2.22 (m, 2H), 2.45 (m, 2H), 2.70 (m, 2H) and 5.16 (quint, 1H, J=7.2 Hz); ¹³C NMR (CDCl₃, 100 MHz) δ 13.7, 14.3, 22.9, 27.8, 29.5, 29.6, 29.64, 29.8, 29.9, 30.8, 32.1, 36.2, 37.0, 71.1, 91.4, 160.3, 164.3 and 169.2; mass spectrum (APCI), m/z 502.3274 (M+H)⁺ ($C_{26}H_{41}N_3OBr^2H_6$ requires 502.3279).

4-Cyclobutoxy-2-(N,N-dimethylamino)-6-hexadecylpyrimidin-5-ol-d₆ (13)

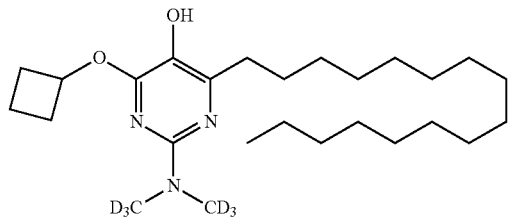 [SMILES: [2H]C([2H])([2H])N(c1nc(CCCCCCCCCCCCCCCC)c(O)c(OC2CCC2)n1)C([2H])([2H])[2H]]

To a stirred solution containing 270 mg (0.54 mmol) of 53 in 10 mL of anhydrous THF at −5° C. was added 429 µL (1.07 mmol) of a 2.5 M solution of n-BuLi in hexane and 181 µL (1.62 mmol) of trimethoxyborane. The reaction mixture was stirred at 23° C. for 30 min followed by addition of 808 µL (11.9 mmol) of H₂O₂ (50% v/v). The reaction mixture was stirred for additional 30 min, poured into 20 mL NaHCO₃ and then extracted with 100 mL of CH₂Cl₂. The combined organic phase was washed with brine, dried (MgSO₄) and concentrated under diminished pressure. The residue was purified by chromatography on a silica gel column (15×3 cm). Elution with 97:3 hexane-EtOAc afforded 13 as a colorless powder: yield 160 mg (67%); mp 72-73° C.; silica gel TLC $R_f$ 0.53 (4:1 hexane-EtOAc); ¹H NMR (CDCl₃, 400 MHz) δ 0.88 (t, 3H, J=6.8 Hz), 1.14-1.44 (m, 26H), 1.68 (m, 3H), 1.83 (m, 1H), 2.14 (m, 2H), 2.43 (m, 2H), 2.61 (m, 2H), 4.58 (br s, 1H) and 5.19 (m, 1H); ¹³C NMR (CDCl₃, 100 MHz) δ 13.7, 14.3, 22.8, 27.9, 29.5, 29.7, 29.72, 29.8, 29.82, 29.9, 31.0, 31.5, 32.1, 70.6, 127.0, 155.2, 156.2 and 157.2; mass spectrum (APCI), m/z 440.4119 (M+H)⁺ ($C_{26}H_{42}N_3O_2{}^2H_6$ requires 440.4123).

Example 13: Preparation of 4-cyclobutoxy-6-hexadecyl-2-(pyrrolidin-1-yl)pyrimidin-5-ol (14)

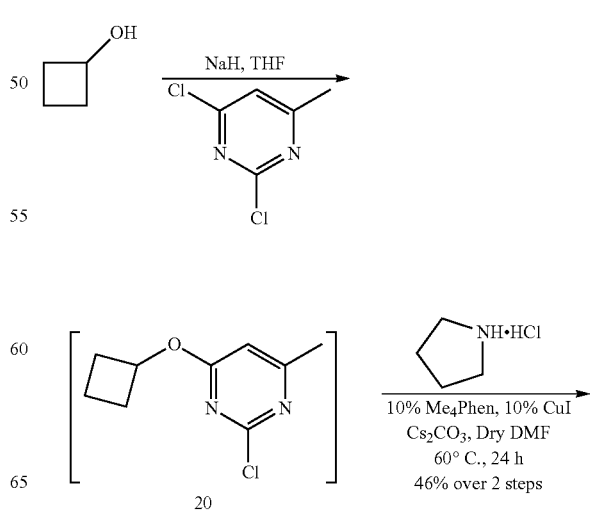

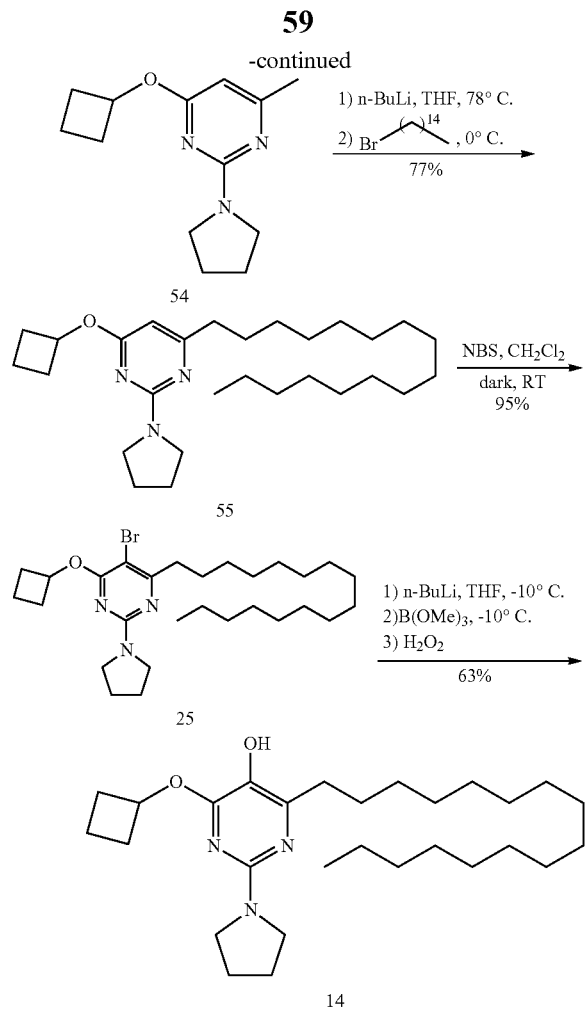

4-Cyclobutoxy-2-(pyrolidin-1-yl)-6methylpyrimidine (54)

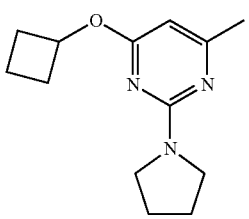 [SMILES: Cc1cc(OC2CCC2)nc(N2CCCC2)n1]

To 30 mL of previously dry and degassed DMF were added 1 g (5.00 mmol) of the crude 20, 3.25 g (10.0 mmol) of $Cs_2CO_3$ and 816 μL (10.0 mmol) of pyrolidine. The suspension was stirred under argon at room temperature for 10 min and 118 mg (0.50 mmol) of 3,4,7,8-tetramethyl-1, 10-phenanthroline and 95 mg (0.5 mmol) of copper (I) iodide where added. The reaction mixture was then warmed to 50° C. and kept under argon for 24 h. After the reaction was completed, the reaction mixture was diluted in 30 mL of ethyl acetate and filtered through Celite. The resulting filtrate was concentrated to dryness. The crude residue was purified by flash chromatography on a silica gel column (15×2 cm). Elution with 95:5 to 9:1 hexane/EtOAc afforded 54 as a colorless solid: yield 540 mg (46%); mp 47-48° C.; silica gel TLC Rf 0.2 (95:5 hexane/EtOAc); $^1$H NMR (CDCl$_3$) δ 1.58-1.7 (m, 1H, 1.75-1.83 (m, 1H), 1.91 (m, 4H), 2.06-2.18 (m, 2H), 2.24 (s, 3H), 2.35-2.45 (m, 2H), 3.53 (m, 4H), 5.08 (qt, J=7.5 Hz, 1H), 5.74 (s, 1H); $^{13}$C NMR (CDCl$_3$) δ 13.7, 24.3, 25.6, 30.9, 46.6, 69.9, 94.0, 160.6, 168.0, 169.2; HRMS (APCI+), m/z 234.1605 (M+H)+ ($C_{13}H_{20}N_3O$ requires m/z 234.1606).

4-Cyclobutoxy-2-(pyrrolidin-1-yl)-6-hexadecylpyrimidine (55)

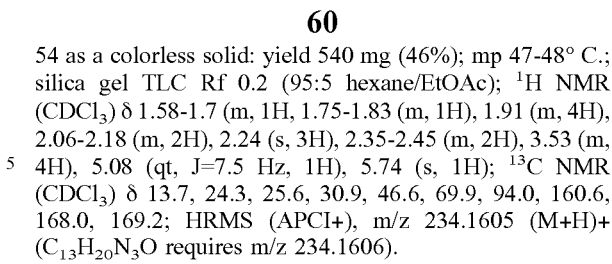

A stirred solution containing 200 mg (0.858 mmol) of 54 in 8 mL of freshly distilled THF was cooled under argon at −78° C. and kept under argon for 15 min. 562 μL (0.9 mmol) of 1.6 M solution of n-buLi in hexane was slowly added dropwise and the resulting mixture was kept under stirring at −78° C. for 1 h. 262 mg (0.9 mmol) of 1-bromohexadecane in solution in 1 mL of distilled THF were then added dropwise and the reaction was then warmed to 0° C. and stirred for 1 h. The reaction was quenched by adding 20 mL of NH$_4$Cl sat., and extracted with two portions of 20 mL of $CH_2Cl_2$. The organic phases were combined, dried over MgSO$_4$ and concentrated under diminished pressure. The residue was purified by flash chromatography on a silica gel column (15×2 cm). Elution with 98:2 to 95:5 hexane/EtOAc to afford compound 55 as a colorless solid: yield 289 mg (77%); mp 57-58° C., silica gel TLC R$_f$ 0.45 (95:5 Hexane-EtOAc); H NMR (CDCl$_3$) δ 0.88 (t, J=6.9 Hz, 3H), 1.18-1.35 (m, 26H), 1.58-1.7 (m, 3H), 1.75-1.85 (m, 1H), 1.92 (m, 4H), 2.08-2.18 (m, 2H), 2.35-2.45 (m, 2H), 2.45-2.52 (m, 2H), 2.24 (s, 3H), 2.35-2.45 (m, 2H), 3.54 (m, 4H), 5.10 (qt, J=7.5 Hz, 1H), 5.75 (s, 1H); $^{13}$C NMR (CDCl$_3$) δ 13.7, 14.2, 22.8, 25.6, 28.7, 29.5, 29.66, 29.70, 29.80, 29.84, 30.9, 32.1, 38.02, 46.6, 69.9, 93.2, 160.6, 169.2, 172.2; HRMS (APCI), m/z 444.3963 (M+H)+ ($C_{28}H_{50}N_3O$ requires m/z 444.3948).

5-Bromo-4-cyclobutoxy-2-(pyrolidin-1-yl)-6-hexadecylpyrimidine (56)

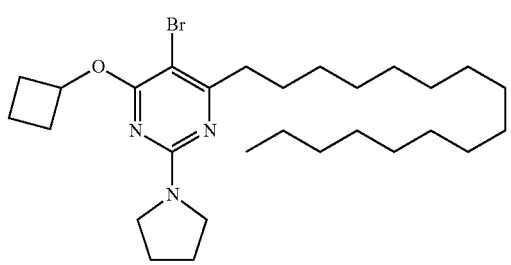 [SMILES: CCCCCCCCCCCCCCCCc1nc(N2CCCC2)nc(OC2CCC2)c1Br]

To a stirred solution containing 280 mg (0.63 mmol) of 55 in 8 mL of freshly distilled CH$_2$Cl$_2$ at room temperature in the dark was added 113 mg (0.63 mmol) of recrystallised N-bromosuccinimide. The reaction mixture was stirred under argon for 1 h. The solvent was removed under diminished pressure and the residue was purified by flash chromatography on a silica gel column (15×2 cm). Elution with 99:1 to 98:2 hexane/EtOAc to afford compound 56 as a colorless solid: yield 313 mg (95%); mp 70-71° C. silica gel TLC $R_f$ 0.55 (95:5 hexane:EtOAc); $^1$H NMR (CDCl$_3$) δ 0.88 (t, J=6.9 Hz, 3H), 1.18-1.35 (m, 26H), 1.59-1.7 (m, 3H), 1.83 (m, 1H), 1.94 (m, 4H), 2.15-2.26 (m, 2H), 2.40-2.48 (m, 2H), 2.67-2.72 (m, 4H), 3.50 (m, 4H), 5.16 (qt, J=7.5 Hz, 1H); $^{13}$C NMR (CDCl$_3$) δ 13.7, 14.3, 22.8, 25.7, 27.9, 29.5, 29.59, 29.64, 29.74, 29.81, 29.83, 29.86, 30.9, 32.1, 37.0, 46.8, 71.2, 91.3, 158.4, 164.3, 169.3; HRMS (APCI+), m/z 522.3046 (M+Na)+($C_{28}H_{49}BrN_3O$ requires m/z 522.3059).

4-Cyclobutoxy-2-(pyrrolidin-1-yl)-6-hexadecylpyrimidin-5-ol (14)

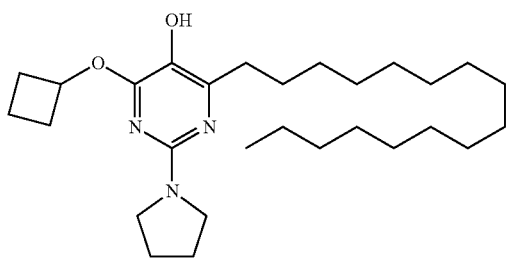 [SMILES: CCCCCCCCCCCCCCCCc1nc(N2CCCC2)nc(OC2CCC2)c1O]

A stirred solution containing 150 mg (0.287 mmol) of 56 in 4 mL of freshly distilled THF was cooled down to −10° C. and kept under argon for 10 min. To the resulting suspension was added 200 μL of 1.6 M solution of n-butyllithium in hexane (0.31 mmol) and the resulting mixture was kept under stirring at −10° C. for 1 h leading to a clear yellow solution. 70 μL (0.62 mmol) of trimethyl borate was slowly added and the reaction was kept at −10° C. for 1 more hour. 500 μL of H$_2$O$_2$ (30% v/v) was then added and the reaction was warmed to room temperature and stirred for 45 min. The reaction mixture was diluted by addition of 30 mL of saturated NH$_4$Cl and extracted with two 25 mL portions of CH$_2$Cl$_2$. The organic phase was combined, dried over MgSO$_4$ and concentrated under diminished pressure. The residue was purified by flash chromatography on a silica gel column (15×1 cm). Elution with 98:2 to 9:1 hexane/EtOAc to afford compound 14 as a colorless solid: yield 82 mg (63%); mp 74-76° C.; silica gel TLC $R_f$ 0.2 (95:5 hexane/EtOAc); $^1$H NMR (CDCl$_3$) δ $^1$H NMR (CDCl$_3$) δ 0.88 (t, J=6.9 Hz, 3H), 1.18-1.35 (m, 26H), 1.60-1.73 (m, 3H), 1.83 (m, 1H), 1.92 (m, 4H), 2.07-2.20 (m, 2H), 2.38-2.49 (m, 2H), 2.62 (m, 4H), 3.48 (m, 4H), 4.51 (brs, 1H), 5.19 (qt, J=7.5 Hz, 1H); $^{13}$C NMR (CDCl$_3$) δ 13.7, 14.3, 22.8, 25.8, 27.8, 28.1, 29.5, 29.73, 29.78, 29.81, 29.86, 31.0, 31.5, 32.1, 37.0, 46.9, 70.6, 126.9, 154.5, 155.3, 157.4; HRMS (APCI+), m/z 460.6176 (M+H)=±($C_{28}H_{50}N_3O_2$ requires m/z 460.6176).

Example 14: Preparation of 4-cyclobutoxy-6-hexadecyl-2-(piperidin-1-yl)-pyrimidin-5-ol (15)

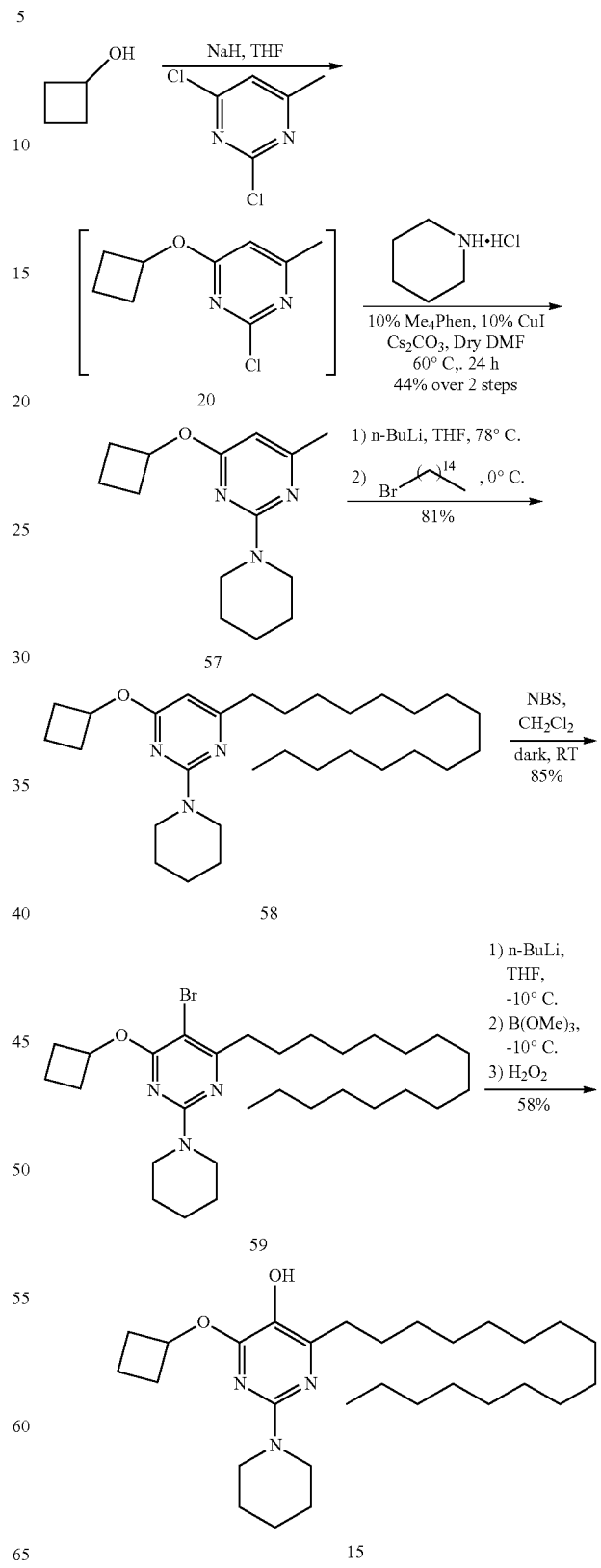

4-Cyclobutoxy-2-(piperidin-1-yl)-6-methylpyrimidine (57)

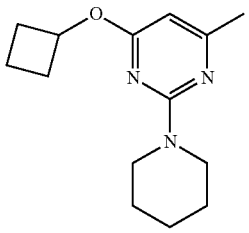 [SMILES: Cc1cc(OC2CCC2)nc(N2CCCCC2)n1]

To 30 mL of previously dry and degassed DMF was added 1.0 g (5.0 mmol) of the crude mixture of 20 and 3.25 g (10 mmol) of $Cs_2CO_3$. 990 µL (10 mmol) of piperidine was added followed by 118 mg (0.5 mmol) of 3, 4, 7, 8-tetramethyl-1,10-phenanthroline and 95 mg (0.5 mmol) of copper (I) iodide. The reaction was then warmed to 60° C. and kept under argon for 24 h. After the reaction was completed, the mixture was diluted in 30 mL of ethyl acetate and filtrated through Celite. The resulting filtrate was concentrated to dryness. The crude residue was purified by flash chromatography on a silica gel column (15×2 cm). Elution with 99:1 to 98:2 hexane/EtOAc to afford 57 as a colorless solid: yield 542 mg (44%) for two steps; mp 49-50° C.; silica gel TLC $R_f$ 0.45 (95:5 Hexane-EtOAc); $^1$H NMR (CDCl$_3$) δ 1.52-1.7 (m, 7H), 1.75-1.86 (m, 1H), 1.91 (m, 4H), 2.06-2.18 (m, 2H), 2.23 (s, 3H), 2.35-2.45 (m, 2H), 3.74 (m, 4H), 5.08 (qt, J=7.4 Hz, 1H), 5.73 (s, 1H); $^{13}$C NMR (CDCl$_3$) δ 13.7, 24.3, 25.1, 30.8, 44.9, 69.8, 94.2, 161.8, 168.1, 169.4; HRMS (APCI+), m/z 248.1766 (M+H)$^+$ ($C_{14}H_{22}N_3O$ requires m/z 248.1763).

4-Cyclobutoxy-2-(piperidin-1-yl)-6-hexadecylpyrimidine (58)

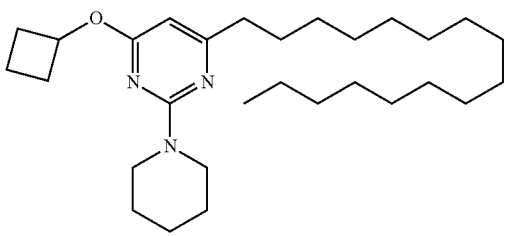 [SMILES: CCCCCCCCCCCCCCCCc1cc(OC2CCC2)nc(N2CCCCC2)n1]

A stirred solution containing 200 mg (0.81 mmol) of 57 in 8 mL of freshly distilled THF was cooled under argon at −78° C. and kept under argon for 15 min. 530 µL (0.84 mmol) of a 1.6 M solution of n-BuLi in hexane was slowly added dropwise and the resulting reaction mixture was stirred at −78° C. for 1 h. 245 mg (0.84 mmol) of 1-bromohexadecane in 1 mL of distilled THF was added dropwise and the reaction mixture was warmed to 0° C. and stirred for 1 h. The reaction was quenched by adding 20 mL of saturated NH$_4$Cl and extracted with two 20 mL portions of CH$_2$Cl$_2$. The combined organic phase was dried over MgSO$_4$ and concentrated under diminished pressure. The residue was purified by flash chromatography on a silica gel column (15×2 cm). Elution with 98:2 hexane/EtOAc to afford compound 58 as a colorless oil: yield 298 mg (81%); mp 42-43° C.; silica gel TLC $R_f$ 0.65 (95:5 Hexane:EtOAc); $^1$H NMR (CDCl$_3$) δ 0.88 (t, J=7.0 Hz, 3H), 1.2-1.37 (m, 26H), 1.53-1.7 (m, 9H), 1.75-1.86 (m, 1H), 1.91 (m, 4H), 2.08-2.19 (m, 2H), 2.37-2.43 (m, 2H), 2.43-2.51 (m, 2H), 3.75 (m, 4H), 5.09 (qt, J=7.4 Hz, 1H), 5.73 (s, 1H); $^{13}$C NMR (CDCl$_3$) δ 13.7, 14.2, 22.8, 25.1, 25.9, 28.6, 29.5, 29.6, 29.7, 29.82, 29.85, 30.8, 32.1, 38.0, 44.9, 69.8, 93.6, 161.9, 169.4, 172.2; HRMS (APCI+), m/z 458.4110 (M+H)$^+$ ($C_{29}H_{52}N_3O$ requires m/z 458.110).

5-Bromo-4-cyclobutoxy-2-(piperidin-1-yl)-6-hexadecylpyrimidine (59)

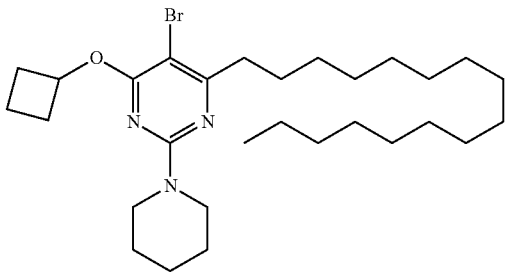 [SMILES: CCCCCCCCCCCCCCCCc1nc(N2CCCCC2)nc(OC2CCC2)c1Br]

To a stirred solution containing 290 mg (0.634 mmol) of 58 in 8 mL of freshly distilled CH$_2$Cl$_2$ at room temperature under darkness was added 114 mg (0.634 mmol) of recrystallised N-bromosuccinimide. The reaction mixture was stirred under argon for 1 h. The solvent was removed under reduced pressure and the resulting residue was purified by flash chromatography on a silica gel column (15×2 cm). Elution with 99:1 to 98:2 hexane/EtOAc to afford compound 59 as a colorless solid: yield 288 mg (85%); mp 60-61° C. silica gel TLC $R_f$ 0.7 (95:5 hexane/EtOAc); $^1$H NMR (CDCl$_3$) δ 0.88 (t, J=7.0 Hz, 3H), 1.22-1.39 (m, 26H), 1.53-1.59 (m, 4H), 1.60-1.71 (m, 5H), 1.79-1.88 (m, 1H), 2.15-2.25 (m, 2H), 2.40-2.48 (m, 2H), 2.43-2.51 (m, 2H), 2.68 (m, 2H), 3.71 (m, 4H), 5.14 (qt, J=7.4 Hz, 1H); $^{13}$C NMR (CDCl$_3$) δ 13.7, 14.3, 22.8, 25.0, 25.8, 27.7, 29.57, 29.63, 29.76, 29.86, 30.8, 32.1, 37.0, 45.1, 71.1, 91.3, 159.6, 164.4, 169.2; HRMS (APCI+), m/z 536.3216 (M+H)+ ($C_{29}H_{51}BrN_3O$ requires m/z 536.3215).

4-Cyclobutoxy-2-(piperidin-1-yl)-6-hexadecylpyrimidin-5-ol (15)

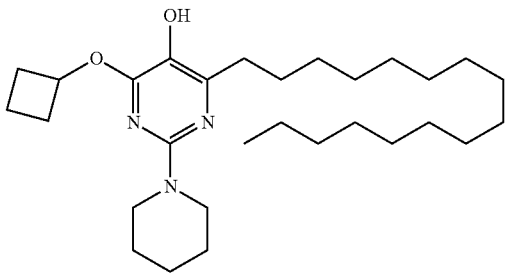 [SMILES: CCCCCCCCCCCCCCCCc1nc(N2CCCCC2)nc(OC2CCC2)c1O]

A stirred solution containing 150 mg (0.28 mmol) of 59 in 4 mL of freshly distilled THF was cooled to −10° C. and kept under argon for 10 min. To the resulting suspension was added 193 µL of a 1.6 M solution of n-butyllithium in hexane (0.31 mmol) and the resulting reaction mixture was stirred at −10° C. for 1 h, leading to a clear yellow solution.

67 µL (0.6 mmol) of trimethyl borate was slowly added and the reaction was kept at −10° C. for 1 more hour. 500 µL of $H_2O_2$ (30% v/v) was added and the reaction mixture was warmed to room temperature and stirred for 45 min. The mixture was diluted, by addition of 30 mL of saturated $NH_4Cl$, and extracted with two 25 mL portions of $CH_2Cl_2$. The combined organic phase was dried over $MgSO_4$ and concentrated under diminished pressure. The residue was purified by flash chromatography on a silica gel column (15×1 cm). Elution with 98:2 to 9:1 hexane/EtOAc to afford compound 15 as a colorless solid: yield 83 mg (58%); mp 78-79° C.; silica gel TLC $R_f$ 0.35 (95:5 hexane/EtOAc); $^1H$ NMR ($CDCl_3$) δ 0.88 (t, J=7.0 Hz, 3H), 1.22-1.39 (m, 26H), 1.52-1.70 (m, 9H), 1.79-1.88 (m, 1H), 2.09-2.20 (m, 2H), 2.39-2.48 (m, 2H), 2.60 (m, 2H), 3.63 (m, 4H), 4.46 (brs, 1H), 5.18 (qt, J=7.5 Hz, 1H); $^{13}C$ NMR ($CDCl_3$) δ 13.6, 14.3, 22.8, 25.1, 25.8, 27.8, 29.52, 29.68, 29.70, 29.78, 29.82, 29.86, 30.9, 31.5, 32.1, 45.6, 70.6, 127.3, 155.0, 155.6, 157.2; HRMS (APCI+), m/z 474.4039 $(M+H)^+$ ($C_{29}H_{52}N_3O_2$ requires m/z 474.4060).

Biochemical and Biological Evaluation

Cell Lines and Culture Conditions

Human mitochondrial disease cell line, Friedreich's ataxia lymphocytes (GM15850) was obtained from Coriell Cell Repositories (Camden, N.J.). Lymphocytes were cultured in RPMI-1640 medium (Gibco, Life Technologies, Grand Island, N.Y.) with 15% fetal calf serum, 2 mM glutamine (HyClone, South Logan, Utah) and 1% penicillin-streptomycin antibiotic supplement (Cellgro, Manassas, Va.). Cells were passaged every other day to maintain them in log phase growth and kept at a nominal concentration of $5-10\times10^5$ cell/mL. A $CoQ_{10}$ deficient lymphocyte cell line (GM17932) was obtained from Coriell Cell Repositories. A nutrient sensitized screening strategy to identify $CoQ_{10}$ analogues that function within the mitochondrial respiratory chain was used by growing the $CoQ_{10}$-deficient or FRDA lymphocytes in galactose containing media to force energy production predominantly through oxidative phosphorylation rather than glycolysis. The lymphocytes were cultured in RPMI 1640 glucose free medium (Gibco, Grand Island, N.Y.) supplemented with 25 mM galactose, 2 mM glutamine and 1% penicillin-streptomycin, and 10% dialyzed fetal bovine serum (FBS) (<0.5 µg/mL) (Gemini Bio-Product, West Sacramento, Calif.).

Example 15: Inhibition of Lipid Peroxidation

The ability of the compounds disclosed herein (e.g., pyrimidinol analogues) to quench lipid peroxidation was studied in FRDA lymphocytes that had been depleted of glutathione by treatment with diethyl maleate (DEM). $C_{11}$-BODIPY$^{581/591}$, a hydrophobic fatty acid fluorophore which inserts preferentially in membranes, has been shown previously to enable quantification of fatty acid oxidation and antioxidant activity in live cells. The oxidation of the polyunsaturated butadienyl portion of the dye results in a shift of the fluorescence emission peak from red to green. The degree of probe oxidation was followed using flow cytometry as reported before (Post et al. (1999) FEBS Lett. 453, 278; Arce et al. (2012) Bioorg. Med. Chem. 20, 5188). Cells were analyzed for a shift of the fluorescence emission peak from red to green with excitation/emission wavelengths of 490/510 nm. The median mean fluorescence values were used for further analysis. Increasing green fluorescence intensity indicated lipid peroxidation. Briefly, FRDA lymphocytes ($5\times10^5$ cell/mL) were plated (1 mL in 24-well plates), treated with the test compounds and incubated at 37° C. for 16 h in a humidified atmosphere containing 5% $CO_2$ in air. The following day, cells were treated with 1 µM of $C_{11}$-BODIPY$^{581/591}$ probe in phenol red-free media and incubated at 37° C. in the dark for 30 min. Oxidative stress was induced with 5 mM DEM in phenol red-free RPMI-1640 media for 120 min. Cells were collected by centrifugation at 300×g for 3 min and then washed with phosphate buffered saline (PBS). Cells were resuspended in phosphate buffered saline and were analyzed immediately by FACS (C6 Accuri, BD Biosciences, San Jose, Calif.), using a 488 nm excitation laser and the FL1-H channel 530±15 nm emission filter. The generation of lipid peroxide was detected as a result of the oxidation of the polyunsaturated butadienyl portion of the dye, resulting in a shift of the fluorescence emission peak from red to green. In each analysis, 10,000 events were recorded after cell debris were electronically gated out. Results were expressed as a percentage of lipid peroxidation scavenging activity.

Example 16: Suppression of Reactive Oxygen Species

The ability of the pyridinol and pyrimidinol analogues to suppress ROS induced by depletion of glutathione was evaluated in FRDA lymphocyte cells. The intracellular ROS level was measured based on the ROS-induced formation of the highly fluorescent product 2',7'-dichlorofluorescein (DCF) from the non-fluorescent dye 2',7'-dichlorodihydrofluorescein diacetate (DCFH-DA). Briefly, 1 mL of FRDA lymphocytes ($5\times10^5$ cells) was plated in a 24-well plate, treated with the test compounds and incubated at 37° C. for 16 h in a humidified atmosphere containing 5% $CO_2$ in air. Cells were treated with 5 mM diethyl maleate (DEM) for 80 min, collected by centrifugation at 300×g for 3 min and then washed with phosphate buffered saline (Life Technologies). Cells were resuspended in PBS containing 20 mM glucose and incubated at 37° C. in the dark for 25 min with 10 µM DCFH-DA. Cells were collected by centrifugation at 300×g for 3 min and then washed with PBS. The samples were analyzed immediately by flow cytometry (C6 Accuri, BD Biosciences, San Jose, Calif.), using a 488 nm excitation laser and the FL1-H channel 530±15 nm emission filter. The generation of ROS, mainly peroxides, was detected as a result of the oxidation of DCFH. In each analysis, 10,000 events were recorded after cell debris was electronically gated out. Results obtained were verified by running duplicates and repeating experiments in three independent runs. Results were expressed as a percentage of ROS scavenging activity.

Example 17: Preservation of Mitochondrial Membrane Potential ($\Delta\psi_m$)

The ability of the test compounds to maintain mitochondrial inner membrane potential ($\Delta\psi_m$) under conditions of oxidative stress was studied as described previously. $\Delta\psi_m$ was measured using tetramethylrhodamine methyl ester (TMRM), a lipophilic cation that accumulates selectively within polarized mitochondria. The extent of its uptake, as measured by intensity of cellular TMRM red fluorescence, is proportional to mitochondrial function (Ehrenberg et al. (1988) Biophys. J. 53, 785). Therefore, the accumulation of dye in the mitochondria and the intensity of the signal is a direct function of mitochondrial potential. Mitochondrial depolarization then causes the redistribution of dye from mitochondria into the cytosol, causing a change in signal intensity. The detection of mitochondrial depolarization using TMRM was accomplished by flow cytometry as described before (Arce et al. (2012) *Bioorg. Med. Chem.* 20, 5188). Briefly, FRDA lymphocytes cells ($5 \times 10^5$ cells) were pre-treated with or without the test compounds for 16 h. The cells were treated with 5 mM DEM for 120 min, collected by centrifugation at 300×g for 3 min and washed with phosphate buffered saline. The cells were resuspended in PBS containing 20 mM glucose and incubated at 37° C. in the dark for 15 min with 250 nM TMRM. Cells were collected by centrifugation at 300×g for 3 min and washed with phosphate buffered saline. Cells were resuspended in phosphate buffered saline supplemented with 20 mM glucose and were analyzed immediately by FACS (C6 Accuri, BD Biosciences, San Jose, Calif.), using a 488 nm excitation laser and the FL2-H channel. For each analysis 10,000 events were recorded and the percentage of cells exhibiting a high level of TMRM uptake, which reflects normal mitochondrial membrane potential, was determined and analyzed using C6 Accuri software (BD Biosciences). FCCP (carbonyl cyanide p-trifluoromethoxyphenyl hydrazone), a mitochondrial uncouple, was used to produce a negative control.

Example 18: Cellular ATP Levels

A nutrient-sensitized screening strategy to identify $CoQ_{10}$ analogues that function within the mitochondrial respiratory chain and augment ATP was used as described before (Khdour et al. (2013) *ACS Med. Chem. Lett.* 4, 724). The intracellular ATP level was measured in glucose-free media. The cells were grown on galactose-containing media to maximize ATP production via oxidative phosphorylation, and they become more sensitive to mitochondrial respiratory chain inhibitors than cells grown on glucose medium. Briefly, $CoQ_{10}$ deficient lymphocytes ($2 \times 10^5$ cell/mL) were plated (1 mL in 24-well plates) in glucose-free media supplemented with galactose and treated with the test compounds at final concentrations of 5, 10, and 25 M, and then incubated at 37° C. for 48 h in a humidified atmosphere containing 5% $CO_2$ in air. Wells were mixed and cells in each well were transferred (100 µL) to 96-well microtiter black-walled cell culture plates (Costar, Corning, N.Y.). The total intracellular ATP level was measured in a luminator (Clarity™ luminescence microplate reader) using an ATP Bioluminescence Assay Kit (ViaLight-Plus ATP monitoring reagent kit, Lonza, Walkersville, Md.) following the manufacturer's protocol. The total ATP level was expressed as a percentage of untreated control.

Example 19: Cytoprotection

Trypan Blue Exclusion Assay

The cytoprotection conferred by the compounds disclosed herein was determined in FRDA lymphocyte using the trypan blue exclusion method. This method is used to determine the number of viable cells present in cell suspension. It is based on the principle that live cells possess intact cell membranes that exclude trypan blue, whereas dead cells are not capable of excluding trypan blue. Briefly, lymphocytes were seeded at a density of $5 \times 10^5$ cells per mL and treated with different concentrations of the test compounds. Cells were incubated at 37° C. in a humidified atmosphere of 5% $CO_2$ in air for 16 h. Oxidative stress was then induced by 5 mM diethyl maleate (DEM) treatment for 6 h. Cell viability was assessed microscopically by the use of a hemocytometer. The number of cells that absorbed the dye and those that excluded the dye were counted, from which the percentage of nonviable cell number over total cell number was calculated. Cytoprotection by the test compounds was assessed with respect to the untreated controls. Cells not treated with DEM had >90% cell viability whereas DEM treatment reduced cell viability to <20%. The cell viability was expressed relative to the vehicle control (DMSO only) group (n=3).

FACS Analysis LIVE/DEAD® Viability/Cytotoxicity Assay

The viability of DEM-treated FRDA lymphocyte cells was determined by using a simultaneous staining with a two-color fluorescence assay, the LIVE/DEAD® Viability/Cytotoxicity Kit (Molecular Probes). This assay is used to measure two recognized parameters of cell viability, intracellular esterase activity and plasma integrity. The membrane-impermeant DNA dye ethidium homodimer-1 (EthD-1) was used to identify dead cells whose plasma membrane integrity was disrupted. The membrane-permeant dye calcein-AM was used to label live cells. It penetrates into the cells where it is metabolized by cytoplasmic esterases and becomes a fluorescent but membrane-impermeant probe which is retained in viable cells. Briefly, FRDA lymphocyte cells were seeded at a density of $5 \times 10^5$ cells/mL and treated with different concentrations of the test compounds. Cells were incubated at 37 C in a humidified atmosphere of 5% CO2 in air for 16 h. Oxidative stress was then induced by incubation with 5 mM DEM for 6 h, followed by evaluation of cytoprotection. Cells were collected by centrifugation at 300×g for 3 min and washed with phosphate buffered saline. Cells were resuspended in phosphate buffered saline containing 25 mM galactose. Cell suspension was stained with 0.1 µM calcein AM and 0.2 µM EthD-1 and incubated in the dark at 37° C. for 15 minutes. Cells were collected by centrifugation at 300×g for 3 min and then washed with PBS. The samples were analyzed immediately by flow cytometry (C6 Accuri, BD Biosciences, San Jose, Calif.), using a 488 nm excitation laser and the and the FL1-H channel 530±15 nm emission filter and the FL2-H channel 585±15 nm. For each analysis 10,000 events were recorded and analyzed using C6 Accuri software (BD Biosciences).

Example 20: Microsomal Enzyme Preparation

Bovine liver microsomes were prepared from liver of a freshly slaughtered animal as previously reported, with some modifications (Moubarak et al. (2000) *Biochem. Biophys. Res. Commun.* 274, 746). Briefly, liver tissues were diced into small pieces and then washed with isotonic sucrose buffer (0.25 M sucrose, 10 mM Tris-HCl, 0.5 mM EDTA, pH 7.8). The diced tissue was passed through a precooled meat grinder and mixed with three-fold ice cold sucrose buffer supplemented with a mixture of protease inhibitors. The suspension was homogenized in a Waring blender for 25 sec at high speed. At this stage, the pH of the suspension was adjusted to 7.4 with 1 M Tris base. The homogenate was centrifuged for 20 min at 1200×g to remove cell debris. The supernatant suspension was homogenized in a tight fitting Teflon-glass Potter-Elvejhem homogenizer and then centrifuged twice at 10 000×g for 20 min, collecting the supernatant each time to remove mitochondria. The floating fat layer was carefully removed by filtering the supernatant through layers of cheesecloth. The supernatant was centrifuged at 150000×g for 30 min (Beckman-Coulter ultracentrifuge, XL-100K-01, SW 55 Ti rotor). The pellet (microsomal fraction) was suspended in 0.25 M sucrose buffer containing 10 mM Tris-HCl, pH 7.4, with 20% (v/v) glycerol, and centrifuged once more at 150000×g. The pellet was resuspended in sucrose buffer with 20% (v/v) glycerol. The protein concentration after resuspension was approximately 20 mg/mL, as determined by BCA protein assay (Pierce Chemical) using bovine serum albumin as a standard. Aliquots of microsomal suspensions were stored at −80° C.

Example 21: Microsomal Stability Assay

Potential drug candidates are expected to exhibit pharmacokinetic parameters consistent with reasonable bioavailability. In vitro drug metabolism studies during drug discovery can be an important part of lead optimization. The metabolic fate of many orally administered drugs is often a function of clearance in the liver. Accordingly, in vitro microsomal studies were carried out using bovine liver microsomes to identify the metabolic liabilities of the pyridinol and pyrimidinol analogues. In vitro metabolic stability was determined in bovine liver microsomes at a protein concentration of 1 mg/mL in 50 mM phosphate buffer mixture, pH 7.4, containing 5 mM $MgCl_2$ in a final incubation volume of 0.5 mL. Each test compound was added to a final concentration of 25 µM. This mixture was pre-warmed to 37° C. prior to starting the reaction with the addition of β-NADPH to 1 mM final concentration. After incubation for 30 min at 37° C., the reaction was quenched by the addition of 1 mL of propanol, vortexed for 2 min and centrifuged at 15000×g for 10 min to pellet the precipitated protein. The resulting supernatant was pipetted out and then concentrated under diminished pressure. A parallel incubation of the test compound with deactivated microsomes (quenched immediately with propanol) lacking β-NADPH served as a control and was run for each test agent to detect microsomal-independent degradation. The sample was reconstituted in 130 µL MeOH and centrifuged again at 15000×g for 3 min. The supernatant was removed and 4 µM fluorene was added as an internal standard before HPLC analysis. HPLC analyses were performed on a reversed phase Zorbax SB-Phenyl reversed phase analytical (150×4.6 mm, 5 µm) HPLC column using a mobile phase consisting of $MeOH/H_2O$. A linear gradient of (50:50 $MeOH/H_2O \rightarrow 100:0$ $MeOH/H_2O$) was employed over a period of 14 min at a flow rate of 1 mL/min. Metabolic stability was expressed as percent of control remaining. The experiments were carried out in duplicate to verify the results.

Example 22: Animal Study Information

Bioavailability is an important characteristic of many therapeutic agents. Accordingly, certain compounds disclosed herein were tested for bioavailability in a mouse model.

The test compound was prepared on the day of dose administration by dissolving the appropriate amount of test article in olive oil to reach the proper concentrations.

The dose of 100 mg/kg body weight (total volume of administration was <120 µL) was used for testing. For example, a mouse whose body weight is 20 g would need 2 mg of test article in oral gavage. Mice were food deprived overnight. On the experimental day, mice were weighed to obtain dosage information before oral gavage was performed. Blood and brain samples were collected at the desired post-dose time points after oral gavage. Brain samples were perfused to exclude blood as a factor in the analysis of bioavailability. Compound 12 was quantified in a blood sample after 6 h from oral gavage by HPLC and it was found to be present at a concentration of about 4 µM.

Example 23

The following illustrate representative pharmaceutical dosage forms, containing a compound of formula I ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |

-continued

| (vi) Aerosol | mg/can |
|---|---|
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

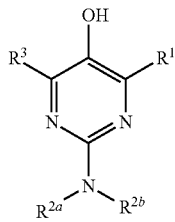

wherein:
R$^1$ is (C$_6$-C$_{26}$)alkyl, (C$_6$-C$_{26}$)alkenyl, (C$_6$-C$_{26}$)alkynyl, —O(C$_6$-C$_{26}$)alkyl, —O(C$_6$-C$_{26}$)alkenyl or —O(C$_6$-C$_{26}$)alkynyl, wherein any (C$_6$-C$_{26}$)alkyl, (C$_6$-C$_{26}$)alkenyl, (C$_6$-C$_{26}$)alkynyl, —O(C$_6$-C$_{26}$)alkyl, —O(C$_6$-C$_{26}$)alkenyl or —O(C$_6$-C$_{26}$)alkynyl of R$^1$ is optionally substituted with one or more groups independently selected from halogen, CN, NO$_2$, —OR$^{a1}$, —N(R$^{b1}$)$_2$, —CO$_2$R$^{a1}$ and —CON(R$^{b1}$)$_2$;

R$^{2a}$ and R$^{2b}$ are each independently hydrogen, (C$_1$-C$_6$)alkyl, (C$_2$-C$_6$)alkenyl or (C$_2$-C$_6$)alkynyl, wherein any (C$_1$-C$_6$)alkyl, (C$_2$-C$_6$)alkenyl or (C$_2$-C$_6$)alkynyl of R$^{2a}$ and R$^{2b}$ is optionally substituted with one or more groups independently selected from halogen, CN, NO$_2$, —OR$^{a2}$, —N(R$^{b2}$)$_2$, —CO$_2$R$^{a2}$ and —CON(R$^{b2}$)$_2$; or R$^{2a}$ and R$^{2b}$ together with the nitrogen to which they are attached form a 3-7 membered heterocyclyl, wherein the heterocyclyl is optionally substituted with one more groups independently selected from halogen, (C$_1$-C$_6$)alkyl, (C$_2$-C$_6$)alkenyl, (C$_2$-C$_6$)alkynyl, CN, NO$_2$, —OR$^{a2}$, —N(R$^{b2}$)$_2$, —CO$_2$R$^{a2}$ and —CON(R$^{b2}$)$_2$;

R$^3$ is a carbocyclyl or -Ocarbocyclyl, wherein any carbocyclyl or -Ocarbocyclyl of R$^3$ is optionally substituted with one or more groups independently selected from halogen, CN, NO$_2$, —OR$^{a3}$, —N(R$^{b3}$)$_2$, —CO$_2$R$^{a3}$ and —CON(R$^{b3}$)$_2$;

each R$^{a1}$ is independently hydrogen, (C$_1$-C$_6$)alkyl, (C$_2$-C$_6$)alkenyl, (C$_2$-C$_6$)alkynyl or (C$_3$-C$_7$)carbocyclyl, wherein any (C$_1$-C$_6$)alkyl, (C$_2$-C$_6$)alkenyl, (C$_2$-C$_6$)alkynyl or (C$_3$-C$_7$)carbocyclyl of R$^{a1}$ is optionally substituted with one more halogen;

each R$^{b1}$ is independently hydrogen, (C$_1$-C$_6$)alkyl, (C$_2$-C$_6$)alkenyl, (C$_2$-C$_6$)alkynyl or (C$_3$-C$_7$)carbocyclyl, wherein any (C$_1$-C$_6$)alkyl, (C$_2$-C$_6$)alkenyl, (C$_2$-C$_6$)alkynyl or (C$_3$-C$_7$)carbocyclyl of R$^{b1}$ is optionally substituted with one more halogen, or two R$^{b1}$ groups together with the nitrogen to which they are attached form a 3-7 membered heterocyclyl optionally substituted with one or more halogen;

each R$^{a2}$ is independently hydrogen, (C$_1$-C$_6$)alkyl, (C$_2$-C$_6$)alkenyl, (C$_2$-C$_6$)alkynyl or (C$_3$-C$_7$)carbocyclyl, wherein any (C$_1$-C$_6$)alkyl, (C$_2$-C$_6$)alkenyl, (C$_2$-C$_6$)alkynyl or (C$_3$-C$_7$)carbocyclyl of R$^{a2}$ is optionally substituted with one more halogen;

each R$^{b2}$ is independently hydrogen, (C$_1$-C$_6$)alkyl, (C$_2$-C$_6$)alkenyl, (C$_2$-C$_6$)alkynyl or (C$_3$-C$_7$)carbocyclyl, wherein any (C$_1$-C$_6$)alkyl, (C$_2$-C$_6$)alkenyl, (C$_2$-C$_6$)alkynyl or (C$_3$-C$_7$)carbocyclyl of R$^{b2}$ is optionally substituted with one more halogen, or two R$^{b2}$ groups together with the nitrogen to which they are attached form a 3-7 membered heterocyclyl optionally substituted with one or more halogen;

each R$^{a3}$ is independently hydrogen, (C$_1$-C$_6$)alkyl, (C$_2$-C$_6$)alkenyl, (C$_2$-C$_6$)alkynyl or (C$_3$-C$_7$)carbocyclyl, wherein any (C$_1$-C$_6$)alkyl, (C$_2$-C$_6$)alkenyl, (C$_2$-C$_6$)alkynyl or (C$_3$-C$_7$)carbocyclyl of R$^{a3}$ is optionally substituted with one more halogen;

each R$^{b3}$ is independently hydrogen, (C$_1$-C$_6$)alkyl, (C$_2$-C$_6$)alkenyl, (C$_2$-C$_6$)alkynyl or (C$_3$-C$_7$)carbocyclyl, wherein any (C$_1$-C$_6$)alkyl, (C$_2$-C$_6$)alkenyl, (C$_2$-C$_6$)alkynyl or (C$_3$-C$_7$)carbocyclyl of R$^{b3}$ is optionally substituted with one more halogen, or two R$^{b3}$ groups together with the nitrogen to which they are attached form a 3-7 membered heterocyclyl optionally substituted with one or more halogen; and one or more carbons of formula I is optionally deuterated;
or a salt thereof.

2. The compound of claim 1, wherein R$^1$ is (C$_6$-C$_{26}$)alkyl or —O(C$_6$-C$_{26}$)alkyl, wherein any (C$_6$-C$_{26}$)alkyl of R$^1$ is optionally substituted with one or more groups independently selected from halogen, CN, NO$_2$, —OR$^{a1}$, —N(R$^{b1}$)$_2$, —CO$_2$R$^{a1}$ and —CON(R$^{b1}$)$_2$.

3. The compound of claim 1, wherein R$^1$ is (C$_6$-C$_{26}$)alkyl, wherein any (C$_6$-C$_{26}$)alkyl of R$^1$ is optionally substituted with one or more groups independently selected from halogen, CN, NO$_2$, —OR$^{a1}$, —N(R$^{b1}$)$_2$, —CO$_2$R$^{a1}$ and —CON(R$^{b1}$)$_2$.

4. The compound of claim 1, wherein R$^1$ is (C$_{12}$-C$_{20}$)alkyl, wherein any (C$_{12}$-C$_{20}$)alkyl of R$^1$ is optionally substituted with one or more groups independently selected from halogen, CN, NO$_2$, —OR$^{a1}$, —N(R$^{b1}$)$_2$, —CO$_2$R$^{a1}$ and —CON(R$^{b1}$)$_2$.

5. The compound of claim 1, wherein R$^1$ is (C$_{12}$-C$_{20}$)alkyl.

6. The compound of claim 1, wherein R$^{2a}$ and R$^{2b}$ are each independently (C$_1$-C$_6$)alkyl, wherein any (C$_1$-C$_6$)alkyl of R$^{2a}$ and R$^{2b}$ is optionally substituted with one or more groups independently selected from halogen, CN, NO$_2$, —OR, —N(R$^{b2}$)$_2$, —CO$_2$R$^{a2}$ and —CON(R$^{b2}$)$_2$; or R$^{2a}$ and R$^{2b}$ together with the nitrogen to which they are attached form a 3-7 membered heterocyclyl, wherein the heterocyclyl is optionally substituted with one more groups independently selected from halogen, (C$_1$-C$_6$)alkyl, (C$_2$-C$_6$)alkenyl, (C$_2$-C$_6$)alkynyl, CN, NO$_2$, —OR$^{a2}$, —N(R$^{b2}$)$_2$, —CO$_2$R$^{a2}$ and —CON(R$^{b2}$)$_2$.

7. The compound of claim 1, wherein R$^{2a}$ and R$^{2b}$ are each independently (C$_1$-C$_6$)alkyl; or R$^{2a}$ and R$^{2b}$ together with the nitrogen to which they are attached form a 3-7 membered heterocyclyl.

8. The compound of claim 1, wherein —NR$^{2a}$R$^{2b}$ is

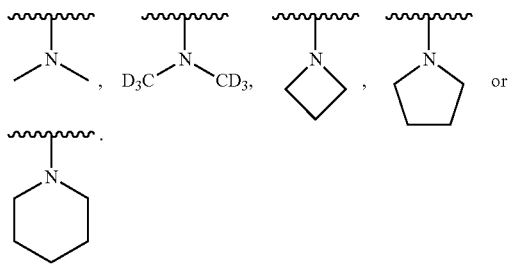

9. The compound of claim 1, wherein R$^3$ is a carbocyclyl or -Ocarbocyclyl.

10. The compound of claim 1, wherein R$^3$ is —O(C$_3$-C$_7$)carbocyclyl, wherein any —O(C$_3$-C$_7$)carbocyclyl is optionally substituted with one or more groups independently selected from halogen, CN, NO$_2$, —OR$^{a3}$, —N(R$^{b3}$)$_2$, —CO$_2$R$^{a3}$ and —CON(R$^{b3}$)$_2$.

11. The compound of claim 1, wherein R$^3$ is:

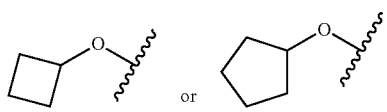

12. The compound of claim 1, wherein one or more carbons of the compound of formula I is deuterated.

13. The compound of claim 1, wherein R$^1$ is

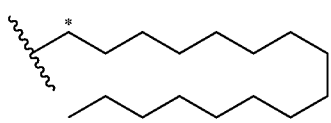 [SMILES: *CCCCCCCCCCCCCCCC]

wherein the carbon marked * is deuterated.

14. The compound of claim 1, wherein —NR$^{2a}$R$^{2b}$ is

wherein the carbons marked * are deuterated.

15. The compound of claim 1 which is:

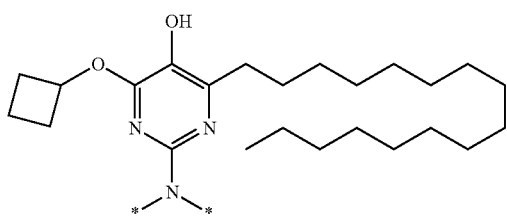

or a salt thereof, wherein the carbons marked * are deuterated.

16. The compound of claim 1 which is:

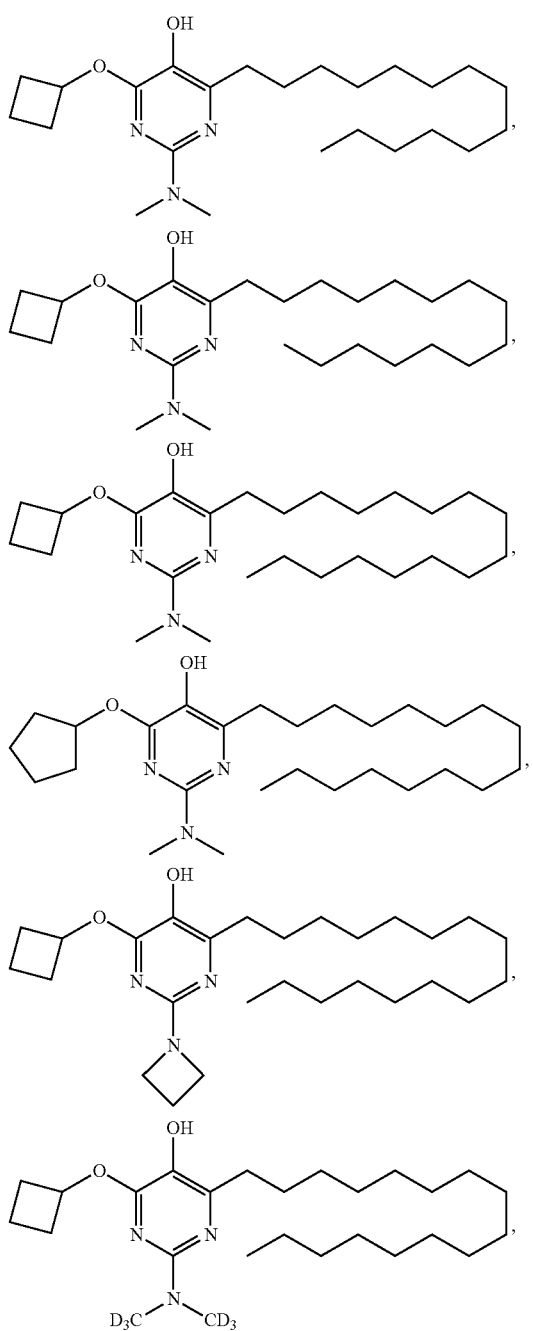

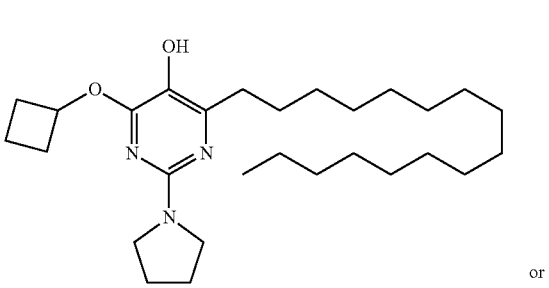

or

-continued

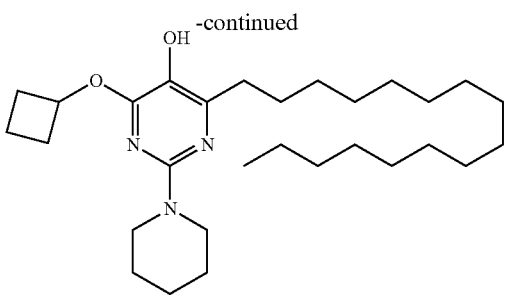

or a salt thereof.

17. The compound:

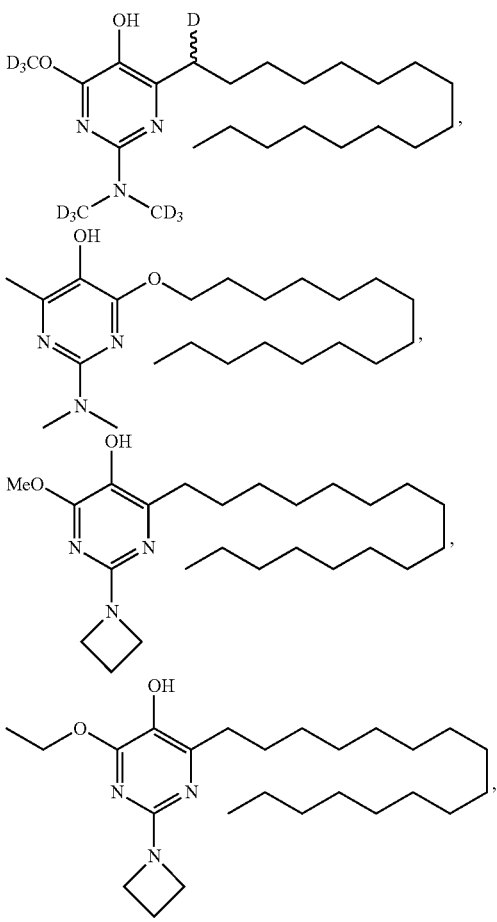

-continued

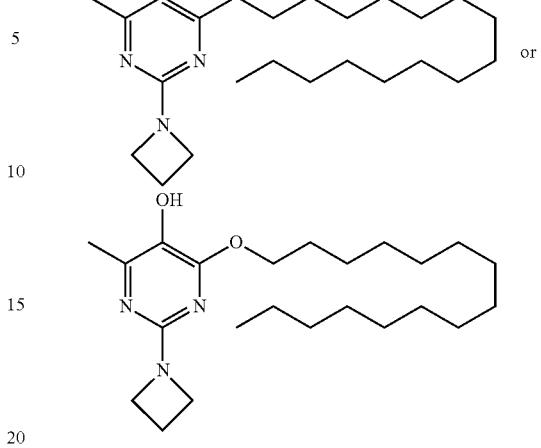

or a salt thereof.

18. The compound of claim 17, wherein the deuterium of the carbons bearing the deuterium (D) are enriched in deuterium with a minimum isotopic enrichment factor of at least 3000.

19. A pharmaceutical composition comprising a compound of formula I as described in claim 1, or a pharmaceutically acceptable salt thereof and a pharmaceutically acceptable carrier.

20. A method of treating a mitochondrial disease, obesity, heart disease, Parkinsons's disease, Alzheimer's disease, Huntington's disease, cancer, fragile X syndrome or chronic fatigue syndrome in an animal comprising administering to the animal in need thereof a compound of formula I as described in claim 1 or a pharmaceutically acceptable salt thereof.

21. A method of treating Friedreich's ataxia, Leber's hereditary optic neuropathy, Kearns-Sayre Syndrome, mitochondrial encephalomyopathy, Leigh syndrome, Amyotrophic Lateral Sclerosis (ALS), ataxia telangiectasia, obesity, atherosclerosis, heart failure, myocardial infarction, Parkinson's disease, Alzheimer's disease, Huntington's disease, schizophrenia, bipolar disorder cancer, fragile X syndrome or chronic fatigue syndrome in an animal comprising administering to the animal in need thereof a compound of formula I as described in claim 1 or a pharmaceutically acceptable salt thereof.

* * * * *